US009109259B2

(12) United States Patent
Takeuchi et al.

(10) Patent No.: US 9,109,259 B2
(45) Date of Patent: Aug. 18, 2015

(54) DETECTION METHOD FOR NOVEL ROS1 FUSIONS

(75) Inventors: Kengo Takeuchi, Tokyo (JP); Yuichi Ishikawa, Tokyo (JP); Hiroyuki Mano, Tochigi (JP); Manabu Soda, Tochigi (JP); Eirin Sai, Tochigi (JP)

(73) Assignees: Japanese Foundation for Cancer Research, Tokyo (JP); Educational Foundation Jichi Medical University, Shimotsuke-shi (JP)

( * ) Notice: Subject to any disclaimer, the term of this patent is extended or adjusted under 35 U.S.C. 154(b) by 0 days.

(21) Appl. No.: 13/805,513

(22) PCT Filed: Jun. 22, 2011

(86) PCT No.: PCT/JP2011/064272

§ 371 (c)(1), (2), (4) Date: Dec. 19, 2012

(87) PCT Pub. No.: WO2011/162295

PCT Pub. Date: Dec. 29, 2011

(65) Prior Publication Data

US 2013/0102006 A1 Apr. 25, 2013

(30) Foreign Application Priority Data

Jun. 22, 2010 (JP) ................................ 2010-141728

(51) Int. Cl.

| | |
|---|---|
| ***C12Q 1/68*** | (2006.01) |
| ***C12P 19/34*** | (2006.01) |
| ***G01N 33/574*** | (2006.01) |

(52) U.S. Cl.

CPC ............... *C12Q 1/6886* (2013.01); *C12P 19/34* (2013.01); *C12Q 1/68* (2013.01); *G01N 33/57484* (2013.01); *C12Q 2600/156* (2013.01)

(58) Field of Classification Search

CPC ................................ C12Q 1/68; C12P 19/34
USPC ................................................ 435/6.1, 91.2
See application file for complete search history.

(56) References Cited

U.S. PATENT DOCUMENTS

| | | | | |
|---|---|---|---|---|
| 7,294,504 | B1 * | 11/2007 | Wang | 435/320.1 |
| 2010/0143918 | A1 | 6/2010 | Guo et al. | |

FOREIGN PATENT DOCUMENTS

| | | |
|---|---|---|
| WO | 2007 084631 | 7/2007 |
| WO | 2009 051846 | 4/2009 |
| WO | 2009 054939 | 4/2009 |
| WO | 2010 093928 | 8/2010 |
| WO | 2011 146945 | 11/2011 |

OTHER PUBLICATIONS

Charest, A., et al., "Fusion of FIG to the Receptor Tyrosine Kinase ROS in a Glioblastoma with an Interstitial del(6)(q21q21)," Genes, Chromosomes, & Cancer, vol. 37, pp. 58-71, (2003).
Matsushime, H., et al., "Human c-ros-1 Gene Homologous to the v-ros Sequence of UR2 Sarcoma Virus Encodes for a Transmembrane Receptorlike Molecule," Molecular and Cellular Biology, vol. 6, No. 8, pp. 3000-3004, (Aug. 1986).
Charest, A., et al., "ROS Fusion Tyrosine Kinase Activates a SH2 Domain-Containing Phosphatase-2/Phosphatidylinositol 3-Kinase/ Mammalian Target of Rapamycin Signaling Axis to Form Glioblastoma in Mice," Cancer Research, vol. 66, pp. 7473-7481, (Aug. 2, 2006).
Rikova, K., et al., "Global Survey of Phosphotyrosine Signaling Indetifies Oncogenic Kinases in Lung Cancer," Cell, vol. 131, pp. 1190-1203, (Dec. 14, 2007).
Gui, T.L., et al., "Survey of Tyrosine Kinase Signaling Reveals ROS Kinase Fusions in Human Cholangiocarcinoma," PlosOne, vol. 6, No. 1, pp. 1-9, (Jan. 2011).
El-Deeb, I.M., et al., "ROS Receptor Tyrosine Kinase: A New Potential Target for Anticancer Drugs," Medicinal Research Reviews, vol. 31, No. 5, pp. 794-818, (2011).
International Search Report Issued Aug. 2, 2011 in PCT/JP11/64272 Filed Jun. 22, 2011.
Written Opinion issued in PCT/JP2011/064272 on Aug. 2, 2011.
Extended European Search Report issued in European Application No. 11798177.9 on Oct. 23, 2013.
J. Acquaviva et al., Biochimica et Biophysica Acta, vol. 1795, pp. 37-52 (2009).
K. Takeuchi et al., Nature Medicine, vol. 18, No. 3. pp. 378-381 (2012).

* cited by examiner

*Primary Examiner* — Ardin Marschel
(74) *Attorney, Agent, or Firm* — Oblon, McClelland, Maier & Neustadt, L.L.P.

(57) ABSTRACT

Polynucleotides which are novel causative genes for cancer are elucidated, and a detection method of the polynucleotides or polypeptides encoded by the polynucleotides, and a kit and a primer set for detection are provided, based on the knowledge gained by the elucidation. In the detection method, a fusion gene comprising part of an SDC4, CD74, EZR, SLC34A2, LRIG3, or TPM3 gene and part of a ROS1 gene, or a fusion protein encoded by the fusion gene is detected. The primer set or the detection kit comprises a sense primer designed based on a portion encoding SDC4, CD74, EZR, SLC34A2, LRIG3, or TPM3 and an antisense primer designed based on a portion encoding ROS1.

24 Claims, 4 Drawing Sheets

SDC4ex2−ROS1ex32

SDC4ex4−ROS1ex32

SDC4ex4−ROS1ex34

CD74ex6−ROS1ex32

EZRex10−ROS1ex34

SLC34A2ex13-ROS1ex32

LRIG3ex16-ROS1ex35

TPM3ex8-ROS1ex35 vector control

SDC4ex2-ROS1ex32

SDC4ex4−ROS1ex32

SDC4ex4−ROS1ex34

CD74ex6−ROS1ex32

EZRex10−ROS1ex34

SLC34A2ex13−ROS1ex32

LRIG3ex16−ROS1ex35

TPM3ex8−ROS1ex35 vector control

DETECTION METHOD FOR NOVEL ROS1 FUSIONS

TECHNICAL FIELD

The present invention relates to a method of detecting novel fusion genes comprising a ROS1 kinase region, or fusion proteins encoded by those fusion genes.

BACKGROUND ART

Nowadays the relationship of molecular diagnosis and therapeutic effects on cancer is being shown clinically by the appearance of tyrosine kinase inhibitors Iressa and Tarceva. As a result, the concept of drug administration to eligible patients stratified by molecular diagnosis is spreading.

A ROS1 kinase was identified as a human ortholog of e-ros, which is an oncogene of avian sarcoma virus UR2 (University of Rochester 2) (non-patent literature 1). ROS1 gene translocation was first found in glioblastoma, and its fusion partner was FIG (Fused in glioblastoma) (non-patent literature 2). The expression of full-length wild-type ROS1 has been observed in epithelial cells of a wide range of tissues, and a relationship with cancer has also been suggested. It is known that the ROS1 kinase activity becomes constitutive by the fusion of ROS1 with FIG, and that malignant transformation of cells which express the fusion occurs, and cancer occurs in a transgenic mouse with the fusion (non-patent literature 3).

It was reported that fusion genes of CD74 or SLC34A2 with ROS1 were present in non-small cell lung cancer (non-patent literature 4; the term “ROS” is used in non-patent literature 4 instead of “ROS1”). Because CD74-ROS1 was identified in 1 case from 150 patient specimens, and SLC34A2-ROS1 was identified in 1 case from 41 cell lines, the actual frequency in patients and the clinical characteristics of patients are unknown. The fusion site in the CD74-ROS1 gene which was reported in non-patent literature 4 was within exon 6 of the CD74 gene and exon 34 of the ROS1 gene, and no fusions were found in the other exons, and oncogenic potential was not shown. The fusion site of CD74ex6-ROS1ex32 which was found in the present invention is within exon 6 of the CD74 gene and exon 32 of the ROS1 gene. Further, the fusion sites in the SLC34A2-ROS1 gene which was reported in non-patent literature 4 were within exon 4 of the SLC34A2 gene and exon 32 or 34 of the ROS1 gene, and no fusions were found in the other exons. The fusion site of SLC34A2ex13-ROS1ex32 which was found in the present invention is within exon 13 of the SLC34A2 gene and exon 32 of the ROS1 gene.

CITATION LIST

Non-Patent Literature

[Non-patent literature 1] Molecular and cellular biology, (U.S.A.), 1986, vol. 6, p. 3000-3004

[Non-patent literature 2] Genes, chromosomes & cancer, (United Kingdom), 2003, vol. 37, p. 58-71

[Non-patent literature 3] Cancer research, (U.S.A.), 2006, vol. 66, p. 7473-7481

[Non-patent literature 4] Cell, (U.S.A.), 2007, vol. 131, p. 1190-1203

SUMMARY OF INVENTION

Technical Problem

An object of the present invention is to elucidate polynucleotides which are novel causative genes for cancer, and to provide a method of detecting the polynucleotides or polypeptides encoded by the polynucleotides, and a kit and a primer set for the detection, based on the knowledge gained.

Solution to Problem

The present inventors isolated and identified novel fusion genes in each of which part of a gene (SDC4, CD74, EZR, SLC34A2, LRIG3, TPM3) was fused to part of a ROS1 gene which encodes a kinase, from specimens obtained from lung cancer patients (Example 3), and found that these fusion genes were present in lung cancer patient specimens (Examples 5 and 6), and that the fusion genes exhibited oncogenic potential and were causative genes for cancer (Example 4). From these findings, the present inventors developed a method of detecting the fusion genes and fusion proteins encoded by the fusion genes (Examples 5 and 6), provided a kit and a primer set for the detection, and made it possible to select cancer patients to be treated with a ROS1 inhibitor by detecting the fusion genes.

The present invention relates to:

[1] a method of detecting a fusion gene comprising a ROS1 kinase region, or a fusion protein encoded by the fusion gene, characterized by comprising the step of:

detecting the presence of a polynucleotide encoding a polypeptide which is a fusion protein of SDC4, EZR, LRIG3, or TPM3 with ROS1, or the presence of the polypeptide, in a specimen obtained from a subject,

[2] a method of detecting a fusion gene comprising a ROS1 kinase region, or a fusion protein encoded by the fusion gene, characterized by comprising the step of:

detecting the presence of a polynucleotide encoding a polypeptide, or the presence of the polypeptide, in a specimen obtained from a subject, wherein the polypeptide is:

a polypeptide with oncogenic potential comprising an amino acid sequence having a 90% or higher identity with the amino acid sequence of SEQ ID NOS: 2, 4, 6, 8, 10, 12, 14, or 16,

[3] the method of [2], wherein the polypeptide is:

a polypeptide with oncogenic potential comprising the amino acid sequence of SEQ ID NOS: 2, 4, 6, 8, 10, 12, 14, or 16, or a polypeptide with oncogenic potential comprising an amino acid sequence in which 1 to 10 amino acids are deleted, substituted, and/or inserted in the amino acid sequence of SEQ ID NOS: 2, 4, 6, 8, 10, 12, 14, or 16,

[4] the method of [2], wherein the polypeptide is:

a polypeptide consisting of the amino acid sequence of SEQ ID NOS: 2, 4, 6, 8, 10, 12, 14, or 16,

[5] the method of detecting a fusion gene of any one of [1] to [4], characterized by comprising the step of:

detecting the presence of a polynucleotide encoding the polypeptide in a specimen obtained from a subject,

[6] a kit for detecting a fusion gene comprising a ROS1 kinase region, comprising a sense primer and an antisense primer, wherein the sense primer and the antisense primer are designed to be able to specifically amplify a polynucleotide encoding a polypeptide wherein the polypeptide is a fusion protein of SDC4, EZR, LRIG3, or TPM3 with ROS1,

[7] a kit for detecting a fusion gene comprising a ROS1 kinase region, comprising a sense primer and an antisense primer which are designed to be able to specifically amplify a polynucleotide encoding a polypeptide, wherein the polypeptide is:

a polypeptide with oncogenic potential comprising an amino acid sequence having a 90% or higher identity with the amino acid sequence of SEQ ID NOS: 2, 4, 6, 8, 10, 12, 14, or 16,

[8] the kit of [7], wherein the polypeptide is:

a polypeptide with oncogenic potential comprising the amino acid sequence of SEQ ID NOS: 2, 4, 6, 8, 10, 12, 14, or 16, or a polypeptide with oncogenic potential comprising an amino acid sequence in which 1 to 10 amino acids are deleted, substituted, and/or inserted in the amino acid sequence of SEQ ID NOS: 2, 4, 6, 8, 10, 12, 14, or 16,

[9] the kit of [7], wherein the polypeptide is:

a polypeptide consisting of the amino acid sequence of SEQ ID NOS: 2, 4, 6, 8, 10, 12, 14, or 16,

[10] a primer set for detecting a fusion gene of an SDC4, CD74, EZR, SLC34A2, LRIG3, or TPM3 gene with a ROS1 gene, comprising a sense primer designed based on a portion encoding SDC4, CD74, EZR, SLC34A2, LRIG3, or TPM3, and an antisense primer designed based on a portion encoding ROS1, wherein the antisense primer consists of a nucleic acid molecule hybridizing under stringent conditions to the polynucleotide described in any one of [1] to [4], and the sense primer consists of a nucleic acid molecule hybridizing under stringent conditions to a strand complementary to the polynucleotide described in any one of [1] to [4],

[11] a primer set for detecting a fusion gene of an SDC4, CD74, EZR, SLC34A2, LRIG3, or TPM3 gene with a ROS1 gene, selected from the group consisting of:

a) a primer set comprising an antisense primer and a sense primer, wherein the antisense primer consists of a nucleic acid molecule hybridizing under stringent conditions to a polynucleotide consisting of the nucleotide sequence of SEQ ID NO: 1, and the sense primer consists of a nucleic acid molecule hybridizing under stringent conditions to a strand complementary to the polynucleotide, b) a primer set comprising an antisense primer and a sense primer, wherein the antisense primer consists of a nucleic acid molecule hybridizing under stringent conditions to a polynucleotide consisting of the nucleotide sequence of SEQ ID NO: 3, and the sense primer consists of a nucleic acid molecule hybridizing under stringent conditions to a strand complementary to the polynucleotide, c) a primer set comprising an antisense primer and a sense primer, wherein the antisense primer consists of a nucleic acid molecule hybridizing under stringent conditions to a polynucleotide consisting of the nucleotide sequence of SEQ ID NO: 5, and the sense primer consists of a nucleic acid molecule hybridizing under stringent conditions to a strand complementary to the polynucleotide, d) a primer set comprising an antisense primer and a sense primer, wherein the antisense primer consists of a nucleic acid molecule hybridizing under stringent conditions to a polynucleotide consisting of the nucleotide sequence of SEQ ID NO: 7, and the sense primer consists of a nucleic acid molecule hybridizing under stringent conditions to a strand complementary to the polynucleotide, e) a primer set comprising an antisense primer and a sense primer, wherein the antisense primer consists of a nucleic acid molecule hybridizing under stringent conditions to a polynucleotide consisting of the nucleotide sequence of SEQ ID NO: 9, and the sense primer consists of a nucleic acid molecule hybridizing under stringent conditions to a strand complementary to the polynucleotide, f) a primer set comprising an antisense primer and a sense primer, wherein the antisense primer consists of a nucleic acid molecule hybridizing under stringent conditions to a polynucleotide consisting of the nucleotide sequence of SEQ ID NO: 11, and the sense primer consists of a nucleic acid molecule hybridizing under stringent conditions to a strand complementary to the polynucleotide, g) a primer set comprising an antisense primer and a sense primer, wherein the antisense primer consists of a nucleic acid molecule hybridizing under stringent conditions to a polynucleotide consisting of the nucleotide sequence of SEQ ID NO: 13, and the sense primer consists of a nucleic acid molecule hybridizing under stringent conditions to a strand complementary to the polynucleotide, and h) a primer set comprising an antisense primer and a sense primer, wherein the antisense primer consists of a nucleic acid molecule hybridizing under stringent conditions to a polynucleotide consisting of the nucleotide sequence of SEQ ID NO: 15, and the sense primer consists of a nucleic acid molecule hybridizing under stringent conditions to a strand complementary to the polynucleotide,

[12] a primer set of a sense primer which is an oligonucleotide consisting of at least 16 consecutive nucleotides in the region of nucleotides 1-199 of SEQ ID NO: 1, and an antisense primer which is an oligonucleotide complementary to at least 16 consecutive nucleotides in the region of nucleotides 200-1995 of SEQ ID NO: 1.

[13] a primer set of a sense primer which is an oligonucleotide consisting of at least 16 consecutive nucleotides in the region of nucleotides 1-445 of SEQ ID NO: 3, and an antisense primer which is an oligonucleotide complementary to at least 16 consecutive nucleotides in the region of nucleotides 446-2241 of SEQ ID NO: 3,

[14] a primer set of a sense primer which is an oligonucleotide consisting of at least 16 consecutive nucleotides in the region of nucleotides 1-445 of SEQ ID NO: 5, and an antisense primer which is an oligonucleotide complementary to at least 16 consecutive nucleotides in the region of nucleotides 446-1932 of SEQ ID NO: 5,

[15] a primer set of a sense primer which is an oligonucleotide consisting of at least 16 consecutive nucleotides in the region of nucleotides 1-625 of SEQ ID NO: 7, and an antisense primer which is an oligonucleotide complementary to at least 16 consecutive nucleotides in the region of nucleotides 626-2421 of SEQ ID NO: 7,

[16] a primer set of a sense primer which is an oligonucleotide consisting of at least 16 consecutive nucleotides in the region of nucleotides 1-1090 of SEQ ID NO: 9, and an antisense primer which is an oligonucleotide complementary to at least 16 consecutive nucleotides in the region of nucleotides 1091-2577 of SEQ ID NO: 9,

[17] a primer set of a sense primer which is an oligonucleotide consisting of at least 16 consecutive nucleotides in the region of nucleotides 1-2026 of SEQ ID NO: 11, and an antisense primer which is an oligonucleotide complementary to at least 16 consecutive nucleotides in the region of nucleotides 2027-3822 of SEQ ID NO: 11,

[18] a primer set of a sense primer which is an oligonucleotide consisting of at least 16 consecutive nucleotides in the region of nucleotides 1-2695 of SEQ ID NO: 13, and an antisense primer which is an oligonucleotide complementary to at least 16 consecutive nucleotides in the region of nucleotides 2696-4098 of SEQ ID NO: 13, and

[19] a primer set of a sense primer which is an oligonucleotide consisting of at least 16 consecutive nucleotides in the region of nucleotides 1-775 of SEQ ID NO: 15, and an antisense primer which is an oligonucleotide complementary to at least 16 consecutive nucleotides in the region of nucleotides 776-2178 of SEQ ID NO: 15.

The present invention relates to a method of detecting the presence of cancer (particularly, lung cancer) positive for a fusion gene comprising a ROS1 kinase region, characterized by comprising the step of:

detecting the presence of a polynucleotide encoding a polypeptide in a specimen obtained from a subject, wherein the polypeptide is:

(1) a polypeptide with oncogenic potential comprising the amino acid sequence of SEQ ID NOS: 2, 4, 6, 8, 10, 12, 14, or 16, or a polypeptide with oncogenic potential comprising an amino acid sequence in which 1 to 10 amino acids are deleted, substituted, and/or inserted in the amino acid sequence of SEQ ID NOS: 2, 4, 6, 8, 10, 12, 14, or 16, (2) a polypeptide with oncogenic potential comprising an amino acid sequence having a 90% or higher identity with the amino acid sequence of SEQ ID NOS: 2, 4, 6, 8, 10, 12, 14, or 16, or (3) a polypeptide consisting of the amino acid sequence of SEQ ID NOS: 2, 4, 6, 8, 10, 12, 14, or 16.

The present invention relates to a method of diagnosing cancer (particularly, lung cancer) positive for a fusion gene comprising a ROS1 kinase region, characterized by comprising the step of:

detecting the presence of a polynucleotide encoding a polypeptide in a specimen obtained from a subject, wherein the polypeptide is:

(1) a polypeptide with oncogenic potential comprising the amino acid sequence of SEQ ID NOS: 2, 4, 6, 8, 10, 12, 14, or 16, or a polypeptide with oncogenic potential comprising an amino acid sequence in which 1 to 10 amino acids are deleted, substituted, and/or inserted in the amino acid sequence of SEQ ID NOS: 2, 4, 6, 8, 10, 12, 14, or 16, (2) a polypeptide with oncogenic potential comprising an amino acid sequence having a 90% or higher identity with the amino acid sequence of SEQ ID NOS: 2, 4, 6, 8, 10, 12, 14, or 16, or (3) a polypeptide consisting of the amino acid sequence of SEQ ID NOS: 2, 4, 6, 8, 10, 12, 14, or 16.

The present invention relates to a method of detecting the presence of cancer (particularly, lung cancer), characterized by comprising the steps of:

carrying out PCR using a specimen obtained from a subject as a template, together with the aforementioned primer set, and detecting the presence of a PCR product.

The present invention relates to a method of detecting genomic rearrangement, characterized by comprising the step of:

detecting the presence of a polynucleotide encoding a polypeptide in a specimen obtained from a subject, wherein the polypeptide is:

(1) a polypeptide with oncogenic potential comprising the amino acid sequence of SEQ ID NOS: 2, 4, 6, 8, 10, 12, 14, or 16, or a polypeptide with oncogenic potential comprising an amino acid sequence in which 1 to 10 amino acids are deleted, substituted, and/or inserted in the amino acid sequence of SEQ ID NOS: 2, 4, 6, 8, 10, 12, 14, or 16, (2) a polypeptide with oncogenic potential comprising an amino acid sequence having a 90% or higher identity with the amino acid sequence of SEQ ID NOS: 2, 4, 6, 8, 10, 12, 14, or 16, or (3) a polypeptide consisting of the amino acid sequence of SEQ ID NOS: 2, 4, 6, 8, 10, 12, 14, or 16.

The present invention relates to a method of detecting genomic rearrangement, characterized by comprising the steps of:

carrying out in situ hybridization using i) a specimen obtained from a subject, ii) a labeled probe comprising a 5' side genomic region encoding SDC4, CD74, EZR, SLC34A2, LRIG3, or TPM3, and iii) a fluorescence-labeled probe comprising a 3' genomic region encoding ROS1, and detecting the overlap of signals from the labels.

Advantageous Effects of Invention

The detection method of the present invention can be used as a method of detecting cancer (particularly, lung cancer) positive for fusion genes of each of SDC4, CD74, EZR, SLC34A2, LRIG3, and TPM3 genes with a ROS1 gene. The detection method of the present invention can be used as a method of detecting genomic rearrangement. Using the detection method of the present invention, it can be determined whether or not a patient is eligible for ROS1 inhibitors. The detection kit and the primer set of the present invention can be used for the detection method of the present invention.

DESCRIPTION OF EMBODIMENTS

<<Detection Method of the Present Invention>>

Figure 1:
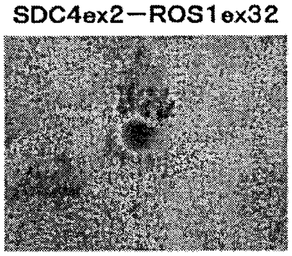
FIG. 1 is a micrograph, in place of drawings, showing the state of 3T3 fibroblasts which had been cultivated for 14 days after the introduction of fusion gene SDC4ex2-ROS1ex32 (SEQ ID NO: 1).
Figure 2:
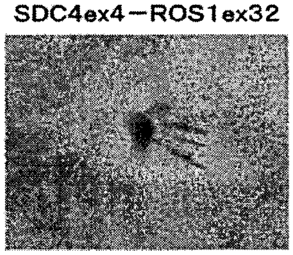
FIG. 2 is a micrograph, in place of drawings, showing the state of 3T3 fibroblasts which had been cultivated for 14 days after the introduction of fusion gene SDC4ex4-ROS1ex32 (SEQ ID NO: 3).
Figure 3:
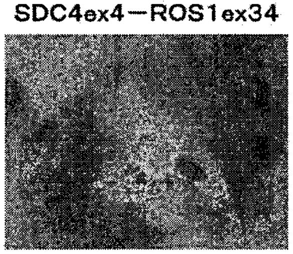
FIG. 3 is a micrograph, in place of drawings, showing the state of 3T3 fibroblasts which had been cultivated for 14 days after the introduction of fusion gene SDC4ex4-ROS1ex34 (SEQ ID NO: 5).
Figure 4:
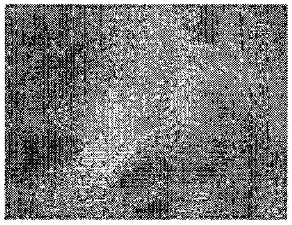
FIG. 4 is a micrograph, in place of drawings, showing the state of 3T3 fibroblasts which had been cultivated for 14 days after the introduction of fusion gene CD74ex6-ROS1ex32 (SEQ ID NO: 7).
Figure 5:
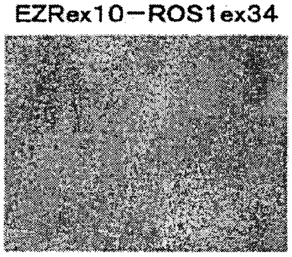
FIG. 5 is a micrograph, in place of drawings, showing the state of 3T3 fibroblasts which had been cultivated for 14 days after the introduction of fusion gene EZRex10-ROS1ex34 (SEQ ID NO: 9).
Figure 6:
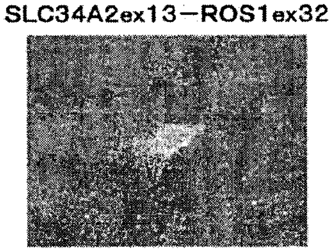
FIG. 6 is a micrograph, in place of drawings, showing the state of 3T3 fibroblasts which had been cultivated for 14 days after the introduction of fusion gene SLC34A2ex13-ROS1ex32 (SEQ ID NO: 11).
Figure 7:
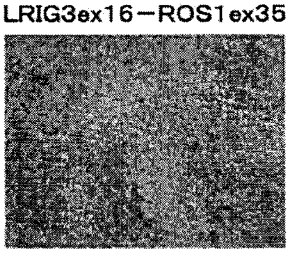
FIG. 7 is a micrograph, in place of drawings, showing the state of 3T3 fibroblasts which had been cultivated for 14 days after the introduction of fusion gene LRIG3ex16-ROS1ex35 (SEQ ID NO: 13).
Figure 8:
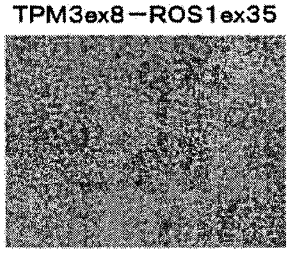
FIG. 8 is a micrograph, in place of drawings, showing the state of 3T3 fibroblasts which had been cultivated for 14 days after the introduction of fusion gene TPM3ex8-ROS1ex35 (SEQ ID NO: 15).

The detection method of the present invention includes a method of detecting a fusion gene, and a method of detecting a fusion protein encoded by the fusion gene. Hereinafter the method of detecting a fusion gene will be explained, and then, the method of detecting a fusion protein will be explained.

The method of detecting a fusion gene according to the present invention comprises the step of detecting the presence of a specific polynucleotide in a specimen obtained from a subject.

As the specimen obtained from a subject, specimens collected from a subject (i.e., samples isolated from a living body), more specifically, body fluids (preferably blood), bronchoalveolar lavage fluid, biopsy specimens, or sputum are used, and a biopsy specimen from the affected part of the lung, or sputum is preferred. Genomic DNA extracted from a specimen, or its transcripts (products generated by transcription and translation of the genome, such as mRNA, cDNA, and protein) may be used. In particular, it is preferable to prepare and use mRNA or cDNA.

In the "step of detecting the presence of a specific polynucleotide" in the method of detecting a fusion gene, the polynucleotide to be detected (hereinafter referred to as a polynucleotide to be detected) is at least one of fusion genes containing a ROS1 kinase region. The "fusion genes containing a ROS1 kinase region" as used herein means (A) polynucleotides encoding polypeptides which are fusion proteins of any one of parts of SDC4, EZR, LRIG3, and TPM3 with part of ROS1 (preferably, a polynucleotide consisting of a nucleotide sequence from the initiation codon ATG to exon 2 of an SDC4 gene and a nucleotide sequence from exon 32 to the stop codon of exon 43 of the ROS1 gene, a polynucleotide consisting of a nucleotide sequence from the initiation codon ATG to exon 4 of an SDC4 gene and a nucleotide sequence from exon 32 to the stop codon of exon 43 of the ROS1 gene, a polynucleotide consisting of a nucleotide sequence from the initiation codon ATG to exon 4 of an SDC4 gene and a nucleotide sequence from exon 34 to the stop codon of exon 43 of the ROS1 gene, a polynucleotide consisting of a nucleotide sequence from the initiation codon ATG to exon 10 of an EZR gene and a nucleotide sequence from exon 34 to the stop codon of exon 43 of the ROS1 gene, a polynucleotide consisting of a nucleotide sequence from the initiation codon ATG to exon 16 of an LRIG3 gene and a nucleotide sequence from exon 35 to the stop codon of exon 43 of the ROS1 gene, and a polynucleotide consisting of a nucleotide sequence from the initiation codon ATG to exon 8 of a TPM3 gene and a nucleotide sequence from exon 35 to the stop codon of exon 43 of the ROS1 gene), and (B) a polynucleotide consisting of a nucleotide sequence from the initiation codon ATG to exon 6 of a CD74 gene and a nucleotide sequence from exon 32 to the stop codon of exon 43 of the ROS1 gene, and a polynucleotide consisting of a nucleotide sequence from the initiation codon ATG to exon 13 of an SLC34A2 gene and a nucleotide sequence from exon 32 to the stop codon of exon 43 of the ROS1 gene.

As the "fusion genes containing a ROS1 kinase region", polynucleotides encoding the following polypeptides (i) to (iii) are most preferable:

(i) a polypeptide with oncogenic potential comprising the amino acid sequence of SEQ ID NOS: 2, 4, 6, 8, 10, 12, 14, or 16, or a polypeptide with oncogenic potential comprising an amino acid sequence in which 1 to 10 amino acids are deleted, substituted, and/or inserted in the amino acid sequence of SEQ ID NOS: 2, 4, 6, 8, 10, 12, 14, or 16 (hereinafter referred to as a variation functionally equivalent), (ii) a polypeptide with oncogenic potential comprising an amino acid sequence having a 90% or higher identity with the amino acid sequence of SEQ ID NOS: 2, 4, 6, 8, 10, 12, 14, or 16 (hereinafter referred to as a homologous polypeptide), and (iii) a polypeptide consisting of the amino acid sequence of SEQ ID NOS: 2, 4, 6, 8, 10, 12, 14, or 16.

The amino acid sequence of SEQ ID NO: 2 is the sequence encoded by the nucleotide sequence of SEQ ID NO: 1. The nucleotide sequence of SEQ ID NO: 1 consists of a nucleotide sequence from the initiation codon ATG to exon 2 of the SDC4 gene and a nucleotide sequence from exon 32 to the stop codon of exon 43 of the ROS1 gene. In the nucleotide sequence of SEQ ID NO: 1, nucleotides 1-199 is derived from the SDC4 gene, and nucleotides 200-1995 is derived from the ROS1 gene. Hereinafter, the polynucleotide consisting of the nucleotide sequence of SEQ ID NO: 1 is referred to as SDC4ex2-ROS1ex32.

The amino acid sequence of SEQ ID NO: 4 is the sequence encoded by the nucleotide sequence of SEQ ID NO: 3. The nucleotide sequence of SEQ ID NO: 3 consists of a nucleotide sequence from the initiation codon ATG to exon 4 of the SDC4 gene and a nucleotide sequence from exon 32 to the stop codon of exon 43 of the ROS1 gene. In the nucleotide sequence of SEQ ID NO: 3, nucleotides 1-445 is derived from the SDC4 gene, and nucleotides 446-2241 is derived from the ROS1 gene. Hereinafter, the polynucleotide consisting of the nucleotide sequence of SEQ ID NO: 3 is referred to as SDC4ex4-ROS1ex32.

The amino acid sequence of SEQ ID NO: 6 is the sequence encoded by the nucleotide sequence of SEQ ID NO: 5. The nucleotide sequence of SEQ ID NO: 5 consists of a nucleotide sequence from the initiation codon ATG to exon 4 of the SDC4 gene and a nucleotide sequence from exon 34 to the stop codon of exon 43 of the ROS1 gene. In the nucleotide sequence of SEQ ID NO: 5, nucleotides 1-445 is derived from the SDC4 gene, and nucleotides 446-1932 is derived from the ROS1 gene. Hereinafter, the polynucleotide consisting of the nucleotide sequence of SEQ ID NO: 5 is referred to as SDC4ex4-ROS1ex34.

The amino acid sequence of SEQ ID NO: 8 is the sequence encoded by the nucleotide sequence of SEQ ID NO: 7. The nucleotide sequence of SEQ ID NO: 7 consists of a nucleotide sequence from the initiation codon ATG to exon 6 of the CD74 gene and a nucleotide sequence from exon 32 to the stop codon of exon 43 of the ROS1 gene. In the nucleotide sequence of SEQ ID NO: 7, nucleotides 1-625 is derived from the CD74 gene, and nucleotides 626-2421 is derived from the ROS1 gene. Hereinafter, the polynucleotide consisting of the nucleotide sequence of SEQ ID NO: 7 is referred to as CD74ex6-ROS1ex32.

The amino acid sequence of SEQ ID NO: 10 is the sequence encoded by the nucleotide sequence of SEQ ID NO: 9. The nucleotide sequence of SEQ ID NO: 9 consists of a nucleotide sequence from the initiation codon ATG to exon 10 of the EZR gene and a nucleotide sequence from exon 34 to the stop codon of exon 43 of the ROS1 gene. In the nucleotide sequence of SEQ ID NO: 9, nucleotides 1-1090 is derived from the EZR gene, and nucleotides 1091-2577 is derived from the ROS1 gene. Hereinafter, the polynucleotide consisting of the nucleotide sequence of SEQ ID NO: 9 is referred to as EZRex10-ROS1ex34.

The amino acid sequence of SEQ ID NO: 12 is the sequence encoded by the nucleotide sequence of SEQ ID NO: 11. The nucleotide sequence of SEQ ID NO: 11 consists of a nucleotide sequence from the initiation codon ATG to exon 13 of the SLC34A2 gene and a nucleotide sequence from exon 32 to the stop codon of exon 43 of the ROS1 gene. In the nucleotide sequence of SEQ ID NO: 11, nucleotides 1-2026 is derived from the SLC34A2 gene, and nucleotides 2027-3822 is derived from the ROS1 gene. Hereinafter, the polynucleotide consisting of the nucleotide sequence of SEQ ID NO: 11 is referred to as SLC34A2ex13-ROS1ex32.

The amino acid sequence of SEQ ID NO: 14 is the sequence encoded by the nucleotide sequence of SEQ ID NO: 13. The nucleotide sequence of SEQ ID NO: 13 consists of a nucleotide sequence from the initiation codon ATG to exon 16 of the LRIG3 gene and a nucleotide sequence from exon 35 to the stop codon of exon 43 of the ROS1 gene. In the nucleotide sequence of SEQ ID NO: 13, nucleotides 1-2695 is derived from the LRIG3 gene, and nucleotides 2696-4098 is derived from the ROS1 gene. Hereinafter, the polynucleotide consisting of the nucleotide sequence of SEQ ID NO: 13 is referred to as LRIG3ex16-ROS1ex35.

The amino acid sequence of SEQ ID NO: 16 is the sequence encoded by the nucleotide sequence of SEQ ID NO: 15. The nucleotide sequence of SEQ ID NO: 15 consists of a nucleotide sequence from the initiation codon ATG to exon 8 of the TPM3 gene and a nucleotide sequence from exon 35 to the stop codon of exon 43 of the ROS1 gene. In the nucleotide sequence of SEQ ID NO: 15, nucleotides 1-775 is derived from the TPM3 gene, and nucleotides 776-2178 is derived from the ROS1 gene. Hereinafter, the polynucleotide consisting of the nucleotide sequence of SEQ ID NO: 15 is referred to as TPM3ex8-ROS1ex35.

As the "variation functionally equivalent", preferable is "a polypeptide with oncogenic potential comprising an amino acid sequence in which 1 to 10 amino acids (more preferably 1 to several amino acids, still more preferably 1 to 7 amino acids, and still more preferably 1 to 5 amino acids) are deleted, substituted, and/or inserted in the amino acid sequence of SEQ ID NOS: 2, 4, 6, 8, 10, 12, 14, or 16". "A polypeptide with oncogenic potential comprising the amino acid sequence of SEQ ID NOS: 2, 4, 6, 8, 10, 12, 14, or 16" is most preferable.

The "homologous polypeptide" is "a polypeptide with oncogenic potential comprising an amino acid sequence having a 90% or higher identity with the amino acid sequence of SEQ ID NOS: 2, 4, 6, 8, 10, 12, 14, or 16", and is preferably a polypeptide comprising an amino acid having a 95% or higher identity, and more preferably a 98% or higher identity.

The term "identity" as used herein means a value obtained by a NEEDLE program (J Mol Biol 1970; 48: 443-453) search, using default parameters. The default parameters are as follows:

Gap penalty=10

Extend penalty=0.5

Matrix=EBLOSUM62

It can be determined by the method described in Example 4 whether a certain polypeptide "has oncogenic potential". More specifically, a nude mouse is subcutaneously inoculated with a host (3T3 fibroblasts) into which a plasmid expressing the polypeptide is transfected, and the oncogenic potential is determined by the presence or absence of tumor formation.

As the polynucleotide to be detected in the detection method of the present invention, a polynucleotide encoding "a polypeptide with oncogenic potential comprising the amino acid sequence of SEQ ID NOS: 2, 4, 6, 8, 10, 12, 14, or 16" is preferable, and a polynucleotide encoding "a polypeptide consisting of the amino acid sequence of SEQ ID NOS: 2, 4, 6, 8, 10, 12, 14, or 16" is most preferable.

The "step of detecting the presence of a polynucleotide" in the method of detecting a polynucleotide of the present invention is carried out by detecting the presence of a polynucleotide to be detected (a genomic sequence containing a fusion point) in the genome contained in a specimen collected from a subject, or by preparing transcripts (such as mRNA or cDNA) of genomic DNA extracted from a specimen collected from a subject and detecting the presence of mRNA or cDNA corresponding to the polynucleotide to be detected.

Genomic DNA may be extracted by a known method, and the extraction may be easily carried out using a commercially available DNA extraction kit.

The detection step may be carried out in accordance with a known gene analysis method, for example, well-known methods widely-used as a gene detection method, such as PCR, LCR (Ligase chain reaction), SDA (Strand displacement amplification), NASBA (Nucleic acid sequence-based amplification), ICAN (Isothermal and chimeric primer-initiated amplification of nucleic acids), a LAMP (Loop-mediated isothermal amplification) method, a TMA method (Gen-Probe's TMA system), in situ hybridization, and microarray. For example, a hybridization technique using, as a probe, nucleic acid capable of hybridizing to the polynucleotide to be detected, or a gene amplification technique using DNA capable of hybridizing to the polynucleotide to be detected as primers, is utilized.

Specifically, measurement is carried out using nucleic acid, such as mRNA, derived from a specimen collected from a subject. mRNA is measured by a gene amplification reaction method using primers designed to specifically amplify the nucleotide sequence of the polynucleotide to be detected. The primers used in the detection method of the present invention, or the primers contained in the detection kit of the present invention are not limited, so long as the polynucleotide sequence to be detected can be specifically amplified. The primers are designed, based on the nucleotide sequence of the polynucleotide to be detected. Primers used in a PCR amplification monitor method may be designed using a primer design software (for example, Primer Express; PE Biosystems). Because the amplification efficiency becomes poor when the length of a PCR product is long, it is preferable that the sense and antisense primers are designed to give the size of the PCR product of 1 kb or less when mRNA or cDNA is amplified as the target.

More specifically, the sense primer (5'-primer) is designed based on a portion encoding SDC4, CD74, EZR, SLC34A2, LRIG3, or TPM3 [for example, a desired portion in each gene region of SDC4, CD74, EZR, SLC34A2, LRIG3, or TPM3 contained in each fusion polynucleotide (particularly, cDNA) of SDC4-ROS1, CD74-ROS1, EZR-ROS1, SLC34A2-ROS1, LRIG3-ROS1, or TPM3-ROS1 (particularly, SDC4ex2-ROS1ex32, SDC4ex4-ROS1ex32, SDC4ex4-ROS1ex34, CD74ex6-ROS1ex32, EZRex10-ROS1ex34, SLC34A2ex13-ROS1ex32, LRIG3ex16-ROS1ex35, or TPM3ex8-ROS1ex35)]. The antisense primer (3'-primer) is designed based on a portion encoding ROS1 [for example, a desired portion in the ROS1 gene region of each fusion polynucleotide (particularly, cDNA)]. Preferably, primers contained in the detection kit of the present invention are used, and more preferably, primers most preferably contained in the detection kit are used. In a PCR amplification monitor method, a multiplex PCR in which all the fusion polynucleotides are detected with a single reaction liquid may be designed by mixing the sense primers corresponding to each gene. It can be determined by a method suitable to each amplification technique whether or not a gene of interest (the whole or its specific portion) is amplified. For example, in a PCR method, whether or not an amplified fragment of the desired size is obtained can be determined by subjecting a PCR product to agarose gel electrophoresis and analyzing it by ethidium bromide staining or the like. When an amplified fragment of the desired size is obtained, it can be concluded that the polynucleotide to be detected is present in the specimen collected from a subject. The presence of the polynucleotide to be detected can be detected as described above.

It is preferable that the method of detecting a fusion gene of the present invention comprises not only the step of detecting the presence of a specific polynucleotide in a specimen obtained from a subject by a gene amplification method, but also the step of detecting whether or not an amplified fragment of the desired size is obtained.

The detection utilizing hybridization technique is carried out using, for example, Northern hybridization, dot blotting, DNA microarray, RNA protection, or the like. As the probe used in hybridization, a nucleic acid molecule consisting of at least 32 consecutive nucleotides hybridizing under stringent conditions (preferably, more stringent conditions) to a polynucleotide to be detected or its complementary strand, and comprising a sequence consisting of each 16 nucleotides upstream and downstream from the fusion point (specifically, nucleotides 184-215 (199/200) in the nucleotide sequence of SEQ ID NO: 1, nucleotides 430-461 (445/446) in the nucleotide sequence of SEQ ID NO: 3, nucleotides 430-461 (445/446) in the nucleotide sequence of SEQ ID NO: 5, nucleotides 610-641 (625/626) in the nucleotide sequence of SEQ ID NO: 7, nucleotides 1075-1106 (1090/1091) in the nucleotide sequence of SEQ ID NO: 9, nucleotides 2011-2042 (2026/2027) in the nucleotide sequence of SEQ ID NO: 11, nucleotides 2680-2711 (2695/2696) in the nucleotide sequence of SEQ ID NO: 13, and nucleotides 760-791 (775/776) in the nucleotide sequence of SEQ ID NO: 15;

nucleotide numbers in parentheses represent the fusion point), or its complementary strand may be used.

The detection utilizing in situ hybridization technique may be carried out in accordance with a known FISH method (fusion assay). Alternatively, it may be carried out by another fusion assay which is a combination of chromogenic in situ hybridization (CISH) and silver in situ hybridization (SISH). Preferably, the detection may be carried out by the FISH method (fusion assay) described in Example 6.

The term "fusion point" as used herein means a point in which a portion derived from each gene of SDC4, CD74, EZR, SLC34A2, LRIG3, or TPM3 is fused to a portion derived from the ROS1 gene.

The term "under stringent conditions" as used herein means the hybridization is carried out in a solution containing 5×SSPE, 5×Denhardt's solution, 0.5% SDS, 50% formamide, and 200 μg/mL salmon sperm DNA at 42° C. overnight, and the washing is carried out in a solution containing 0.5×SSC and 0.1% SDS at 42° C. The term "under more stringent conditions" as used herein means the hybridization is carried out in a solution containing 5×SSPE, 5×Denhardt's solution, 0.5% SDS, 50% formamide, and 200 μg/mL salmon sperm DNA at 42° C. overnight, and the washing is carried out in a solution containing 0.2×SSC and 0.1% SDS at 65° C.

Further, gene amplification techniques such as RT-PCR may be utilized. In RT-PCR, the presence of a polynucleotide to be detected may be more quantitatively analyzed, using a PCR amplification monitor (real-time PCR) method (Genome Res., 6(10), 986, 1996) in the gene amplification step. As the PCR amplification monitor method, for example, ABI PRISM7900 (PE Biosystems) may be used. Real-time PCR is a known method, and may be easily carried out using a commercially available apparatus and kit therefor.

The method of detecting a fusion protein of the present invention comprises the step of detecting the presence of a specific polypeptide, i.e., a polypeptide encoded by a polynucleotide to be detected (hereinafter referred to as a polypeptide to be detected), in a specimen obtained by a subject.

The detection step may be carried out by preparing a solubilized liquid derived from a specimen obtained from a subject (for example, a cancer tissue or cells obtained from a subject), and detecting a polypeptide to be detected (for example, a fusion polypeptide selected from SDC4-ROS1, CD74-ROS1, EZR-ROS1, SLC34A2-ROS1, LRIG3-ROS1, or TPM3-ROS1, in particular, a fusion polypeptide selected from SDC4ex2-ROS1ex32, SDC4ex4-ROS1ex32, SDC4ex4-ROS1ex34, CD74ex6-ROS1ex32, EZRex10-ROS1ex34, SLC34A2ex13-ROS1ex32, LRIG3ex16-ROS1ex35, or TPM3ex8-ROS1ex35) contained in the solubilized liquid by an immunoassay, an enzyme activity assay, or the like, using a combination of an antibody against SDC4, CD74, EZR, SLC34A2, LRIG3, or TPM3 and an anti-ROS1 antibody. Preferably, enzyme immunoassay, two antibody sandwich ELISA, fluorescence immunoassay, radioimmunoassay, Western blotting, or the like using a monoclonal or polyclonal antibody specific to a polypeptide to be detected may be used.

More specifically, the presence of a polypeptide to be detected may be detected by subjecting a cell extract prepared from cells suspected of containing the polypeptide to be detected to immunoprecipitation using an antibody against SDC4, CD74, EZR, SLC34A2, LRIG3, or TPM3, and detecting the precipitate using an anti-ROS1 antibody. The immunoprecipitation may be carried out using an anti-ROS1 antibody, and the detection may be carried out using an antibody against SDC4, CD74, EZR, SLC34A2, LRIG3, or TPM3. After the immunoprecipitation and the detection, it is preferable to confirm that the detected polypeptide has the same size as that of the polypeptide to be detected, using a detection antibody. The detection antibody may be an antibody specific to a polypeptide within exon 1 to exon 4 (preferably, exon 1 to exon 2) for SDC4, exon 1 to exon 6 for CD74, exon 1 to exon 10 for EZR, exon 1 to exon 13 for SLC34A2, exon 1 to exon 16 for LRIG3, exon 1 to exon 8 for TPM3, or exon 32 to exon 43 (preferably, exon 34 to exon 43, more preferably, exon 35 to exon 43) for ROS1, and may be a monoclonal or polyclonal antibody.

When the polynucleotide to be detected or the polypeptide to be detected in the detection method of the present invention is detected in a specimen obtained from a subject, the subject is a subject (patient) with cancer positive to the polynucleotide, and is subject to the treatment with ROS1 inhibitors.

<<Detection Kit of the Present Invention and Primer Set of the Present Invention>>

The detection kit of the present invention comprises at least a sense primer and an antisense primer designed to specifically amplify the polynucleotide to be detected in the detection method of the present invention. The sense and antisense primer set is a set of polynucleotides which function as primers for amplifying the polynucleotide to be detected.

The "fusion gene of the SDC4 gene with the ROS1 gene" means a gene in which part of the SDC4 gene is fused to part of the ROS1 gene (hereinafter referred to as SDC4-ROS1), preferably, a polynucleotide consisting of a nucleotide sequence from the initiation codon ATG to exon 2 of the SDC4 gene and a nucleotide sequence from exon 32 to the stop codon of exon 43 of the ROS1 gene, a polynucleotide consisting of a nucleotide sequence from the initiation codon ATG to exon 4 of the SDC4 gene and a nucleotide sequence from exon 32 to the stop codon of exon 43 of the ROS1 gene, or a polynucleotide consisting of a nucleotide sequence from the initiation codon ATG to exon 4 of the SDC4 gene and a nucleotide sequence from exon 34 to the stop codon of exon 43 of the ROS1 gene.

The "fusion gene of the EZR gene with the ROS1 gene" means a gene in which part of the EZR gene is fused to part of the ROS1 gene (hereinafter referred to as EZR-ROS1), preferably, a polynucleotide consisting of a nucleotide sequence from the initiation codon ATG to exon 10 of the EZR gene and a nucleotide sequence from exon 34 to the stop codon of exon 43 of the ROS1 gene.

The "fusion gene of the LRIG3 gene with the ROS1 gene" means a gene in which part of the LRIG3 gene is fused to part of the ROS1 gene (hereinafter referred to as LRIG3-ROS1), preferably, a polynucleotide consisting of a nucleotide sequence from the initiation codon ATG to exon 16 of the LRIG3 gene and a nucleotide sequence from exon 35 to the stop codon of exon 43 of the ROS1 gene.

The "fusion gene of the TPM3 gene with the ROS1 gene" means a gene in which part of the TPM3 gene is fused to part of the ROS1 gene (hereinafter referred to as TPM3-ROS1), preferably, a polynucleotide consisting of a nucleotide sequence from the initiation codon ATG to exon 8 of the TPM3 gene and a nucleotide sequence from exon 35 to the stop codon of exon 43 of the ROS1 gene.

The gene in which part of the CD74 gene is fused to part of the ROS1 gene (hereinafter referred to as CD74-ROS1) means a polynucleotide consisting of a nucleotide sequence from the initiation codon ATG to exon 6 of the CD74 gene and a nucleotide sequence from exon 32 to the stop codon of exon 43 of the ROS1 gene.

The gene in which part of the SLC34A2 gene is fused to part of the ROS1 gene (hereinafter referred to as SLC34A2-ROS1) means a polynucleotide consisting of a nucleotide sequence from the initiation codon ATG to exon 13 of the SLC34A2 gene and a nucleotide sequence from exon 32 to the stop codon of exon 43 of the ROS1 gene.

Fusion proteins encoded by SDC4-ROS1, CD74-ROS1, EZR-ROS1, SLC34A2-ROS1, LRIG3-ROS1, and TPM3-ROS1 are respectively designated as a fusion protein of SDC4 with ROS1, a fusion protein of CD74 with ROS1, a fusion protein of EZR with ROS1, a fusion protein of SLC34A2 with ROS1, a fusion protein of LRIG3 with ROS1, and a fusion protein of TPM3 with ROS1.

The primer set of the present invention includes (1) a primer set for detecting a fusion gene of the SDC4, CD74, EZR, SLC34A2, LRIG3, or TPM3 gene with the ROS1 gene, the primer set comprising a sense primer designed based on a portion encoding SDC4, CD74, EZR, SLC34A2, LRIG3, or TPM3 and an antisense primer designed based on a portion encoding ROS1, wherein the antisense primer consists of a nucleic acid molecule (preferably, a nucleic acid molecule consisting of at least 16 nucleotides) hybridizing under stringent conditions (preferably, under more stringent conditions) to the "polynucleotide to be detected", and the sense primer consists of a nucleic acid molecule (preferably, a nucleic acid molecule consisting of at least 16 nucleotides) hybridizing under stringent conditions (preferably, under more stringent conditions) to a strand complementary to the "polynucleotide to be detected".

As embodiments of the primer set (1), the primer set of the present invention includes the following primer sets (2) to (9):

(2) A primer set of a sense primer (preferably, SEQ ID NO: 34) which is an oligonucleotide consisting of at least 16 consecutive nucleotides in the region of nucleotides 1-199 of SEQ ID NO: 1 (SDC4ex2-ROS1ex32), and an antisense primer (preferably, SEQ ID NO: 31) which is an oligonucleotide complementary to at least 16 consecutive nucleotides in the region of nucleotides 200-1995 of SEQ ID NO: 1.

(3) A primer set of a sense primer (preferably, SEQ ID NO: 34) which is an oligonucleotide consisting of at least 16 consecutive nucleotides in the region of nucleotides 1-445 of SEQ ID NO: 3 (SDC4ex4-ROS1ex32), and an antisense primer (preferably, SEQ ID NO: 31) which is an oligonucleotide complementary to at least 16 consecutive nucleotides in the region of nucleotides 446-2241 of SEQ ID NO: 3.

(4) A primer set of a sense primer (preferably, SEQ ID NO: 34) which is an oligonucleotide consisting of at least 16 consecutive nucleotides in the region of nucleotides 1-445 of SEQ ID NO: 5 (SDC4ex4-ROS1ex34), and an antisense primer (preferably, SEQ ID NO: 31) which is an oligonucleotide complementary to at least 16 consecutive nucleotides in the region of nucleotides 446-1932 of SEQ ID NO: 5.

(5) A primer set of a sense primer (preferably, SEQ ID NO: 35) which is an oligonucleotide consisting of at least 16 consecutive nucleotides in the region of nucleotides 1-625 of SEQ ID NO: 7 (CD74ex6-ROS1ex32), and an antisense primer (preferably, SEQ ID NO: 31) which is an oligonucleotide complementary to at least 16 consecutive nucleotides in the region of nucleotides 626-2421 of SEQ ID NO: 7.

(6) A primer set of a sense primer (preferably, SEQ ID NO: 36) which is an oligonucleotide consisting of at least 16 consecutive nucleotides in the region of nucleotides 1-1090 of SEQ ID NO: 9 (EZRex10-ROS1ex34), and an antisense primer (preferably, SEQ ID NO: 33) which is an oligonucleotide complementary to at least 16 consecutive nucleotides in the region of nucleotides 1091-2577 of SEQ ID NO: 9.

(7) A primer set of a sense primer (preferably, SEQ ID NO: 37) which is an oligonucleotide consisting of at least 16 consecutive nucleotides in the region of nucleotides 1-2026 of SEQ ID NO: 11 (SLC34A2ex13-ROS1ex32), and an antisense primer (preferably, SEQ ID NO: 31) which is an oligonucleotide complementary to at least 16 consecutive nucleotides in the region of nucleotides 2027-3822 of SEQ ID NO: 11.

(8) A primer set of a sense primer (preferably, SEQ ID NO: 38) which is an oligonucleotide consisting of at least 16 consecutive nucleotides in the region of nucleotides 1-2695 of SEQ ID NO: 13 (LRIG3ex16-ROS1ex35), and an antisense primer (preferably, SEQ ID NO: 32) which is an oligonucleotide complementary to at least 16 consecutive nucleotides in the region of nucleotides 2696-4098 of SEQ ID NO: 13.

(9) A primer set of a sense primer (preferably, SEQ ID NO: 39) which is an oligonucleotide consisting of at least 16 consecutive nucleotides in the region of nucleotides 1-775 of SEQ ID NO: 15 (TPM3ex8-ROS1ex35), and an antisense primer (preferably, SEQ ID NO: 31) which is an oligonucleotide complementary to at least 16 consecutive nucleotides in the region of nucleotides 776-2178 of SEQ ID NO: 15.

In the primer sets (1) to (9), the interval between the selected locations of the sense and antisense primers is preferably 1 kb or less, or the size of an amplified product amplified using the sense and antisense primers is preferably 1 kb or less.

The primer of the present invention has a chain length of, generally 15 to 40 nucleotides, preferably 16 to 24 nucleotides, more preferably 18 to 24 nucleotides, and most preferably 20 to 24 nucleotides.

The primer set of the present invention may be used for the amplification and detection of a polynucleotide to be detected in the detection method of the present invention. Each primer contained in the primer set of the present invention may be synthesized by, for example, but is by no means limited to, chemical synthesis.

EXAMPLES

The present invention now will be further illustrated by, but is by no means limited to, the following Examples.

Example 1

Detection of ROS1 Gene Abnormalities by FISH Method in Clinical Specimens

A method of observing the translocation of a gene by staining the 5' and 3' regions of a target gene with different dyes is known. This method, a kind of FISH method, is called a split assay. In the split assay, each of the 5' region and the 3' region of a gene of interest for chromosomal translocation is stained using probes labeled with different fluorescent dyes. For example, when fluorescent labeling is carried out using two probes labeled with Texas Red (red) and FITC (green), the normal state is detected as two yellow signals (a state where the green signal and the red signal are present in the vicinity), and a translocation or an inversion is detected as split green and red signals.

The ROS1 gene abnormalities were detected by a FISH method, split assay, in clinical specimens. Lung cancer tissues which had been excised by surgery, immobilized in 20% formalin, and embedded in paraffin were cut at a thickness of 4 μm, and placed on glass slides to prepare pathological sections. The FISH method was carried out in accordance with a reference (Takeuchi K, Choi Y L, Soda M, Inamura K, Togashi Y, Hatano S, Enomoto M, Takada S, Yamashita Y, Satoh Y, Okumura S, Nakagawa K, Ishikawa Y, Mano H. Multiplex reverse transcription-PCR screening for EML4-ALK fusion transcripts. Clin Cancer Res. 2008; 14: 6618-6624.). The unstained sections prepared were treated with a Histology FISH Accessory Kit (Dako), and subjected to hybridization with BAC (bacterial artificial chromosome) clones (clone Nos. RP1-179P9 and RP11-323117) which covered the 5' and 3' regions of ROS1 gene and were labeled with green and red fluorescent dyes, respectively. The resulting sections were stained with 4,6-diamino-2-phenylindole. The fluorescence was observed using a fluorescence microscope BX51 (Olympus). As a result, sections in which the green signals were observed separately from the red signals and the abnormalities in genomic structure were suggested were found. From the study in pathological sections of 1553 cases, we found 12 cases of sections which suggested the abnormalities in genomic structure of the ROS1 gene region.

Example 2

Identification of ROS1 Fusion Polynucleotide Genes in Clinical Specimens

RNAs derived from 12 cases of tissues in which the abnormalities in ROS1 genomic structure had been suggested by FISH analysis were used as templates to examine genes located at the 5' side of the kinase region of the ROS1 gene, in accordance with a protocol attached to a 5'-RACE kit (SMAT™ RACE cDNA Amplification Kit; Clonetech). More specifically, first strand cDNAs were synthesized using 0.5 μg of each RNA derived from clinical specimens and a reverse primer (SEQ ID NO: 17) designed for the kinase coding region of the ROS1 gene. The 5'-RACE (rapid amplification of cDNA ends) PCR was carried out using a UPM primer included in the kit and the reverse primer (SEQ ID NO: 17) together with a DNA polymerase (AmpliTaq Gold (R); Life Technologies Japan Ltd.) under the following cycle conditions:

a cycle of a reaction at 94° C. for 30 seconds and a reaction at 72° C. for 3 minutes was repeated 5 times;

a cycle of a reaction at 94° C. for 30 seconds, a reaction at 70° C. for 30 seconds, and a reaction at 72° C. for 3 minutes was repeated 5 times; and a cycle of a reaction at 94° C. for 30 seconds, a reaction at 68° C. for 30 seconds, and a reaction at 72° C. for 3 minutes was repeated 25 times.

The resulting RACE products were subjected to electrophoresis, and DNA fragments of around 1-2 kbp were purified. The resulting DNA fragments were subjected to TA cloning followed by sequence analysis in accordance with conventional methods. As a result, it was found that parts of an SDC4 gene (specimen Nos. #7130, #8701, and #26356), a CD74 gene (#6534, #148, and #10855), an EZR gene (#11994 and #9604), an SLC34A2 gene (#10286), and a TPM3 gene (#17970 and #8405) were independently fused to the 5' side of the kinase region of the ROS1 gene.

In one case (RNA derived from #20130) in the 12 cases, no amplified product was obtained after the RACE reaction, but an amplified product was observed when a primer of SEQ ID NO: 31 was used, and it was confirmed by sequence analysis that part of an LRIG3 gene was fused to the 5' side of the ROS1 gene. We assumed the presence of an LRIG3-ROS1 fusion gene in the #20130 specimen, and determined the presence in Examples 3 and 4 below, in parallel with the confirmation of the other fusion genes.

Example 3

Isolation of ROS1 Fusion Polynucleotide Genes from Clinical Specimens cDNAs (#7130, #26356, #6534, #11994, #10286, and #20130) derived from lung cancer clinical specimens in which the abnormalities in ROS1 genomic structure had been suggested by FISH analysis and the fused genes had been identified were used as templates to carry out PCR using a DNA polymerase (PrimeStar HS DNA polymerase) under the following cycle conditions (a cycle of a reaction at 98° C. for 10 seconds and a reaction at 68° C. for 4 to 4.5 minutes were repeated 25 to 37 times). The resulting amplified products were cloned into pT7Blue-2. As the primer sets, the following oligonucleotides were used:

1) for #7130 and #26356, oligonucleotides consisting of the nucleotide sequences of SEQ ID NOS: 20 and 18;

2) for #6534, oligonucleotides consisting of the nucleotide sequences of SEQ ID NOS: 21 and 19;

3) for #11994, oligonucleotides consisting of the nucleotide sequences of SEQ ID NOS: 22 and 18;

4) for #10286, oligonucleotides consisting of the nucleotide sequences of SEQ ID NOS: 23 and 18; and 5) for #20130, oligonucleotides consisting of the nucleotide sequences of SEQ ID NOS: 24 and 18.

The resulting amplified products were sequenced to identify novel polynucleotides consisting of each part (including the initiation codon ATG) of the SDC4, CD74, EZR, SLC34A2, and LRIG3 genes and part (including the stop codon) of exon 43 of the ROS1 gene. More specifically, the following polynucleotides were obtained:

from #7130, a polynucleotide consisting of a nucleotide sequence from the initiation codon ATG to exon 2 of the SDC4 gene and a nucleotide sequence from exon 32 to the stop codon of exon 43 of the ROS1 gene (SDC4ex2-ROS1ex32, SEQ ID NO: 1);

from #26356, a polynucleotide consisting of a nucleotide sequence from the initiation codon ATG to exon 4 of the SDC4 gene and a nucleotide sequence from exon 32 to the stop codon of exon 43 of the ROS1 gene (SDC4ex4-ROS1ex32, SEQ ID NO: 3), and a polynucleotide consisting of a nucleotide sequence from the initiation codon ATG to exon 4 of the SDC4 gene and a nucleotide sequence from exon 34 to the stop codon of exon 43 of the ROS1 gene (SDC4ex4-ROS1ex34, SEQ ID NO: 5);

from #6534, a polynucleotide consisting of a nucleotide sequence from the initiation codon ATG to exon 6 of the CD74 gene and a nucleotide sequence from exon 32 to the stop codon of exon 43 of the ROS1 gene (CD74ex6-ROS1ex32, SEQ ID NO: 7);

from #11994, a polynucleotide consisting of a nucleotide sequence from the initiation codon ATG to exon 10 of the EZR gene and a nucleotide sequence from exon 34 to the stop codon of exon 43 of the ROS1 gene (EZRex10-ROS1ex34, SEQ ID NO: 9);

from #10286, a polynucleotide consisting of a nucleotide sequence from the initiation codon ATG to exon 13 of the SLC34A2 gene and a nucleotide sequence from exon 32 to the stop codon of exon 43 of the ROS1 gene (SLC34A2ex13-ROS1ex32, SEQ ID NO: 11); and from #20130, a polynucleotide consisting of a nucleotide sequence from the initiation codon ATG to exon 16 of the LRIG3 gene and a nucleotide sequence from exon 35 to the stop codon of exon 43 of the ROS1 gene (LRIG3ex16-ROS1ex35, SEQ ID NO: 13).

With respect to the fusion gene of the TPM3 gene with the ROS1 gene, the full-length thereof could not be amplified by a single PCR reaction. Therefore, cDNA #17970 derived from lung cancer clinical specimen was used as the template to prepare three types of RT-PCR products (Block1, Block2, and Block3), and these RT-PCR products were digested with EcoRI-ScaI, ScaI-BstXI, and BstXI-NotI, respectively, and the resulting three fragments were ligated and cloned into the EcoRI-NotI site of an expression vector. Block1 was obtained by PCR using a primer set of oligonucleotides of SEQ ID NOS: 25 and 26 (a cycle of a reaction at 98° C. for 10 seconds and a reaction at 68° C. for 1 minute was repeated 30 times). Block2 was obtained by PCR using a primer set of oligonucleotides of SEQ ID NOS: 27 and 28 (a cycle of a reaction at 98° C. for 10 seconds and a reaction at 68° C. for 1 minute was repeated 30 times). Block3 was obtained by carrying out PCR using a primer set of oligonucleotides of SEQ ID NOS: 29 and 30 (a cycle of a reaction at 94° C. for 15 seconds, a reaction at 60° C. for 15 seconds, and a reaction at 68° C. for 30 seconds was repeated 38 times), ligating an EcoRI-NotI-BamHI adaptor (Takara Bio) to both ends of the amplified product, inserting the ligation product into the EcoRI site of a plasmid vector, and digesting the resulting plasmid with BstXI-NotI. As a result, a polynucleotide consisting of a nucleotide sequence from the initiation codon ATG to exon 8 of the TPM3 gene and a nucleotide sequence from exon 35 to the stop codon of exon 43 of the ROS1 gene (TPM3ex8-ROS1ex35, SEQ ID NO: 15) was obtained. The polynucleotides obtained in this Example were novel.

Example 4

Examination of Oncogenic Potential of ROS1 Fusion Polypeptides

Figure 9:
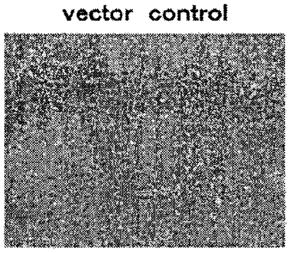
FIG. 9 is a micrograph, in place of drawings, showing the state of 3T3 fibroblasts which had been cultivated for 14 days after the introduction of an empty vector (pMXS).
Figure 10:
FIG. 10 is a micrograph, in place of drawings, showing the state of a nude mouse after 14 to 21 days from the subcutaneous inoculation with 3T3 fibroblast into which fusion gene SDC4ex2-ROS1ex32 (SEQ ID NO: 1) was transfected.
Figure 11:
FIG. 11 is a micrograph, in place of drawings, showing the state of a nude mouse after 14 to 21 days from the subcutaneous inoculation with 3T3 fibroblast into which fusion gene SDC4ex4-ROS1ex32 (SEQ ID NO: 3) was transfected.
Figure 12:
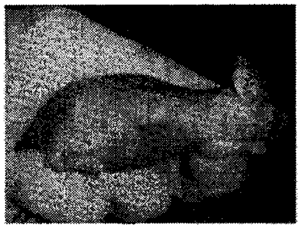
FIG. 12 is a micrograph, in place of drawings, showing the state of a nude mouse after 14 to 21 days from the subcutaneous inoculation with 3T3 fibroblast into which fusion gene SDC4ex4-ROS1ex34 (SEQ ID NO: 5) was transfected.
Figure 13:
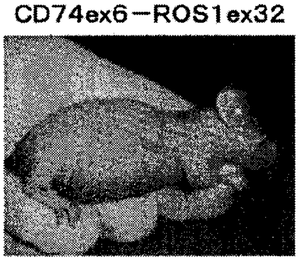
FIG. 13 is a micrograph, in place of drawings, showing the state of a nude mouse after 14 to 21 days from the subcutaneous inoculation with 3T3 fibroblast into which fusion gene CD74ex6-ROS1ex32 (SEQ ID NO: 7) was transfected.
Figure 14:
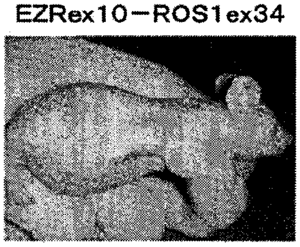
FIG. 14 is a micrograph, in place of drawings, showing the state of a nude mouse after 14 to 21 days from the subcutaneous inoculation with 3T3 fibroblast into which fusion gene EZRex10-ROS1ex34 (SEQ ID NO: 9) was transfected.
Figure 15:
FIG. 15 is a micrograph, in place of drawings, showing the state of a nude mouse after 14 to 21 days from the subcutaneous inoculation with 3T3 fibroblast into which fusion gene SLC34A2ex13-ROS1ex32 (SEQ ID NO: 11) was transfected.
Figure 16:
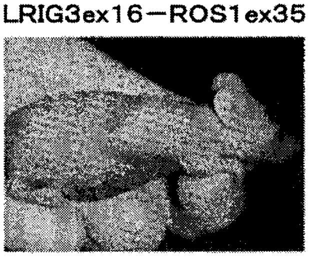
FIG. 16 is a micrograph, in place of drawings, showing the state of a nude mouse after 14 to 21 days from the subcutaneous inoculation with 3T3 fibroblast into which fusion gene LRIG3ex16-ROS1ex35 (SEQ ID NO: 13) was transfected.
Figure 17:
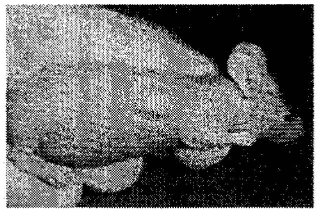
FIG. 17 is a micrograph, in place of drawings, showing the state of a nude mouse after 14 to 21 days from the subcutaneous inoculation with 3T3 fibroblast into which fusion gene TPM3ex8-ROS1ex35 (SEQ ID NO: 15) was transfected.

Each insert was collected from the plasmids constructed in Example 3 by digestion with restriction enzymes EcoRI and SalI, and subcloned into the EcoRI-SalI site of expression vector pMXS (JBC 275, 24945-24952, 2000). As described in Example 3, TPM3-ROS1 was inserted into the EcoRI-NotI site. The resulting plasmids expressing each fusion polypeptide or an empty vector without cDNA insertion (pMXS) was transfected into 3T3 fibroblasts by the calcium phosphate method, and cultivated for 14 days. As shown in FIGS. 1 to 8 (ROS1 fusion polypeptide expressed) and FIG. 9 (empty vector), transformed foci were observed only in the case that each vector expressing a fusion polypeptide was transfected.

Figure 18:
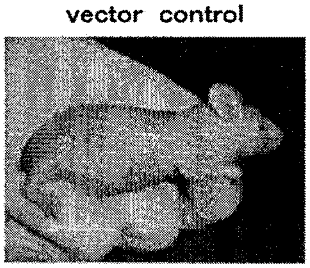
FIG. 18 is a micrograph, in place of drawings, showing the state of a nude mouse after 14 to 21 days from the subcutaneous inoculation with 3T3 fibroblast into which an empty vector (pMXS) was transfected.

Nude mice were subcutaneously inoculated with 3T3 cells ($5\times10^6$ cells per mouse) into which each vector expressing a fusion polypeptide or the empty vector had been transfected, and were observed for 14 to 21 days. After 14 days or later, tumor formation was observed in the mice inoculated with 3T3 cells into which each vector expressing a fusion polypeptide had been transfected (FIGS. 10 to 17). No tumor formation was observed in the mice inoculated with 3T3 cells into which the empty vector had been transfected (FIG. 18). It was shown from these results that each (SDC4, CD74, EZR, SLC34A2, LRIG3, or TPM3)-ROS1 fusion polypeptide exhibited oncogenic potential, and therefore, each (SDC4, CD74, EZR, SLC34A2, LRIG3, or TPM3)-ROS1 fusion polynucleotide was a causative gene for cancer.

Example 5

Detection of Fusion Genes

Each fusion gene was detected, by RT-PCR capable of directly amplifying a region containing each fusion site, to show that each fusion gene cDNA was present in cancer tissues. With respect to the following RNA templates derived from each specimen, a PCR consisting of a pretreatment reaction at 94° C. for 10 minutes, an amplification reaction under the following cycle conditions, and an elongation reaction at 72° C. for 10 minutes was carried out, using a forward primer (designed on each identified gene fused to the ROS1 gene) and a reverse primer designed on the ROS1 gene:

for #7130, #8701, and #26356 (SDC4-ROS1), a forward primer of SEQ ID NO: 34 and a reverse primer of SEQ ID NO: 31 were used, and a cycle of a reaction at 94° C. for 1 minute, a reaction at 70° C. for 1 minute, and a reaction at 72° C. for 30 seconds was repeated 30 times;

for #6534, #148, and #10855 (CD74-ROS1), a forward primer of SEQ ID NO: 35 and a reverse primer of SEQ ID NO: 31 were used, and a cycle of a reaction at 94° C. for 1 minute, a reaction at 70° C. for 1 minute, and a reaction at 72° C. for 30 seconds was repeated 30 times;

for #11994 and #9604 (EZR-ROS1), a forward primer of SEQ ID NO: 36 and a reverse primer of SEQ ID NO: 33 were used, and a cycle of a reaction at 94° C. for 1 minute, a reaction at 70° C. for 1 minute, and a reaction at 72° C. for 30 seconds was repeated 30 times;

for #10286 (SLC34A2-ROS1), a forward primer of SEQ ID NO: 37 and a reverse primer of SEQ ID NO: 31 were used, and a cycle of a reaction at 94° C. for 1 minute, a reaction at 68° C. for 1 minute, and a reaction at 72° C. for 60 seconds was repeated 35 times;

for #20130 (LRIG3-ROS1), a forward primer of SEQ ID NO: 38 and a reverse primer of SEQ ID NO: 32 were used, and a cycle of a reaction at 94° C. for 1 minute, a reaction at 68° C. for 1 minute, and a reaction at 72° C. for 10 seconds was repeated 35 times; and for #17970 and #8405 (TPM3-ROS1), a forward primer of SEQ ID NO: 39 and a reverse primer of SEQ ID NO: 31 were used, and a cycle of a reaction at 94° C. for 1 minute, a reaction at 70° C. for 1 minute, and a reaction at 72° C. for 30 seconds was repeated 30 times.

The resulting amplified products were subjected to electrophoresis, and bands of expected sizes from the setting position for each probe were observed in each gene, and as a result, it was shown that each fusion gene can be detected using a clinical specimen by designing primers on each gene.

Example 6

Detection of ROS1 Fusion Genes by FISH Method in Clinical Specimens

To confirm that each fusion gene was fused on the genome, fusion assay was carried out by a FISH method in accordance with Example 1, using the following probes:

BAC clone (RP1-179P9) for the ROS1 gene;

BAC clone (RP3-453C12) for the SDC4 gene;

BAC clone (RP11-1120I24) for the CD74 gene;

BAC clone (RP11-507C10) for the EZR gene;

BAC clone (RP11-752I1) for the SLC34A2 gene;

BAC clone (RP11-557F20) for the LRIG3 gene; and

BAC clone (RP11-205-M9) for the TPM3 gene.

The probe for the ROS1 gene was labeled with FITC (green), and the probes for the other genes were labeled with Texas Red (red).

In fusion assay, two gene regions of interest which are adjacent to each other by chromosomal translocation are stained with probes labeled with different fluorescent dyes. For example, when fluorescent labeling is carried out using two probes labeled with Texas Red (red) and FITC (green), the normal state is detected as distinct red and green signals (a state where the green signal and the red signal are present apart from each other), and a state where the two gene regions are adjacent to each other by translocation or inversion is detected as a yellow signal due to the overlap of the green and red signals. As a result of the fusion assay on the pathological sections positive for each fusion gene in Example 5, a signal (yellow) adjacent to the 3' region of the ROS1 gene was observed, and it was confirmed that each fusion gene was generated by translocation.

It was found that this method can be used as a method of detecting the fusion genes.

As described above, it was found in the present invention that fusion genes with the ROS1 gene were present in some of lung cancer patients, and these genes were causative of cancer. That is to say, it was found that cancer patients that are subject to a treatment with ROS1 inhibitors can be selected by detecting the ROS1 fusion genes, SDC4ex2-ROS1ex32, SDC4ex4-ROS1ex32, SDC4ex4-ROS1ex34, CD74ex6-ROS1ex32, EZRex10-ROS1ex34, SLC34A2ex13-ROS1ex32, LRIG3ex16-ROS1ex35, and TPM3ex8-ROS1ex35.

INDUSTRIAL APPLICABILITY

The detection method of the present invention is useful in the determination of whether cancer patients are positive for the fusion genes disclosed in the present specification. The detection kit and the primer set of the present invention can be used for the detection method.

Although the present invention has been described with reference to specific embodiments, various changes and modifications obvious to those skilled in the art are possible without departing from the scope of the appended claims.

FREE TEXT IN SEQUENCE LISTING

The nucleotide sequence of SEQ ID NO: 25 in the sequence listing is an artificially synthesized primer sequence.

---

The invention claimed is:

1. A method of detecting a fusion gene comprising a ROS1 kinase region, or a fusion protein encoded by the fusion gene, comprising:

detecting the presence of a polynucleotide encoding a polypeptide which is a fusion protein of SDC4 with ROS1, or the presence of the polypeptide, in a specimen obtained from a subject, wherein when a primer set is used for detecting the presence of the polynucleotide, each primer has a chain length of at least 15 nucleotides.

2. A method of detecting a fusion gene comprising a ROS1 kinase region, or a fusion protein encoded by the fusion gene, comprising:

detecting the presence of a polynucleotide encoding a polypeptide, or the presence of the polypeptide, in a specimen obtained from a subject, wherein the polypeptide is:

a polypeptide comprising an amino acid sequence that is at least 95% identical to an amino acid sequence selected from the group consisting of SEQ ID NOS: 2, 4, and 6, and wherein when a primer set is used for detecting the presence of the polynucleotide, each primer has a chain length of at least 15 nucleotides.

3. The method according to claim 2, wherein the polypeptide is a polypeptide comprises an amino acid sequence selected from the group consisting of SEQ ID NOS: 2, 4, and 6.

4. The method of detecting a fusion gene according to claim 1, comprising:

detecting the presence of a polynucleotide encoding the polypeptide in a specimen obtained from a subject.

5. A kit for detecting a fusion gene comprising a ROS1 kinase region, comprising a sense primer and an antisense primer, wherein the sense primer and the antisense primer are designed to be able to specifically amplify a polynucleotide encoding a polypeptide wherein the polypeptide is a fusion protein of SDC4 with ROS1, and wherein each primer has a chain length of at least 15 nucleotides.

6. A kit for detecting a fusion gene comprising a ROS1 kinase region, comprising a sense primer and an antisense primer which are designed to be able to specifically amplify a polynucleotide encoding a polypeptide, wherein the polypeptide is:

a polypeptide comprising an amino acid sequence that is at least 95% identical to an amino acid sequence selected from the group consisting of SEQ ID NOS: 2, 4, and 6, and wherein each primer has a chain length of at least 15 nucleotides.

7. The kit according to claim 6, wherein the polypeptide is:

a polypeptide comprising an amino acid sequence selected from the group consisting of SEQ ID NOS: 2, 4, and 6.

8. A primer set for detecting a fusion gene of an SDC4 gene with a ROS1 gene, comprising a sense primer designed based on a portion encoding SDC4, and an antisense primer designed based on a portion encoding ROS1, wherein the antisense primer consists of a nucleic acid molecule hybridizing under stringent conditions to the polynucleotide described in claim 1, and the sense primer consists of a nucleic acid molecule hybridizing under stringent conditions to a strand complementary to the polynucleotide described in claim 1, and wherein each primer has a chain length of at least 15 nucleotides.

9. A primer set for detecting a fusion gene of an SDC4 gene with a ROS1 gene, selected from the group consisting of:

a) a primer set comprising an antisense primer and a sense primer, wherein the antisense primer consists of a nucleic acid molecule hybridizing under stringent conditions to a polynucleotide consisting of the nucleotide sequence of SEQ ID NO: 1, and the sense primer consists of a nucleic acid molecule hybridizing under stringent conditions to a strand complementary to the polynucleotide, b) a primer set comprising an antisense primer and a sense primer, wherein the antisense primer consists of a nucleic acid molecule hybridizing under stringent conditions to a polynucleotide consisting of the nucleotide sequence of SEQ ID NO: 3, and the sense primer consists of a nucleic acid molecule hybridizing under stringent conditions to a strand complementary to the polynucleotide, and c) a primer set comprising an antisense primer and a sense primer, wherein the antisense primer consists of a nucleic acid molecule hybridizing under stringent conditions to a polynucleotide consisting of the nucleotide sequence of SEQ ID NO: 5, and the sense primer consists of a nucleic acid molecule hybridizing under stringent conditions to a strand complementary to the polynucleotide wherein each primer has a chain length of at least 15 nucleotides.

10. A primer set of a sense primer which is an oligonucleotide consisting of at least 16 consecutive nucleotides in the region of nucleotides 1-199 of SEQ ID NO: 1, and an antisense primer which is an oligonucleotide complementary to at least 16 consecutive nucleotides in the region of nucleotides 200-1995 of SEQ ID NO: 1.

11. A primer set of a sense primer which is an oligonucleotide consisting of at least 16 consecutive nucleotides in the region of nucleotides 1-445 of SEQ ID NO: 3, and an antisense primer which is an oligonucleotide complementary to at least 16 consecutive nucleotides in the region of nucleotides 446-2241 of SEQ ID NO: 3.

12. A primer set of a sense primer which is an oligonucleotide consisting of at least 16 consecutive nucleotides in the region of nucleotides 1-445 of SEQ ID NO: 5, and an antisense primer which is an oligonucleotide complementary to at least 16 consecutive nucleotides in the region of nucleotides 446-1932 of SEQ ID NO: 5.

13. The method of detecting a fusion gene according to claim 2, comprising:

detecting the presence of a polynucleotide encoding the polypeptide in a specimen obtained from a subject.

14. The method of detecting a fusion gene according to claim 3, comprising:

detecting the presence of a polynucleotide encoding the polypeptide in a specimen obtained from a subject.

15. A primer set for detecting a fusion gene of an SDC4 gene with a ROS1 gene, comprising a sense primer designed based on a portion encoding SDC4, and an antisense primer designed based on a portion encoding ROS1, wherein the antisense primer consists of a nucleic acid molecule hybridizing under stringent conditions to the polynucleotide described in claim 2, and the sense primer consists of a nucleic acid molecule hybridizing under stringent conditions to a strand complementary to the polynucleotide described in claim 2, and wherein each primer has a chain length of at least 15 nucleotides.

16. The method of claim 4, wherein the detection is carried out using a hybridization technique.

17. The method of claim 13, wherein the detection is carried out using a hybridization technique.

18. The method of claim 14, wherein the detection is carried out using a hybridization technique.

19. A kit for detecting a fusion gene comprising a ROS1 kinase region, comprising a first probe that specifically recognizes a 5' region of a ROS1 gene, and a second probe that specifically recognizes a 3' region of a ROS1 gene, wherein each probe has a chain length of at least 32 nucleotides, wherein at least one probe is labeled.

20. A kit for detecting a fusion gene of an SDC4 gene with a ROS1 gene, comprising a first probe that specifically recognizes a 5' region of the SDC4 gene, and a second probe that specifically recognizes a 3' region of the ROS1 gene, wherein each probe has a chain length of at least 32 nucleotides.

21. The kit according to claim 20, wherein at least one probe is labeled.

22. A probe for detecting a fusion gene of an SDC4 gene with a ROS1 gene, the probe comprising (i) a nucleotide sequence consisting of nucleotides selected from the group consisting of nucleotides 184-215 in the nucleotide sequence of SEQ ID NO: 1, nucleotides 430-461 in the nucleotide sequence of SEQ ID NO: 3, and nucleotides 430-461 (445/446) in the nucleotide sequence of SEQ ID NO: 5, or (ii) its complementary sequence, wherein the probe has a chain length of at least 32 nucleotides.

23. The method of claim 3, wherein the polypeptide is a polypeptide consisting of an amino acid sequence selected from the group consisting of SEQ ID NOS: 2, 4, and 6.

24. The method of claim 7, wherein the polypeptide is a polypeptide consisting of an amino acid sequence selected from the group consisting of SEQ ID NOS: 2, 4, and 6.

* * * * *

UNITED STATES PATENT AND TRADEMARK OFFICE

CERTIFICATE OF CORRECTION

PATENT NO. : 9,109,259 B2
APPLICATION NO. : 13/805513
DATED : August 18, 2015
INVENTOR(S) : Kengo Takeuchi et al.

It is certified that error appears in the above-identified patent and that said Letters Patent is hereby corrected as shown below:

On the title page, Item (73), the Assignees' Information is incorrect. Item (73) should read:

--(73) Assignees: Japanese Foundation for Cancer Research, Tokyo (JP);

Educational Foundation Jichi Medical University, Shimotsuke-shi (JP);

LSI Medience Corporation, Tokyo (JP)--

Signed and Sealed this
Twenty-ninth Day of March, 2016

Michelle K. Lee
*Director of the United States Patent and Trademark Office*

SEQUENCE LISTING

```
<160> NUMBER OF SEQ ID NOS: 39

<210> SEQ ID NO 1
<211> LENGTH: 1995
<212> TYPE: DNA
```

-continued

```
<213> ORGANISM: Homo sapiens
<220> FEATURE:
<221> NAME/KEY: CDS
<222> LOCATION: (1)..(1995)

<400> SEQUENCE: 1

atg gcc ccc gcc cgt ctg ttc gcg ctg ctg ctg ctc ttc gta ggc gga       48
Met Ala Pro Ala Arg Leu Phe Ala Leu Leu Leu Leu Phe Val Gly Gly
1               5                   10                  15

gtc gcc gag tcg atc cga gag act gag gtc atc gac ccc cag gac ctc       96
Val Ala Glu Ser Ile Arg Glu Thr Glu Val Ile Asp Pro Gln Asp Leu
            20                  25                  30

cta gaa ggc cga tac ttc tcc gga gcc cta cca gac gat gag gat gta      144
Leu Glu Gly Arg Tyr Phe Ser Gly Ala Leu Pro Asp Asp Glu Asp Val
        35                  40                  45

gtg ggg ccc ggg cag gaa tct gat gac ttt gag ctg tct ggc tct gga      192
Val Gly Pro Gly Gln Glu Ser Asp Asp Phe Glu Leu Ser Gly Ser Gly
    50                  55                  60

gat ctg gct gga gtc cca aat aaa cca ggc att ccc aaa tta cta gaa      240
Asp Leu Ala Gly Val Pro Asn Lys Pro Gly Ile Pro Lys Leu Leu Glu
65                  70                  75                  80

ggg agt aaa aat tca ata cag tgg gag aaa gct gaa gat aat gga tgt      288
Gly Ser Lys Asn Ser Ile Gln Trp Glu Lys Ala Glu Asp Asn Gly Cys
                85                  90                  95

aga att aca tac tat atc ctt gag ata aga aag agc act tca aat aat      336
Arg Ile Thr Tyr Tyr Ile Leu Glu Ile Arg Lys Ser Thr Ser Asn Asn
            100                 105                 110

tta cag aac cag aat tta agg tgg aag atg aca ttt aat gga tcc tgc      384
Leu Gln Asn Gln Asn Leu Arg Trp Lys Met Thr Phe Asn Gly Ser Cys
        115                 120                 125

agt agt gtt tgc aca tgg aag tcc aaa aac ctg aaa gga ata ttt cag      432
Ser Ser Val Cys Thr Trp Lys Ser Lys Asn Leu Lys Gly Ile Phe Gln
    130                 135                 140

ttc aga gta gta gct gca aat aat cta ggg ttt ggt gaa tat agt gga      480
Phe Arg Val Val Ala Ala Asn Asn Leu Gly Phe Gly Glu Tyr Ser Gly
145                 150                 155                 160

atc agt gag aat att ata tta gtt gga gat gat ttt tgg ata cca gaa      528
Ile Ser Glu Asn Ile Ile Leu Val Gly Asp Asp Phe Trp Ile Pro Glu
                165                 170                 175

aca agt ttc ata ctt act att ata gtt gga ata ttt ctg gtt gtt aca      576
Thr Ser Phe Ile Leu Thr Ile Ile Val Gly Ile Phe Leu Val Val Thr
            180                 185                 190

atc cca ctg acc ttt gtc tgg cat aga aga tta aag aat caa aaa agt      624
Ile Pro Leu Thr Phe Val Trp His Arg Arg Leu Lys Asn Gln Lys Ser
        195                 200                 205

gcc aag gaa ggg gtg aca gtg ctt ata aac gaa gac aaa gag ttg gct      672
Ala Lys Glu Gly Val Thr Val Leu Ile Asn Glu Asp Lys Glu Leu Ala
    210                 215                 220

gag ctg cga ggt ctg gca gcc gga gta ggc ctg gct aat gcc tgc tat      720
Glu Leu Arg Gly Leu Ala Ala Gly Val Gly Leu Ala Asn Ala Cys Tyr
225                 230                 235                 240

gca ata cat act ctt cca acc caa gag gag att gaa aat ctt cct gcc      768
Ala Ile His Thr Leu Pro Thr Gln Glu Glu Ile Glu Asn Leu Pro Ala
                245                 250                 255

ttc cct cgg gaa aaa ctg act ctg cgt ctc ttg ctg gga agt gga gcc      816
Phe Pro Arg Glu Lys Leu Thr Leu Arg Leu Leu Leu Gly Ser Gly Ala
            260                 265                 270

ttt gga gaa gtg tat gaa gga aca gca gtg gac atc tta gga gtt gga      864
Phe Gly Glu Val Tyr Glu Gly Thr Ala Val Asp Ile Leu Gly Val Gly
        275                 280                 285
```

-continued

```
agt gga gaa atc aaa gta gca gtg aag act ttg aag aag ggt tcc aca      912
Ser Gly Glu Ile Lys Val Ala Val Lys Thr Leu Lys Lys Gly Ser Thr
    290                 295                 300

gac cag gag aag att gaa ttc ctg aag gag gca cat ctg atg agc aaa      960
Asp Gln Glu Lys Ile Glu Phe Leu Lys Glu Ala His Leu Met Ser Lys
305                 310                 315                 320

ttt aat cat ccc aac att ctg aag cag ctt gga gtt tgt ctg ctg aat     1008
Phe Asn His Pro Asn Ile Leu Lys Gln Leu Gly Val Cys Leu Leu Asn
                325                 330                 335

gaa ccc caa tac att atc ctg gaa ctg atg gag gga gga gac ctt ctt     1056
Glu Pro Gln Tyr Ile Ile Leu Glu Leu Met Glu Gly Gly Asp Leu Leu
            340                 345                 350

act tat ttg cgt aaa gcc cgg atg gca acg ttt tat ggt cct tta ctc     1104
Thr Tyr Leu Arg Lys Ala Arg Met Ala Thr Phe Tyr Gly Pro Leu Leu
        355                 360                 365

acc ttg gtt gac ctt gta gac ctg tgt gta gat att tca aaa ggc tgt     1152
Thr Leu Val Asp Leu Val Asp Leu Cys Val Asp Ile Ser Lys Gly Cys
    370                 375                 380

gtc tac ttg gaa cgg atg cat ttc att cac agg gat ctg gca gct aga     1200
Val Tyr Leu Glu Arg Met His Phe Ile His Arg Asp Leu Ala Ala Arg
385                 390                 395                 400

aat tgc ctt gtt tcc gtg aaa gac tat acc agt cca cgg ata gtg aag     1248
Asn Cys Leu Val Ser Val Lys Asp Tyr Thr Ser Pro Arg Ile Val Lys
                405                 410                 415

att gga gac ttt gga ctc gcc aga gac atc tat aaa aat gat tac tat     1296
Ile Gly Asp Phe Gly Leu Ala Arg Asp Ile Tyr Lys Asn Asp Tyr Tyr
            420                 425                 430

aga aag aga ggg gaa ggc ctg ctc cca gtt cgg tgg atg gct cca gaa     1344
Arg Lys Arg Gly Glu Gly Leu Leu Pro Val Arg Trp Met Ala Pro Glu
        435                 440                 445

agt ttg atg gat gga atc ttc act act caa tct gat gta tgg tct ttt     1392
Ser Leu Met Asp Gly Ile Phe Thr Thr Gln Ser Asp Val Trp Ser Phe
    450                 455                 460

gga att ctg att tgg gag att tta act ctt ggt cat cag cct tat cca     1440
Gly Ile Leu Ile Trp Glu Ile Leu Thr Leu Gly His Gln Pro Tyr Pro
465                 470                 475                 480

gct cat tcc aac ctt gat gtg tta aac tat gtg caa aca gga ggg aga     1488
Ala His Ser Asn Leu Asp Val Leu Asn Tyr Val Gln Thr Gly Gly Arg
                485                 490                 495

ctg gag cca cca aga aat tgt cct gat gat ctg tgg aat tta atg acc     1536
Leu Glu Pro Pro Arg Asn Cys Pro Asp Asp Leu Trp Asn Leu Met Thr
            500                 505                 510

cag tgc tgg gct caa gaa ccc gac caa aga cct act ttt cat aga att     1584
Gln Cys Trp Ala Gln Glu Pro Asp Gln Arg Pro Thr Phe His Arg Ile
        515                 520                 525

cag gac caa ctt cag tta ttc aga aat ttt ttc tta aat agc att tat     1632
Gln Asp Gln Leu Gln Leu Phe Arg Asn Phe Phe Leu Asn Ser Ile Tyr
    530                 535                 540

aag tcc aga gat gaa gca aac aac agt gga gtc ata aat gaa agc ttt     1680
Lys Ser Arg Asp Glu Ala Asn Asn Ser Gly Val Ile Asn Glu Ser Phe
545                 550                 555                 560

gaa ggt gaa gat ggc gat gtg att tgt ttg aat tca gat gac att atg     1728
Glu Gly Glu Asp Gly Asp Val Ile Cys Leu Asn Ser Asp Asp Ile Met
                565                 570                 575

cca gtt gct tta atg gaa acg aag aac cga gaa ggg tta aac tat atg     1776
Pro Val Ala Leu Met Glu Thr Lys Asn Arg Glu Gly Leu Asn Tyr Met
            580                 585                 590

gta ctt gct aca gaa tgt ggc caa ggt gaa gaa aag tct gag ggt cct     1824
Val Leu Ala Thr Glu Cys Gly Gln Gly Glu Glu Lys Ser Glu Gly Pro
        595                 600                 605
```

```
cta ggc tcc cag gaa tct gaa tct tgt ggt ctg agg aaa gaa gag aag      1872
Leu Gly Ser Gln Glu Ser Glu Ser Cys Gly Leu Arg Lys Glu Glu Lys
    610                 615                 620

gaa cca cat gca gac aaa gat ttc tgc caa gaa aaa caa gtg gct tac      1920
Glu Pro His Ala Asp Lys Asp Phe Cys Gln Glu Lys Gln Val Ala Tyr
625                 630                 635                 640

tgc cct tct ggc aag cct gaa ggc ctg aac tat gcc tgt ctc act cac      1968
Cys Pro Ser Gly Lys Pro Glu Gly Leu Asn Tyr Ala Cys Leu Thr His
                645                 650                 655

agt gga tat gga gat ggg tct gat taa                                  1995
Ser Gly Tyr Gly Asp Gly Ser Asp
            660


<210> SEQ ID NO 2
<211> LENGTH: 664
<212> TYPE: PRT
<213> ORGANISM: Homo sapiens

<400> SEQUENCE: 2

Met Ala Pro Ala Arg Leu Phe Ala Leu Leu Leu Leu Phe Val Gly Gly
1               5                   10                  15

Val Ala Glu Ser Ile Arg Glu Thr Glu Val Ile Asp Pro Gln Asp Leu
            20                  25                  30

Leu Glu Gly Arg Tyr Phe Ser Gly Ala Leu Pro Asp Asp Glu Asp Val
        35                  40                  45

Val Gly Pro Gly Gln Glu Ser Asp Asp Phe Glu Leu Ser Gly Ser Gly
    50                  55                  60

Asp Leu Ala Gly Val Pro Asn Lys Pro Gly Ile Pro Lys Leu Leu Glu
65                  70                  75                  80

Gly Ser Lys Asn Ser Ile Gln Trp Glu Lys Ala Glu Asp Asn Gly Cys
                85                  90                  95

Arg Ile Thr Tyr Tyr Ile Leu Glu Ile Arg Lys Ser Thr Ser Asn Asn
            100                 105                 110

Leu Gln Asn Gln Asn Leu Arg Trp Lys Met Thr Phe Asn Gly Ser Cys
        115                 120                 125

Ser Ser Val Cys Thr Trp Lys Ser Lys Asn Leu Lys Gly Ile Phe Gln
    130                 135                 140

Phe Arg Val Val Ala Ala Asn Asn Leu Gly Phe Gly Glu Tyr Ser Gly
145                 150                 155                 160

Ile Ser Glu Asn Ile Ile Leu Val Gly Asp Asp Phe Trp Ile Pro Glu
                165                 170                 175

Thr Ser Phe Ile Leu Thr Ile Ile Val Gly Ile Phe Leu Val Val Thr
            180                 185                 190

Ile Pro Leu Thr Phe Val Trp His Arg Arg Leu Lys Asn Gln Lys Ser
        195                 200                 205

Ala Lys Glu Gly Val Thr Val Leu Ile Asn Glu Asp Lys Glu Leu Ala
    210                 215                 220

Glu Leu Arg Gly Leu Ala Ala Gly Val Gly Leu Ala Asn Ala Cys Tyr
225                 230                 235                 240

Ala Ile His Thr Leu Pro Thr Gln Glu Glu Ile Glu Asn Leu Pro Ala
                245                 250                 255

Phe Pro Arg Glu Lys Leu Thr Leu Arg Leu Leu Leu Gly Ser Gly Ala
            260                 265                 270

Phe Gly Glu Val Tyr Glu Gly Thr Ala Val Asp Ile Leu Gly Val Gly
        275                 280                 285
```

-continued

```
Ser Gly Glu Ile Lys Val Ala Val Lys Thr Leu Lys Lys Gly Ser Thr
    290                 295                 300

Asp Gln Glu Lys Ile Glu Phe Leu Lys Glu Ala His Leu Met Ser Lys
305                 310                 315                 320

Phe Asn His Pro Asn Ile Leu Lys Gln Leu Gly Val Cys Leu Leu Asn
                325                 330                 335

Glu Pro Gln Tyr Ile Ile Leu Glu Leu Met Glu Gly Gly Asp Leu Leu
            340                 345                 350

Thr Tyr Leu Arg Lys Ala Arg Met Ala Thr Phe Tyr Gly Pro Leu Leu
        355                 360                 365

Thr Leu Val Asp Leu Val Asp Leu Cys Val Asp Ile Ser Lys Gly Cys
    370                 375                 380

Val Tyr Leu Glu Arg Met His Phe Ile His Arg Asp Leu Ala Ala Arg
385                 390                 395                 400

Asn Cys Leu Val Ser Val Lys Asp Tyr Thr Ser Pro Arg Ile Val Lys
                405                 410                 415

Ile Gly Asp Phe Gly Leu Ala Arg Asp Ile Tyr Lys Asn Asp Tyr Tyr
            420                 425                 430

Arg Lys Arg Gly Glu Gly Leu Leu Pro Val Arg Trp Met Ala Pro Glu
        435                 440                 445

Ser Leu Met Asp Gly Ile Phe Thr Thr Gln Ser Asp Val Trp Ser Phe
    450                 455                 460

Gly Ile Leu Ile Trp Glu Ile Leu Thr Leu Gly His Gln Pro Tyr Pro
465                 470                 475                 480

Ala His Ser Asn Leu Asp Val Leu Asn Tyr Val Gln Thr Gly Gly Arg
                485                 490                 495

Leu Glu Pro Pro Arg Asn Cys Pro Asp Asp Leu Trp Asn Leu Met Thr
            500                 505                 510

Gln Cys Trp Ala Gln Glu Pro Asp Gln Arg Pro Thr Phe His Arg Ile
        515                 520                 525

Gln Asp Gln Leu Gln Leu Phe Arg Asn Phe Phe Leu Asn Ser Ile Tyr
    530                 535                 540

Lys Ser Arg Asp Glu Ala Asn Asn Ser Gly Val Ile Asn Glu Ser Phe
545                 550                 555                 560

Glu Gly Glu Asp Gly Asp Val Ile Cys Leu Asn Ser Asp Asp Ile Met
                565                 570                 575

Pro Val Ala Leu Met Glu Thr Lys Asn Arg Glu Gly Leu Asn Tyr Met
            580                 585                 590

Val Leu Ala Thr Glu Cys Gly Gln Gly Glu Glu Lys Ser Glu Gly Pro
        595                 600                 605

Leu Gly Ser Gln Glu Ser Glu Ser Cys Gly Leu Arg Lys Glu Glu Lys
    610                 615                 620

Glu Pro His Ala Asp Lys Asp Phe Cys Gln Glu Lys Gln Val Ala Tyr
625                 630                 635                 640

Cys Pro Ser Gly Lys Pro Glu Gly Leu Asn Tyr Ala Cys Leu Thr His
                645                 650                 655

Ser Gly Tyr Gly Asp Gly Ser Asp
            660
```

<210> SEQ ID NO 3
<211> LENGTH: 2241
<212> TYPE: DNA
<213> ORGANISM: Homo sapiens
<220> FEATURE:
<221> NAME/KEY: CDS -continued

<222> LOCATION: (1)..(2241)

<400> SEQUENCE: 3

```
atg gcc ccc gcc cgt ctg ttc gcg ctg ctg ctg ttc ttc gta ggc gga       48
Met Ala Pro Ala Arg Leu Phe Ala Leu Leu Leu Phe Phe Val Gly Gly
1               5                   10                  15

gtc gcc gag tcg atc cga gag act gag gtc atc gac ccc cag gac ctc       96
Val Ala Glu Ser Ile Arg Glu Thr Glu Val Ile Asp Pro Gln Asp Leu
            20                  25                  30

cta gaa ggc cga tac ttc tcc gga gcc cta cca gac gat gag gat gta      144
Leu Glu Gly Arg Tyr Phe Ser Gly Ala Leu Pro Asp Asp Glu Asp Val
        35                  40                  45

gtg ggg ccc ggg cag gaa tct gat gac ttt gag ctg tct ggc tct gga      192
Val Gly Pro Gly Gln Glu Ser Asp Asp Phe Glu Leu Ser Gly Ser Gly
    50                  55                  60

gat ctg gat gac ttg gaa gac tcc atg atc ggc cct gaa gtt gtc cat      240
Asp Leu Asp Asp Leu Glu Asp Ser Met Ile Gly Pro Glu Val Val His
65                  70                  75                  80

ccc ttg gtg cct cta gat aac cat atc cct gag agg gca ggg tct ggg      288
Pro Leu Val Pro Leu Asp Asn His Ile Pro Glu Arg Ala Gly Ser Gly
                85                  90                  95

agc caa gtc ccc acc gaa ccc aag aaa cta gag gag aat gag gtt atc      336
Ser Gln Val Pro Thr Glu Pro Lys Lys Leu Glu Glu Asn Glu Val Ile
            100                 105                 110

ccc aag aga atc tca ccc gtt gaa gag agt gag gat gtg tcc aac aag      384
Pro Lys Arg Ile Ser Pro Val Glu Glu Ser Glu Asp Val Ser Asn Lys
        115                 120                 125

gtg tca atg tcc agc act gtg cag ggc agc aac atc ttt gag aga acg      432
Val Ser Met Ser Ser Thr Val Gln Gly Ser Asn Ile Phe Glu Arg Thr
    130                 135                 140

gag gtc ctg gca gct gga gtc cca aat aaa cca ggc att ccc aaa tta      480
Glu Val Leu Ala Ala Gly Val Pro Asn Lys Pro Gly Ile Pro Lys Leu
145                 150                 155                 160

cta gaa ggg agt aaa aat tca ata cag tgg gag aaa gct gaa gat aat      528
Leu Glu Gly Ser Lys Asn Ser Ile Gln Trp Glu Lys Ala Glu Asp Asn
                165                 170                 175

gga tgt aga att aca tac tat atc ctt gag ata aga aag agc act tca      576
Gly Cys Arg Ile Thr Tyr Tyr Ile Leu Glu Ile Arg Lys Ser Thr Ser
            180                 185                 190

aat aat tta cag aac cag aat tta agg tgg aag atg aca ttt aat gga      624
Asn Asn Leu Gln Asn Gln Asn Leu Arg Trp Lys Met Thr Phe Asn Gly
        195                 200                 205

tcc tgc agt agt gtt tgc aca tgg aag tcc aaa aac ctg aaa gga ata      672
Ser Cys Ser Ser Val Cys Thr Trp Lys Ser Lys Asn Leu Lys Gly Ile
    210                 215                 220

ttt cag ttc aga gta gta gct gca aat aat cta ggg ttt ggt gaa tat      720
Phe Gln Phe Arg Val Val Ala Ala Asn Asn Leu Gly Phe Gly Glu Tyr
225                 230                 235                 240

agt gga atc agt gag aat att ata tta gtt gga gat gat ttt tgg ata      768
Ser Gly Ile Ser Glu Asn Ile Ile Leu Val Gly Asp Asp Phe Trp Ile
                245                 250                 255

cca gaa aca agt ttc ata ctt act att ata gtt gga ata ttt ctg gtt      816
Pro Glu Thr Ser Phe Ile Leu Thr Ile Ile Val Gly Ile Phe Leu Val
            260                 265                 270

gtt aca atc cca ctg acc ttt gtc tgg cat aga aga tta aag aat caa      864
Val Thr Ile Pro Leu Thr Phe Val Trp His Arg Arg Leu Lys Asn Gln
        275                 280                 285

aaa agt gcc aag gaa ggg gtg aca gtg ctt ata aac gaa gac aaa gag      912
Lys Ser Ala Lys Glu Gly Val Thr Val Leu Ile Asn Glu Asp Lys Glu
    290                 295                 300
```

-continued

```
ttg gct gag ctg cga ggt ctg gca gcc gga gta ggc ctg gct aat gcc      960
Leu Ala Glu Leu Arg Gly Leu Ala Ala Gly Val Gly Leu Ala Asn Ala
305                 310                 315                 320

tgc tat gca ata cat act ctt cca acc caa gag gag att gaa aat ctt     1008
Cys Tyr Ala Ile His Thr Leu Pro Thr Gln Glu Glu Ile Glu Asn Leu
                325                 330                 335

cct gcc ttc cct cgg gaa aaa ctg act ctg cgt ctc ttg ctg gga agt     1056
Pro Ala Phe Pro Arg Glu Lys Leu Thr Leu Arg Leu Leu Leu Gly Ser
            340                 345                 350

gga gcc ttt gga gaa gtg tat gaa gga aca gca gtg gac atc tta gga     1104
Gly Ala Phe Gly Glu Val Tyr Glu Gly Thr Ala Val Asp Ile Leu Gly
        355                 360                 365

gtt gga agt gga gaa atc aaa gta gca gtg aag act ttg aag aag ggt     1152
Val Gly Ser Gly Glu Ile Lys Val Ala Val Lys Thr Leu Lys Lys Gly
    370                 375                 380

tcc aca gac cag gag aag att gaa ttc ctg aag gag gca cat ctg atg     1200
Ser Thr Asp Gln Glu Lys Ile Glu Phe Leu Lys Glu Ala His Leu Met
385                 390                 395                 400

agc aaa ttt aat cat ccc aac att ctg aag cag ctt gga gtt tgt ctg     1248
Ser Lys Phe Asn His Pro Asn Ile Leu Lys Gln Leu Gly Val Cys Leu
                405                 410                 415

ctg aat gaa ccc caa tac att atc ctg gaa ctg atg gag gga gga gac     1296
Leu Asn Glu Pro Gln Tyr Ile Ile Leu Glu Leu Met Glu Gly Gly Asp
            420                 425                 430

ctt ctt act tat ttg cgt aaa gcc cgg atg gca acg ttt tat ggt cct     1344
Leu Leu Thr Tyr Leu Arg Lys Ala Arg Met Ala Thr Phe Tyr Gly Pro
        435                 440                 445

tta ctc acc ttg gtt gac ctt gta gac ctg tgt gta gat att tca aaa     1392
Leu Leu Thr Leu Val Asp Leu Val Asp Leu Cys Val Asp Ile Ser Lys
    450                 455                 460

ggc tgt gtc tac ttg gaa cgg atg cat ttc att cac agg gat ctg gca     1440
Gly Cys Val Tyr Leu Glu Arg Met His Phe Ile His Arg Asp Leu Ala
465                 470                 475                 480

gct aga aat tgc ctt gtt tcc gtg aaa gac tat acc agt cca cgg ata     1488
Ala Arg Asn Cys Leu Val Ser Val Lys Asp Tyr Thr Ser Pro Arg Ile
                485                 490                 495

gtg aag att gga gac ttt gga ctc gcc aga gac atc tat aaa aat gat     1536
Val Lys Ile Gly Asp Phe Gly Leu Ala Arg Asp Ile Tyr Lys Asn Asp
            500                 505                 510

tac tat aga aag aga ggg gaa ggc ctg ctc cca gtt cgg tgg atg gct     1584
Tyr Tyr Arg Lys Arg Gly Glu Gly Leu Leu Pro Val Arg Trp Met Ala
        515                 520                 525

cca gaa agt ttg atg gat gga atc ttc act act caa tct gat gta tgg     1632
Pro Glu Ser Leu Met Asp Gly Ile Phe Thr Thr Gln Ser Asp Val Trp
    530                 535                 540

tct ttt gga att ctg att tgg gag att tta act ctt ggt cat cag cct     1680
Ser Phe Gly Ile Leu Ile Trp Glu Ile Leu Thr Leu Gly His Gln Pro
545                 550                 555                 560

tat cca gct cat tcc aac ctt gat gtg tta aac tat gtg caa aca gga     1728
Tyr Pro Ala His Ser Asn Leu Asp Val Leu Asn Tyr Val Gln Thr Gly
                565                 570                 575

ggg aga ctg gag cca cca aga aat tgt cct gat gat ctg tgg aat tta     1776
Gly Arg Leu Glu Pro Pro Arg Asn Cys Pro Asp Asp Leu Trp Asn Leu
            580                 585                 590

atg acc cag tgc tgg gct caa gaa ccc gac caa aga cct act ttt cat     1824
Met Thr Gln Cys Trp Ala Gln Glu Pro Asp Gln Arg Pro Thr Phe His
        595                 600                 605

aga att cag gac caa ctt cag tta ttc aga aat ttt ttc tta aat agc     1872
Arg Ile Gln Asp Gln Leu Gln Leu Phe Arg Asn Phe Phe Leu Asn Ser
```

-continued

```
    610                 615                 620

att tat aag tcc aga gat gaa gca aac aac agt gga gtc ata aag gaa      1920
Ile Tyr Lys Ser Arg Asp Glu Ala Asn Asn Ser Gly Val Ile Lys Glu
625                 630                 635                 640

agc ttt gaa ggt gaa gat ggc gat gtg att tgt ttg aat tca gat gac      1968
Ser Phe Glu Gly Glu Asp Gly Asp Val Ile Cys Leu Asn Ser Asp Asp
                645                 650                 655

att atg cca gtt gct tta atg gaa acg aag aac cga gaa ggg tta aac      2016
Ile Met Pro Val Ala Leu Met Glu Thr Lys Asn Arg Glu Gly Leu Asn
            660                 665                 670

tat atg gta ctt gct aca gaa tgt ggc caa ggt gaa gaa aag tct gag      2064
Tyr Met Val Leu Ala Thr Glu Cys Gly Gln Gly Glu Glu Lys Ser Glu
        675                 680                 685

ggt cct cta ggc tcc cag gaa tct gaa tct tgt ggt ctg agg aaa gaa      2112
Gly Pro Leu Gly Ser Gln Glu Ser Glu Ser Cys Gly Leu Arg Lys Glu
    690                 695                 700

gag aag gaa cca cat gca gac aaa gat ttc tgc caa gaa aaa caa gtg      2160
Glu Lys Glu Pro His Ala Asp Lys Asp Phe Cys Gln Glu Lys Gln Val
705                 710                 715                 720

gct tac tgc cct tct ggc aag cct gaa ggc ctg aac tat gcc tgt ctc      2208
Ala Tyr Cys Pro Ser Gly Lys Pro Glu Gly Leu Asn Tyr Ala Cys Leu
                725                 730                 735

act cac agt gga tat gga gat ggg tct gat taa                          2241
Thr His Ser Gly Tyr Gly Asp Gly Ser Asp
            740                 745


<210> SEQ ID NO 4
<211> LENGTH: 746
<212> TYPE: PRT
<213> ORGANISM: Homo sapiens

<400> SEQUENCE: 4

Met Ala Pro Ala Arg Leu Phe Ala Leu Leu Leu Phe Phe Val Gly Gly
1               5                   10                  15

Val Ala Glu Ser Ile Arg Glu Thr Glu Val Ile Asp Pro Gln Asp Leu
            20                  25                  30

Leu Glu Gly Arg Tyr Phe Ser Gly Ala Leu Pro Asp Asp Glu Asp Val
        35                  40                  45

Val Gly Pro Gly Gln Glu Ser Asp Asp Phe Glu Leu Ser Gly Ser Gly
    50                  55                  60

Asp Leu Asp Asp Leu Glu Asp Ser Met Ile Gly Pro Glu Val Val His
65                  70                  75                  80

Pro Leu Val Pro Leu Asp Asn His Ile Pro Glu Arg Ala Gly Ser Gly
                85                  90                  95

Ser Gln Val Pro Thr Glu Pro Lys Lys Leu Glu Glu Asn Glu Val Ile
            100                 105                 110

Pro Lys Arg Ile Ser Pro Val Glu Glu Ser Glu Asp Val Ser Asn Lys
        115                 120                 125

Val Ser Met Ser Ser Thr Val Gln Gly Ser Asn Ile Phe Glu Arg Thr
    130                 135                 140

Glu Val Leu Ala Ala Gly Val Pro Asn Lys Pro Gly Ile Pro Lys Leu
145                 150                 155                 160

Leu Glu Gly Ser Lys Asn Ser Ile Gln Trp Glu Lys Ala Glu Asp Asn
                165                 170                 175

Gly Cys Arg Ile Thr Tyr Tyr Ile Leu Glu Ile Arg Lys Ser Thr Ser
            180                 185                 190

Asn Asn Leu Gln Asn Gln Asn Leu Arg Trp Lys Met Thr Phe Asn Gly
```

-continued

```
        195                 200                 205

Ser Cys Ser Ser Val Cys Thr Trp Lys Ser Lys Asn Leu Lys Gly Ile
    210                 215                 220

Phe Gln Phe Arg Val Val Ala Ala Asn Asn Leu Gly Phe Gly Glu Tyr
225                 230                 235                 240

Ser Gly Ile Ser Glu Asn Ile Ile Leu Val Gly Asp Asp Phe Trp Ile
                245                 250                 255

Pro Glu Thr Ser Phe Ile Leu Thr Ile Ile Val Gly Ile Phe Leu Val
            260                 265                 270

Val Thr Ile Pro Leu Thr Phe Val Trp His Arg Arg Leu Lys Asn Gln
        275                 280                 285

Lys Ser Ala Lys Glu Gly Val Thr Val Leu Ile Asn Glu Asp Lys Glu
    290                 295                 300

Leu Ala Glu Leu Arg Gly Leu Ala Ala Gly Val Gly Leu Ala Asn Ala
305                 310                 315                 320

Cys Tyr Ala Ile His Thr Leu Pro Thr Gln Glu Glu Ile Glu Asn Leu
                325                 330                 335

Pro Ala Phe Pro Arg Glu Lys Leu Thr Leu Arg Leu Leu Leu Gly Ser
            340                 345                 350

Gly Ala Phe Gly Glu Val Tyr Glu Gly Thr Ala Val Asp Ile Leu Gly
        355                 360                 365

Val Gly Ser Gly Glu Ile Lys Val Ala Val Lys Thr Leu Lys Lys Gly
    370                 375                 380

Ser Thr Asp Gln Glu Lys Ile Glu Phe Leu Lys Glu Ala His Leu Met
385                 390                 395                 400

Ser Lys Phe Asn His Pro Asn Ile Leu Lys Gln Leu Gly Val Cys Leu
                405                 410                 415

Leu Asn Glu Pro Gln Tyr Ile Ile Leu Glu Leu Met Glu Gly Gly Asp
            420                 425                 430

Leu Leu Thr Tyr Leu Arg Lys Ala Arg Met Ala Thr Phe Tyr Gly Pro
        435                 440                 445

Leu Leu Thr Leu Val Asp Leu Val Asp Leu Cys Val Asp Ile Ser Lys
    450                 455                 460

Gly Cys Val Tyr Leu Glu Arg Met His Phe Ile His Arg Asp Leu Ala
465                 470                 475                 480

Ala Arg Asn Cys Leu Val Ser Val Lys Asp Tyr Thr Ser Pro Arg Ile
                485                 490                 495

Val Lys Ile Gly Asp Phe Gly Leu Ala Arg Asp Ile Tyr Lys Asn Asp
            500                 505                 510

Tyr Tyr Arg Lys Arg Gly Glu Gly Leu Leu Pro Val Arg Trp Met Ala
        515                 520                 525

Pro Glu Ser Leu Met Asp Gly Ile Phe Thr Thr Gln Ser Asp Val Trp
    530                 535                 540

Ser Phe Gly Ile Leu Ile Trp Glu Ile Leu Thr Leu Gly His Gln Pro
545                 550                 555                 560

Tyr Pro Ala His Ser Asn Leu Asp Val Leu Asn Tyr Val Gln Thr Gly
                565                 570                 575

Gly Arg Leu Glu Pro Pro Arg Asn Cys Pro Asp Asp Leu Trp Asn Leu
            580                 585                 590

Met Thr Gln Cys Trp Ala Gln Glu Pro Asp Gln Arg Pro Thr Phe His
        595                 600                 605

Arg Ile Gln Asp Gln Leu Gln Leu Phe Arg Asn Phe Phe Leu Asn Ser
    610                 615                 620
```

-continued

```
Ile Tyr Lys Ser Arg Asp Glu Ala Asn Asn Ser Gly Val Ile Lys Glu
625                 630                 635                 640

Ser Phe Glu Gly Glu Asp Gly Asp Val Ile Cys Leu Asn Ser Asp Asp
                645                 650                 655

Ile Met Pro Val Ala Leu Met Glu Thr Lys Asn Arg Glu Gly Leu Asn
            660                 665                 670

Tyr Met Val Leu Ala Thr Glu Cys Gly Gln Gly Glu Glu Lys Ser Glu
        675                 680                 685

Gly Pro Leu Gly Ser Gln Glu Ser Glu Ser Cys Gly Leu Arg Lys Glu
    690                 695                 700

Glu Lys Glu Pro His Ala Asp Lys Asp Phe Cys Gln Glu Lys Gln Val
705                 710                 715                 720

Ala Tyr Cys Pro Ser Gly Lys Pro Glu Gly Leu Asn Tyr Ala Cys Leu
                725                 730                 735

Thr His Ser Gly Tyr Gly Asp Gly Ser Asp
            740                 745


<210> SEQ ID NO 5
<211> LENGTH: 1932
<212> TYPE: DNA
<213> ORGANISM: Homo sapiens
<220> FEATURE:
<221> NAME/KEY: CDS
<222> LOCATION: (1)..(1932)

<400> SEQUENCE: 5

atg gcc ccc gcc cgt ctg ttc gcg ctg ctg ctg ttc ttc gta ggc gga       48
Met Ala Pro Ala Arg Leu Phe Ala Leu Leu Leu Phe Phe Val Gly Gly
1               5                   10                  15

gtc gcc gag tcg atc cga gag act gag gtc atc gac ccc cag gac ctc       96
Val Ala Glu Ser Ile Arg Glu Thr Glu Val Ile Asp Pro Gln Asp Leu
            20                  25                  30

cta gaa ggc cga tac ttc tcc gga gcc cta cca gac gat gag gat gta      144
Leu Glu Gly Arg Tyr Phe Ser Gly Ala Leu Pro Asp Asp Glu Asp Val
        35                  40                  45

gtg ggg ccc ggg cag gaa tct gat gac ttt gag ctg tct ggc tct gga      192
Val Gly Pro Gly Gln Glu Ser Asp Asp Phe Glu Leu Ser Gly Ser Gly
    50                  55                  60

gat ctg gat gac ttg gaa gac tcc atg atc ggc cct gaa gtt gtc cat      240
Asp Leu Asp Asp Leu Glu Asp Ser Met Ile Gly Pro Glu Val Val His
65                  70                  75                  80

ccc ttg gtg cct cta gat aac cat atc cct gag agg gca ggg tct ggg      288
Pro Leu Val Pro Leu Asp Asn His Ile Pro Glu Arg Ala Gly Ser Gly
                85                  90                  95

agc caa gtc ccc acc gaa ccc aag aaa cta gag gag aat gag gtt atc      336
Ser Gln Val Pro Thr Glu Pro Lys Lys Leu Glu Glu Asn Glu Val Ile
            100                 105                 110

ccc aag aga atc tca ccc gtt gaa gag agt gag gat gtg tcc aac aag      384
Pro Lys Arg Ile Ser Pro Val Glu Glu Ser Glu Asp Val Ser Asn Lys
        115                 120                 125

gtg tca atg tcc agc act gtg cag ggc agc aac atc ttt gag aga acg      432
Val Ser Met Ser Ser Thr Val Gln Gly Ser Asn Ile Phe Glu Arg Thr
    130                 135                 140

gag gtc ctg gca gat gat ttt tgg ata cca gaa aca agt ttc ata ctt      480
Glu Val Leu Ala Asp Asp Phe Trp Ile Pro Glu Thr Ser Phe Ile Leu
145                 150                 155                 160

act att ata gtt gga ata ttt ctg gtt gtt aca atc cca ctg acc ttt      528
Thr Ile Ile Val Gly Ile Phe Leu Val Val Thr Ile Pro Leu Thr Phe
                165                 170                 175
```

-continued

```
gtc tgg cat aga aga tta aag aat caa aaa agt gcc aag gaa ggg gtg      576
Val Trp His Arg Arg Leu Lys Asn Gln Lys Ser Ala Lys Glu Gly Val
            180                 185                 190

aca gtg ctt ata aac gaa gac aaa gag ttg gct gag ctg cga ggt ctg      624
Thr Val Leu Ile Asn Glu Asp Lys Glu Leu Ala Glu Leu Arg Gly Leu
        195                 200                 205

gca gcc gga gta ggc ctg gct aat gcc tgc tat gca ata cat act ctt      672
Ala Ala Gly Val Gly Leu Ala Asn Ala Cys Tyr Ala Ile His Thr Leu
    210                 215                 220

cca acc caa gag gag att gaa aat ctt cct gcc ttc cct cgg gaa aaa      720
Pro Thr Gln Glu Glu Ile Glu Asn Leu Pro Ala Phe Pro Arg Glu Lys
225                 230                 235                 240

ctg act ctg cgt ctc ttg ctg gga agt gga gcc ttt gga gaa gtg tat      768
Leu Thr Leu Arg Leu Leu Leu Gly Ser Gly Ala Phe Gly Glu Val Tyr
                245                 250                 255

gaa gga aca gca gtg gac atc tta gga gtt gga agt gga gaa atc aaa      816
Glu Gly Thr Ala Val Asp Ile Leu Gly Val Gly Ser Gly Glu Ile Lys
            260                 265                 270

gta gca gtg aag act ttg aag aag ggt tcc aca gac cag gag aag att      864
Val Ala Val Lys Thr Leu Lys Lys Gly Ser Thr Asp Gln Glu Lys Ile
        275                 280                 285

gaa ttc ctg aag gag gca cat ctg atg agc aaa ttt aat cat ccc aac      912
Glu Phe Leu Lys Glu Ala His Leu Met Ser Lys Phe Asn His Pro Asn
    290                 295                 300

att ctg aag cag ctt gga gtt tgt ctg ctg aat gaa ccc caa tac att      960
Ile Leu Lys Gln Leu Gly Val Cys Leu Leu Asn Glu Pro Gln Tyr Ile
305                 310                 315                 320

atc ctg gaa ctg atg gag gga gga gac ctt ctt act tat ttg cgt aaa     1008
Ile Leu Glu Leu Met Glu Gly Gly Asp Leu Leu Thr Tyr Leu Arg Lys
                325                 330                 335

gcc cgg atg gca acg ttt tat ggt cct tta ctc acc ttg gtt gac ctt     1056
Ala Arg Met Ala Thr Phe Tyr Gly Pro Leu Leu Thr Leu Val Asp Leu
            340                 345                 350

gta gac ctg tgt gta gat att tca aaa ggc tgt gtc tac ttg gaa cgg     1104
Val Asp Leu Cys Val Asp Ile Ser Lys Gly Cys Val Tyr Leu Glu Arg
        355                 360                 365

atg cat ttc att cac agg gat ctg gca gct aga aat tgc ctt gtt tcc     1152
Met His Phe Ile His Arg Asp Leu Ala Ala Arg Asn Cys Leu Val Ser
    370                 375                 380

gtg aaa gac tat acc agt cca cgg ata gtg aag att gga gac ttt gga     1200
Val Lys Asp Tyr Thr Ser Pro Arg Ile Val Lys Ile Gly Asp Phe Gly
385                 390                 395                 400

ctc gcc aga gac atc tat aaa aat gat tac tat aga aag aga ggg gaa     1248
Leu Ala Arg Asp Ile Tyr Lys Asn Asp Tyr Tyr Arg Lys Arg Gly Glu
                405                 410                 415

ggc ctg ctc cca gtt cgg tgg atg gct cca gaa agt ttg atg gat gga     1296
Gly Leu Leu Pro Val Arg Trp Met Ala Pro Glu Ser Leu Met Asp Gly
            420                 425                 430

atc ttc act act caa tct gat gta tgg tct ttt gga att ctg att tgg     1344
Ile Phe Thr Thr Gln Ser Asp Val Trp Ser Phe Gly Ile Leu Ile Trp
        435                 440                 445

gag att tta act ctt ggt cat cag cct tat cca gct cat tcc aac ctt     1392
Glu Ile Leu Thr Leu Gly His Gln Pro Tyr Pro Ala His Ser Asn Leu
    450                 455                 460

gat gtg tta aac tat gtg caa aca gga ggg aga ctg gag cca cca aga     1440
Asp Val Leu Asn Tyr Val Gln Thr Gly Gly Arg Leu Glu Pro Pro Arg
465                 470                 475                 480

aat tgt cct gat gat ctg tgg aat tta atg acc cag tgc tgg gct caa     1488
Asn Cys Pro Asp Asp Leu Trp Asn Leu Met Thr Gln Cys Trp Ala Gln
```

```
                485                 490                 495

gaa ccc gac caa aga cct act ttt cat aga att cag gac caa ctt cag      1536
Glu Pro Asp Gln Arg Pro Thr Phe His Arg Ile Gln Asp Gln Leu Gln
            500                 505                 510

tta ttc aga aat ttt ttc tta aat agc att tat aag tcc aga gat gaa      1584
Leu Phe Arg Asn Phe Phe Leu Asn Ser Ile Tyr Lys Ser Arg Asp Glu
        515                 520                 525

gca aac aac agt gga gtc ata aag gaa agc ttt gaa ggt gaa gat ggc      1632
Ala Asn Asn Ser Gly Val Ile Lys Glu Ser Phe Glu Gly Glu Asp Gly
    530                 535                 540

gat gtg att tgt ttg aat tca gat gac att atg cca gtt gct tta atg      1680
Asp Val Ile Cys Leu Asn Ser Asp Asp Ile Met Pro Val Ala Leu Met
545                 550                 555                 560

gaa acg aag aac cga gaa ggg tta aac tat atg gta ctt gct aca gaa      1728
Glu Thr Lys Asn Arg Glu Gly Leu Asn Tyr Met Val Leu Ala Thr Glu
                565                 570                 575

tgt ggc caa ggt gaa gaa aag tct gag ggt cct cta ggc tcc cag gaa      1776
Cys Gly Gln Gly Glu Glu Lys Ser Glu Gly Pro Leu Gly Ser Gln Glu
            580                 585                 590

tct gaa tct tgt ggt ctg agg aaa gaa gag aag gaa cca cat gca gac      1824
Ser Glu Ser Cys Gly Leu Arg Lys Glu Glu Lys Glu Pro His Ala Asp
        595                 600                 605

aaa gat ttc tgc caa gaa aaa caa gtg gct tac tgc cct tct ggc aag      1872
Lys Asp Phe Cys Gln Glu Lys Gln Val Ala Tyr Cys Pro Ser Gly Lys
    610                 615                 620

cct gaa ggc ctg aac tat gcc tgt ctc act cac agt gga tat gga gat      1920
Pro Glu Gly Leu Asn Tyr Ala Cys Leu Thr His Ser Gly Tyr Gly Asp
625                 630                 635                 640

ggg tct gat taa                                                      1932
Gly Ser Asp


<210> SEQ ID NO 6
<211> LENGTH: 643
<212> TYPE: PRT
<213> ORGANISM: Homo sapiens

<400> SEQUENCE: 6

Met Ala Pro Ala Arg Leu Phe Ala Leu Leu Leu Phe Phe Val Gly Gly
1               5                   10                  15

Val Ala Glu Ser Ile Arg Glu Thr Glu Val Ile Asp Pro Gln Asp Leu
            20                  25                  30

Leu Glu Gly Arg Tyr Phe Ser Gly Ala Leu Pro Asp Asp Glu Asp Val
        35                  40                  45

Val Gly Pro Gly Gln Glu Ser Asp Asp Phe Glu Leu Ser Gly Ser Gly
    50                  55                  60

Asp Leu Asp Asp Leu Glu Asp Ser Met Ile Gly Pro Glu Val Val His
65                  70                  75                  80

Pro Leu Val Pro Leu Asp Asn His Ile Pro Glu Arg Ala Gly Ser Gly
                85                  90                  95

Ser Gln Val Pro Thr Glu Pro Lys Lys Leu Glu Glu Asn Glu Val Ile
            100                 105                 110

Pro Lys Arg Ile Ser Pro Val Glu Glu Ser Glu Asp Val Ser Asn Lys
        115                 120                 125

Val Ser Met Ser Ser Thr Val Gln Gly Ser Asn Ile Phe Glu Arg Thr
    130                 135                 140

Glu Val Leu Ala Asp Asp Phe Trp Ile Pro Glu Thr Ser Phe Ile Leu
145                 150                 155                 160
```

```
Thr Ile Ile Val Gly Ile Phe Leu Val Val Thr Ile Pro Leu Thr Phe
                165                 170                 175

Val Trp His Arg Arg Leu Lys Asn Gln Lys Ser Ala Lys Glu Gly Val
            180                 185                 190

Thr Val Leu Ile Asn Glu Asp Lys Glu Leu Ala Glu Leu Arg Gly Leu
        195                 200                 205

Ala Ala Gly Val Gly Leu Ala Asn Ala Cys Tyr Ala Ile His Thr Leu
    210                 215                 220

Pro Thr Gln Glu Glu Ile Glu Asn Leu Pro Ala Phe Pro Arg Glu Lys
225                 230                 235                 240

Leu Thr Leu Arg Leu Leu Leu Gly Ser Gly Ala Phe Gly Glu Val Tyr
                245                 250                 255

Glu Gly Thr Ala Val Asp Ile Leu Gly Val Gly Ser Gly Glu Ile Lys
            260                 265                 270

Val Ala Val Lys Thr Leu Lys Lys Gly Ser Thr Asp Gln Glu Lys Ile
        275                 280                 285

Glu Phe Leu Lys Glu Ala His Leu Met Ser Lys Phe Asn His Pro Asn
    290                 295                 300

Ile Leu Lys Gln Leu Gly Val Cys Leu Leu Asn Glu Pro Gln Tyr Ile
305                 310                 315                 320

Ile Leu Glu Leu Met Glu Gly Gly Asp Leu Leu Thr Tyr Leu Arg Lys
                325                 330                 335

Ala Arg Met Ala Thr Phe Tyr Gly Pro Leu Leu Thr Leu Val Asp Leu
            340                 345                 350

Val Asp Leu Cys Val Asp Ile Ser Lys Gly Cys Val Tyr Leu Glu Arg
        355                 360                 365

Met His Phe Ile His Arg Asp Leu Ala Ala Arg Asn Cys Leu Val Ser
    370                 375                 380

Val Lys Asp Tyr Thr Ser Pro Arg Ile Val Lys Ile Gly Asp Phe Gly
385                 390                 395                 400

Leu Ala Arg Asp Ile Tyr Lys Asn Asp Tyr Tyr Arg Lys Arg Gly Glu
                405                 410                 415

Gly Leu Leu Pro Val Arg Trp Met Ala Pro Glu Ser Leu Met Asp Gly
            420                 425                 430

Ile Phe Thr Thr Gln Ser Asp Val Trp Ser Phe Gly Ile Leu Ile Trp
        435                 440                 445

Glu Ile Leu Thr Leu Gly His Gln Pro Tyr Pro Ala His Ser Asn Leu
    450                 455                 460

Asp Val Leu Asn Tyr Val Gln Thr Gly Gly Arg Leu Glu Pro Pro Arg
465                 470                 475                 480

Asn Cys Pro Asp Asp Leu Trp Asn Leu Met Thr Gln Cys Trp Ala Gln
                485                 490                 495

Glu Pro Asp Gln Arg Pro Thr Phe His Arg Ile Gln Asp Gln Leu Gln
            500                 505                 510

Leu Phe Arg Asn Phe Phe Leu Asn Ser Ile Tyr Lys Ser Arg Asp Glu
        515                 520                 525

Ala Asn Asn Ser Gly Val Ile Lys Glu Ser Phe Glu Gly Glu Asp Gly
    530                 535                 540

Asp Val Ile Cys Leu Asn Ser Asp Asp Ile Met Pro Val Ala Leu Met
545                 550                 555                 560

Glu Thr Lys Asn Arg Glu Gly Leu Asn Tyr Met Val Leu Ala Thr Glu
                565                 570                 575

Cys Gly Gln Gly Glu Glu Lys Ser Glu Gly Pro Leu Gly Ser Gln Glu
```

-continued

```
            580                 585                 590

Ser Glu Ser Cys Gly Leu Arg Lys Glu Glu Lys Glu Pro His Ala Asp
        595                 600                 605

Lys Asp Phe Cys Gln Glu Lys Gln Val Ala Tyr Cys Pro Ser Gly Lys
    610                 615                 620

Pro Glu Gly Leu Asn Tyr Ala Cys Leu Thr His Ser Gly Tyr Gly Asp
625                 630                 635                 640

Gly Ser Asp


<210> SEQ ID NO 7
<211> LENGTH: 2421
<212> TYPE: DNA
<213> ORGANISM: Homo sapiens
<220> FEATURE:
<221> NAME/KEY: CDS
<222> LOCATION: (1)..(2421)

<400> SEQUENCE: 7

atg cac agg agg aga agc agg agc tgt cgg gaa gat cag aag cca gtc       48
Met His Arg Arg Arg Ser Arg Ser Cys Arg Glu Asp Gln Lys Pro Val
1               5                   10                  15

atg gat gac cag cgc gac ctt atc tcc aac aat gag caa ctg ccc atg       96
Met Asp Asp Gln Arg Asp Leu Ile Ser Asn Asn Glu Gln Leu Pro Met
            20                  25                  30

ctg ggc cgg cgc cct ggg gcc ccg gag agc aag tgc agc cgc gga gcc      144
Leu Gly Arg Arg Pro Gly Ala Pro Glu Ser Lys Cys Ser Arg Gly Ala
        35                  40                  45

ctg tac aca ggc ttt tcc atc ctg gtg act ctg ctc ctc gct ggc cag      192
Leu Tyr Thr Gly Phe Ser Ile Leu Val Thr Leu Leu Leu Ala Gly Gln
    50                  55                  60

gcc acc acc gcc tac ttc ctg tac cag cag cag ggc cgg ctg gac aaa      240
Ala Thr Thr Ala Tyr Phe Leu Tyr Gln Gln Gln Gly Arg Leu Asp Lys
65                  70                  75                  80

ctg aca gtc acc tcc cag aac ctg cag ctg gag aac ctg cgc atg aag      288
Leu Thr Val Thr Ser Gln Asn Leu Gln Leu Glu Asn Leu Arg Met Lys
                85                  90                  95

ctt ccc aag cct ccc aag cct gtg agc aag atg cgc atg gcc acc ccg      336
Leu Pro Lys Pro Pro Lys Pro Val Ser Lys Met Arg Met Ala Thr Pro
            100                 105                 110

ctg ctg atg cag gcg ctg ccc atg gga gcc ctg ccc cag ggg ccc atg      384
Leu Leu Met Gln Ala Leu Pro Met Gly Ala Leu Pro Gln Gly Pro Met
        115                 120                 125

cag aat gcc acc aag tat ggc aac atg aca gag gac cat gtg atg cac      432
Gln Asn Ala Thr Lys Tyr Gly Asn Met Thr Glu Asp His Val Met His
    130                 135                 140

ctg ctc cag aat gct gac ccc ctg aag gtg tac ccg cca ctg aag ggg      480
Leu Leu Gln Asn Ala Asp Pro Leu Lys Val Tyr Pro Pro Leu Lys Gly
145                 150                 155                 160

agc ttc ccg gag aac ctg aga cac ctt aag aac acc atg gag acc ata      528
Ser Phe Pro Glu Asn Leu Arg His Leu Lys Asn Thr Met Glu Thr Ile
                165                 170                 175

gac tgg aag gtc ttt gag agc tgg atg cac cat tgg ctc ctg ttt gaa      576
Asp Trp Lys Val Phe Glu Ser Trp Met His His Trp Leu Leu Phe Glu
            180                 185                 190

atg agc agg cac tcc ttg gag caa aag ccc act gac gct cca ccg aaa      624
Met Ser Arg His Ser Leu Glu Gln Lys Pro Thr Asp Ala Pro Pro Lys
        195                 200                 205

gct gga gtc cca aat aaa cca ggc att ccc aaa tta cta gaa ggg agt      672
Ala Gly Val Pro Asn Lys Pro Gly Ile Pro Lys Leu Leu Glu Gly Ser
    210                 215                 220
```

-continued

```
aaa aat tca ata cag tgg gag aaa gct gaa gat aat gga tgt aga att      720
Lys Asn Ser Ile Gln Trp Glu Lys Ala Glu Asp Asn Gly Cys Arg Ile
225                 230                 235                 240

aca tac tat atc ctt gag ata aga aag agc act tca aat aat tta cag      768
Thr Tyr Tyr Ile Leu Glu Ile Arg Lys Ser Thr Ser Asn Asn Leu Gln
                245                 250                 255

aac cag aat tta agg tgg aag atg aca ttt aat gga tcc tgc agt agt      816
Asn Gln Asn Leu Arg Trp Lys Met Thr Phe Asn Gly Ser Cys Ser Ser
            260                 265                 270

gtt tgc aca tgg aag tcc aaa aac ctg aaa gga ata ttt cag ttc aga      864
Val Cys Thr Trp Lys Ser Lys Asn Leu Lys Gly Ile Phe Gln Phe Arg
        275                 280                 285

gta gta gct gca aat aat cta ggg ttt ggt gaa tat agt gga atc agt      912
Val Val Ala Ala Asn Asn Leu Gly Phe Gly Glu Tyr Ser Gly Ile Ser
    290                 295                 300

gag aat att ata tta gtt gga gat gat ttt tgg ata cca gaa aca agt      960
Glu Asn Ile Ile Leu Val Gly Asp Asp Phe Trp Ile Pro Glu Thr Ser
305                 310                 315                 320

ttc ata ctt act att ata gtt gga ata ttt ctg gtt gtt aca atc cca     1008
Phe Ile Leu Thr Ile Ile Val Gly Ile Phe Leu Val Val Thr Ile Pro
                325                 330                 335

ctg acc ttt gtc tgg cat aga aga tta aag aat caa aaa agt gcc aag     1056
Leu Thr Phe Val Trp His Arg Arg Leu Lys Asn Gln Lys Ser Ala Lys
            340                 345                 350

gaa ggg gtg aca gtg ctt ata aac gaa gac aaa gag ttg gct gag ctg     1104
Glu Gly Val Thr Val Leu Ile Asn Glu Asp Lys Glu Leu Ala Glu Leu
        355                 360                 365

cga ggt ctg gca gct gga gta ggc ctg gct aat gcc tgc tat gca ata     1152
Arg Gly Leu Ala Ala Gly Val Gly Leu Ala Asn Ala Cys Tyr Ala Ile
    370                 375                 380

cat act ctt cca acc caa gag gag att gaa aat ctt cct gcc ttc cct     1200
His Thr Leu Pro Thr Gln Glu Glu Ile Glu Asn Leu Pro Ala Phe Pro
385                 390                 395                 400

cgg gaa aaa ctg act ctg cgt ctc ttg ctg gga agt gga gcc ttt gga     1248
Arg Glu Lys Leu Thr Leu Arg Leu Leu Leu Gly Ser Gly Ala Phe Gly
                405                 410                 415

gaa gtg tat gaa gga aca gca gtg gac atc tta gga gtt gga agt gga     1296
Glu Val Tyr Glu Gly Thr Ala Val Asp Ile Leu Gly Val Gly Ser Gly
            420                 425                 430

gaa atc aaa gta gca gtg aag act ttg aag aag ggt tcc aca gac cag     1344
Glu Ile Lys Val Ala Val Lys Thr Leu Lys Lys Gly Ser Thr Asp Gln
        435                 440                 445

gag aag att gaa ttc ctg aag gag gca cat ctg atg agc aaa ttt aat     1392
Glu Lys Ile Glu Phe Leu Lys Glu Ala His Leu Met Ser Lys Phe Asn
    450                 455                 460

cat ccc aac att ctg aag cag ctt gga gtt tgt ctg ctg aat gaa ccc     1440
His Pro Asn Ile Leu Lys Gln Leu Gly Val Cys Leu Leu Asn Glu Pro
465                 470                 475                 480

caa tac att atc ctg gaa ctg atg gag gga gga gac ctt ctt act tat     1488
Gln Tyr Ile Ile Leu Glu Leu Met Glu Gly Gly Asp Leu Leu Thr Tyr
                485                 490                 495

ttg cgt aaa gcc cgg atg gca acg ttt tat ggt cct tta ctc acc ttg     1536
Leu Arg Lys Ala Arg Met Ala Thr Phe Tyr Gly Pro Leu Leu Thr Leu
            500                 505                 510

gtt gac ctt gta gac ctg tgt gta gat att tca aaa ggc tgt gtc tac     1584
Val Asp Leu Val Asp Leu Cys Val Asp Ile Ser Lys Gly Cys Val Tyr
        515                 520                 525

ttg gaa cgg atg cat ttc att cac agg gat ctg gca gct aga aat tgc     1632
Leu Glu Arg Met His Phe Ile His Arg Asp Leu Ala Ala Arg Asn Cys
```

-continued

```
    530                 535                 540

ctt gtt tcc gtg aaa gac tat acc agt cca cgg ata gtg aag att gga      1680
Leu Val Ser Val Lys Asp Tyr Thr Ser Pro Arg Ile Val Lys Ile Gly
545                 550                 555                 560

gac ttt gga ctc gcc aga gac atc tat aaa aat gat tac tat aga aag      1728
Asp Phe Gly Leu Ala Arg Asp Ile Tyr Lys Asn Asp Tyr Tyr Arg Lys
                565                 570                 575

aga ggg gaa ggc ctg ctc cca gtt cgg tgg atg gct cca gaa agt ttg      1776
Arg Gly Glu Gly Leu Leu Pro Val Arg Trp Met Ala Pro Glu Ser Leu
            580                 585                 590

atg gat gga atc ttc act act caa tct gat gta tgg tct ttt gga att      1824
Met Asp Gly Ile Phe Thr Thr Gln Ser Asp Val Trp Ser Phe Gly Ile
        595                 600                 605

ctg att tgg gag att tta act ctt ggt cat cag cct tat cca gct cat      1872
Leu Ile Trp Glu Ile Leu Thr Leu Gly His Gln Pro Tyr Pro Ala His
    610                 615                 620

tcc aac ctt gat gtg tta aac tat gtg caa aca gga ggg aga ctg gag      1920
Ser Asn Leu Asp Val Leu Asn Tyr Val Gln Thr Gly Gly Arg Leu Glu
625                 630                 635                 640

cca cca aga aat tgt cct gat gat ctg tgg aat tta atg acc cag tgc      1968
Pro Pro Arg Asn Cys Pro Asp Asp Leu Trp Asn Leu Met Thr Gln Cys
                645                 650                 655

tgg gct caa gaa ccc gac caa aga cct act ttt cat aga att cag gac      2016
Trp Ala Gln Glu Pro Asp Gln Arg Pro Thr Phe His Arg Ile Gln Asp
            660                 665                 670

caa ctt cag tta ttc aga aat ttt ttc tta aat agc att tat aag tcc      2064
Gln Leu Gln Leu Phe Arg Asn Phe Phe Leu Asn Ser Ile Tyr Lys Ser
        675                 680                 685

aga gat gaa gca aac aac agt gga gtc ata aat gaa agc ttt gaa ggt      2112
Arg Asp Glu Ala Asn Asn Ser Gly Val Ile Asn Glu Ser Phe Glu Gly
    690                 695                 700

gaa gat ggc gat gtg att tgt ttg aat tca gat gac att atg cca gtt      2160
Glu Asp Gly Asp Val Ile Cys Leu Asn Ser Asp Asp Ile Met Pro Val
705                 710                 715                 720

gct tta atg gaa acg aag aac cga gaa ggg tta aac tat atg gta ctt      2208
Ala Leu Met Glu Thr Lys Asn Arg Glu Gly Leu Asn Tyr Met Val Leu
                725                 730                 735

gct aca gaa tgt ggc caa ggt gaa gaa aag tct gag ggt cct cta ggc      2256
Ala Thr Glu Cys Gly Gln Gly Glu Glu Lys Ser Glu Gly Pro Leu Gly
            740                 745                 750

tcc cag gaa tct gaa tct tgt ggt ctg agg aaa gaa gag aag gaa cca      2304
Ser Gln Glu Ser Glu Ser Cys Gly Leu Arg Lys Glu Glu Lys Glu Pro
        755                 760                 765

cat gca gac aaa gat ttc tgc caa gaa aaa caa gtg gct tac tgc cct      2352
His Ala Asp Lys Asp Phe Cys Gln Glu Lys Gln Val Ala Tyr Cys Pro
    770                 775                 780

tct ggc aag cct gaa ggc ctg aac tat gcc tgt ctc act cac agt gga      2400
Ser Gly Lys Pro Glu Gly Leu Asn Tyr Ala Cys Leu Thr His Ser Gly
785                 790                 795                 800

tat gga gat ggg tct gat taa                                          2421
Tyr Gly Asp Gly Ser Asp
                805
```

<210> SEQ ID NO 8
<211> LENGTH: 806
<212> TYPE: PRT
<213> ORGANISM: Homo sapiens

<400> SEQUENCE: 8

```
Met His Arg Arg Arg Ser Arg Ser Cys Arg Glu Asp Gln Lys Pro Val
```

-continued

```
1               5                   10                  15

Met Asp Asp Gln Arg Asp Leu Ile Ser Asn Asn Glu Gln Leu Pro Met
            20                  25                  30

Leu Gly Arg Arg Pro Gly Ala Pro Glu Ser Lys Cys Ser Arg Gly Ala
        35                  40                  45

Leu Tyr Thr Gly Phe Ser Ile Leu Val Thr Leu Leu Leu Ala Gly Gln
    50                  55                  60

Ala Thr Thr Ala Tyr Phe Leu Tyr Gln Gln Gln Gly Arg Leu Asp Lys
65                  70                  75                  80

Leu Thr Val Thr Ser Gln Asn Leu Gln Leu Glu Asn Leu Arg Met Lys
                85                  90                  95

Leu Pro Lys Pro Pro Lys Pro Val Ser Lys Met Arg Met Ala Thr Pro
            100                 105                 110

Leu Leu Met Gln Ala Leu Pro Met Gly Ala Leu Pro Gln Gly Pro Met
        115                 120                 125

Gln Asn Ala Thr Lys Tyr Gly Asn Met Thr Glu Asp His Val Met His
    130                 135                 140

Leu Leu Gln Asn Ala Asp Pro Leu Lys Val Tyr Pro Pro Leu Lys Gly
145                 150                 155                 160

Ser Phe Pro Glu Asn Leu Arg His Leu Lys Asn Thr Met Glu Thr Ile
                165                 170                 175

Asp Trp Lys Val Phe Glu Ser Trp Met His His Trp Leu Leu Phe Glu
            180                 185                 190

Met Ser Arg His Ser Leu Glu Gln Lys Pro Thr Asp Ala Pro Pro Lys
        195                 200                 205

Ala Gly Val Pro Asn Lys Pro Gly Ile Pro Lys Leu Leu Glu Gly Ser
    210                 215                 220

Lys Asn Ser Ile Gln Trp Glu Lys Ala Glu Asp Asn Gly Cys Arg Ile
225                 230                 235                 240

Thr Tyr Tyr Ile Leu Glu Ile Arg Lys Ser Thr Ser Asn Asn Leu Gln
                245                 250                 255

Asn Gln Asn Leu Arg Trp Lys Met Thr Phe Asn Gly Ser Cys Ser Ser
            260                 265                 270

Val Cys Thr Trp Lys Ser Lys Asn Leu Lys Gly Ile Phe Gln Phe Arg
        275                 280                 285

Val Val Ala Ala Asn Asn Leu Gly Phe Gly Glu Tyr Ser Gly Ile Ser
    290                 295                 300

Glu Asn Ile Ile Leu Val Gly Asp Asp Phe Trp Ile Pro Glu Thr Ser
305                 310                 315                 320

Phe Ile Leu Thr Ile Ile Val Gly Ile Phe Leu Val Val Thr Ile Pro
                325                 330                 335

Leu Thr Phe Val Trp His Arg Arg Leu Lys Asn Gln Lys Ser Ala Lys
            340                 345                 350

Glu Gly Val Thr Val Leu Ile Asn Glu Asp Lys Glu Leu Ala Glu Leu
        355                 360                 365

Arg Gly Leu Ala Ala Gly Val Gly Leu Ala Asn Ala Cys Tyr Ala Ile
    370                 375                 380

His Thr Leu Pro Thr Gln Glu Glu Ile Glu Asn Leu Pro Ala Phe Pro
385                 390                 395                 400

Arg Glu Lys Leu Thr Leu Arg Leu Leu Leu Gly Ser Gly Ala Phe Gly
                405                 410                 415

Glu Val Tyr Glu Gly Thr Ala Val Asp Ile Leu Gly Val Gly Ser Gly
            420                 425                 430
```

```
Glu Ile Lys Val Ala Val Lys Thr Leu Lys Lys Gly Ser Thr Asp Gln
        435                 440                 445

Glu Lys Ile Glu Phe Leu Lys Glu Ala His Leu Met Ser Lys Phe Asn
    450                 455                 460

His Pro Asn Ile Leu Lys Gln Leu Gly Val Cys Leu Leu Asn Glu Pro
465                 470                 475                 480

Gln Tyr Ile Ile Leu Glu Leu Met Glu Gly Gly Asp Leu Leu Thr Tyr
                485                 490                 495

Leu Arg Lys Ala Arg Met Ala Thr Phe Tyr Gly Pro Leu Leu Thr Leu
            500                 505                 510

Val Asp Leu Val Asp Leu Cys Val Asp Ile Ser Lys Gly Cys Val Tyr
        515                 520                 525

Leu Glu Arg Met His Phe Ile His Arg Asp Leu Ala Ala Arg Asn Cys
    530                 535                 540

Leu Val Ser Val Lys Asp Tyr Thr Ser Pro Arg Ile Val Lys Ile Gly
545                 550                 555                 560

Asp Phe Gly Leu Ala Arg Asp Ile Tyr Lys Asn Asp Tyr Tyr Arg Lys
                565                 570                 575

Arg Gly Glu Gly Leu Leu Pro Val Arg Trp Met Ala Pro Glu Ser Leu
            580                 585                 590

Met Asp Gly Ile Phe Thr Thr Gln Ser Asp Val Trp Ser Phe Gly Ile
        595                 600                 605

Leu Ile Trp Glu Ile Leu Thr Leu Gly His Gln Pro Tyr Pro Ala His
    610                 615                 620

Ser Asn Leu Asp Val Leu Asn Tyr Val Gln Thr Gly Gly Arg Leu Glu
625                 630                 635                 640

Pro Pro Arg Asn Cys Pro Asp Asp Leu Trp Asn Leu Met Thr Gln Cys
                645                 650                 655

Trp Ala Gln Glu Pro Asp Gln Arg Pro Thr Phe His Arg Ile Gln Asp
            660                 665                 670

Gln Leu Gln Leu Phe Arg Asn Phe Phe Leu Asn Ser Ile Tyr Lys Ser
        675                 680                 685

Arg Asp Glu Ala Asn Asn Ser Gly Val Ile Asn Glu Ser Phe Glu Gly
    690                 695                 700

Glu Asp Gly Asp Val Ile Cys Leu Asn Ser Asp Asp Ile Met Pro Val
705                 710                 715                 720

Ala Leu Met Glu Thr Lys Asn Arg Glu Gly Leu Asn Tyr Met Val Leu
                725                 730                 735

Ala Thr Glu Cys Gly Gln Gly Glu Glu Lys Ser Glu Gly Pro Leu Gly
            740                 745                 750

Ser Gln Glu Ser Glu Ser Cys Gly Leu Arg Lys Glu Glu Lys Glu Pro
        755                 760                 765

His Ala Asp Lys Asp Phe Cys Gln Glu Lys Gln Val Ala Tyr Cys Pro
    770                 775                 780

Ser Gly Lys Pro Glu Gly Leu Asn Tyr Ala Cys Leu Thr His Ser Gly
785                 790                 795                 800

Tyr Gly Asp Gly Ser Asp
                805
```

<210> SEQ ID NO 9
<211> LENGTH: 2577
<212> TYPE: DNA
<213> ORGANISM: Homo sapiens
<220> FEATURE:

```
<221> NAME/KEY: CDS
<222> LOCATION: (1)..(2577)

<400> SEQUENCE: 9

atg ccg aaa cca atc aat gtc cga gtt acc acc atg gat gca gag ctg       48
Met Pro Lys Pro Ile Asn Val Arg Val Thr Thr Met Asp Ala Glu Leu
1               5                   10                  15

gag ttt gca atc cag cca aat aca act gga aaa cag ctt ttt gat cag       96
Glu Phe Ala Ile Gln Pro Asn Thr Thr Gly Lys Gln Leu Phe Asp Gln
            20                  25                  30

gtg gta aag act atc ggc ctc cgg gaa gtg tgg tac ttt ggc ctc cac      144
Val Val Lys Thr Ile Gly Leu Arg Glu Val Trp Tyr Phe Gly Leu His
        35                  40                  45

tat gtg gat aat aaa gga ttt cct acc tgg ctg aag ctg gat aag aag      192
Tyr Val Asp Asn Lys Gly Phe Pro Thr Trp Leu Lys Leu Asp Lys Lys
    50                  55                  60

gtg tct gcc cag gag gtc agg aag gag aat ccc ctc cag ttc aag ttc      240
Val Ser Ala Gln Glu Val Arg Lys Glu Asn Pro Leu Gln Phe Lys Phe
65                  70                  75                  80

cgg gcc aag ttc tac cct gaa gat gtg gct gag gag ctc atc cag gac      288
Arg Ala Lys Phe Tyr Pro Glu Asp Val Ala Glu Glu Leu Ile Gln Asp
                85                  90                  95

atc acc cag aaa cat ttc ttc ctc caa gtg aag gaa gga atc ctt agc      336
Ile Thr Gln Lys His Phe Phe Leu Gln Val Lys Glu Gly Ile Leu Ser
            100                 105                 110

gat gag atc tac tgc ccc cct gag act gcc gtg ctc ttg ggg tcc tac      384
Asp Glu Ile Tyr Cys Pro Pro Glu Thr Ala Val Leu Leu Gly Ser Tyr
        115                 120                 125

gct gtg cag gcc aag ttt ggg gac tac aac aaa gaa gtg cac aag tct      432
Ala Val Gln Ala Lys Phe Gly Asp Tyr Asn Lys Glu Val His Lys Ser
    130                 135                 140

ggg tac ctc agc tct gag cgg ctg atc cct caa aga gtg atg gac cag      480
Gly Tyr Leu Ser Ser Glu Arg Leu Ile Pro Gln Arg Val Met Asp Gln
145                 150                 155                 160

cac aaa ctt acc agg gac cag tgg gag gac cgg atc cag gtg tgg cat      528
His Lys Leu Thr Arg Asp Gln Trp Glu Asp Arg Ile Gln Val Trp His
                165                 170                 175

gcg gaa cac cgt ggg atg ctc aaa gat aat gct atg ttg gaa tac ctg      576
Ala Glu His Arg Gly Met Leu Lys Asp Asn Ala Met Leu Glu Tyr Leu
            180                 185                 190

aag att gct cag gac ctg gaa atg tat gga atc aac tat ttc gag ata      624
Lys Ile Ala Gln Asp Leu Glu Met Tyr Gly Ile Asn Tyr Phe Glu Ile
        195                 200                 205

aaa aac aag aaa gga aca gac ctt tgg ctt gga gtt gat gcc ctt gga      672
Lys Asn Lys Lys Gly Thr Asp Leu Trp Leu Gly Val Asp Ala Leu Gly
    210                 215                 220

ctg aat att tat gag aaa gat gat aag tta acc cca aag att ggc ttt      720
Leu Asn Ile Tyr Glu Lys Asp Asp Lys Leu Thr Pro Lys Ile Gly Phe
225                 230                 235                 240

cct tgg agt gaa atc agg aac atc tct ttc aat gac aaa aag ttt gtc      768
Pro Trp Ser Glu Ile Arg Asn Ile Ser Phe Asn Asp Lys Lys Phe Val
                245                 250                 255

att aaa ccc atc gac aag aag gca cct gac ttt gtg ttt tat gcc cca      816
Ile Lys Pro Ile Asp Lys Lys Ala Pro Asp Phe Val Phe Tyr Ala Pro
            260                 265                 270

cgt ctg aga atc aac aag cgg atc ctg cag ctc tgc atg ggc aac cat      864
Arg Leu Arg Ile Asn Lys Arg Ile Leu Gln Leu Cys Met Gly Asn His
        275                 280                 285

gag ttg tat atg cgc cgc agg aag cct gac acc atc gag gtg cag cag      912
Glu Leu Tyr Met Arg Arg Arg Lys Pro Asp Thr Ile Glu Val Gln Gln
```

-continued

```
    290                 295                 300

atg aag gcc cag gcc cgg gag gag aag cat cag aag cag ctg gag cgg      960
Met Lys Ala Gln Ala Arg Glu Glu Lys His Gln Lys Gln Leu Glu Arg
305                 310                 315                 320

caa cag ctg gaa aca gag aag aaa agg aga gaa acc gtg gag aga gag     1008
Gln Gln Leu Glu Thr Glu Lys Lys Arg Arg Glu Thr Val Glu Arg Glu
                325                 330                 335

aaa gag cag atg atg cgc gag aag gag gag ttg atg ctg cgg ctg cag     1056
Lys Glu Gln Met Met Arg Glu Lys Glu Glu Leu Met Leu Arg Leu Gln
            340                 345                 350

gac tat gag gag aag aca aag aag gca gag aga gat gat ttt tgg ata     1104
Asp Tyr Glu Glu Lys Thr Lys Lys Ala Glu Arg Asp Asp Phe Trp Ile
        355                 360                 365

cca gaa aca agt ttc ata ctt act att ata gtt gga ata ttt ctg gtt     1152
Pro Glu Thr Ser Phe Ile Leu Thr Ile Ile Val Gly Ile Phe Leu Val
    370                 375                 380

gtt aca atc cca ctg acc ttt gtc tgg cat aga aga tta aag aat caa     1200
Val Thr Ile Pro Leu Thr Phe Val Trp His Arg Arg Leu Lys Asn Gln
385                 390                 395                 400

aaa agt gcc aag gaa ggg gtg aca gtg ctt ata aac gaa gac aaa gag     1248
Lys Ser Ala Lys Glu Gly Val Thr Val Leu Ile Asn Glu Asp Lys Glu
                405                 410                 415

ttg gct gag ctg cga ggt ctg gca gct gga gta ggc ctg gct aat gcc     1296
Leu Ala Glu Leu Arg Gly Leu Ala Ala Gly Val Gly Leu Ala Asn Ala
            420                 425                 430

tgc tat gca ata cat act ctt cca acc caa gag gag att gaa aat ctt     1344
Cys Tyr Ala Ile His Thr Leu Pro Thr Gln Glu Glu Ile Glu Asn Leu
        435                 440                 445

cct gcc ttc cct cgg gaa aaa ctg act ctg cgt ctc ttg ctg gga agt     1392
Pro Ala Phe Pro Arg Glu Lys Leu Thr Leu Arg Leu Leu Leu Gly Ser
    450                 455                 460

gga gcc ttt gga gaa gtg tat gaa gga aca gca gtg gac atc tta gga     1440
Gly Ala Phe Gly Glu Val Tyr Glu Gly Thr Ala Val Asp Ile Leu Gly
465                 470                 475                 480

gtt gga agt gga gaa atc aaa gta gca gtg aag act ttg aag aag ggt     1488
Val Gly Ser Gly Glu Ile Lys Val Ala Val Lys Thr Leu Lys Lys Gly
                485                 490                 495

tcc aca gac cag gag aag att gaa ttc ctg aag gag gca cat ctg atg     1536
Ser Thr Asp Gln Glu Lys Ile Glu Phe Leu Lys Glu Ala His Leu Met
            500                 505                 510

agc aaa ttt aat cat ccc aac att ctg aag cag ctt gga gtt tgt ctg     1584
Ser Lys Phe Asn His Pro Asn Ile Leu Lys Gln Leu Gly Val Cys Leu
        515                 520                 525

ctg aat gaa ccc caa tac att atc ctg gaa ctg atg gag gga gga gac     1632
Leu Asn Glu Pro Gln Tyr Ile Ile Leu Glu Leu Met Glu Gly Gly Asp
    530                 535                 540

ctt ctt act tat ttg cgt aaa gcc cgg atg gca acg ttt tat ggt cct     1680
Leu Leu Thr Tyr Leu Arg Lys Ala Arg Met Ala Thr Phe Tyr Gly Pro
545                 550                 555                 560

tta ctc acc ttg gtt gac ctt gta gac ctg tgt gta gat att tca aaa     1728
Leu Leu Thr Leu Val Asp Leu Val Asp Leu Cys Val Asp Ile Ser Lys
                565                 570                 575

ggc tgt gtc tac ttg gaa cgg atg cat ttc att cac agg gat ctg gca     1776
Gly Cys Val Tyr Leu Glu Arg Met His Phe Ile His Arg Asp Leu Ala
            580                 585                 590

gct aga aat tgc ctt gtt tcc gtg aaa gac tat acc agt cca cgg ata     1824
Ala Arg Asn Cys Leu Val Ser Val Lys Asp Tyr Thr Ser Pro Arg Ile
        595                 600                 605

gtg aag att gga gac ttt gga ctc gcc aga gac atc tat aaa aat gat     1872
```

```
Val Lys Ile Gly Asp Phe Gly Leu Ala Arg Asp Ile Tyr Lys Asn Asp
    610                 615                 620

tac tat aga aag aga ggg gaa ggc ctg ctc cca gtt cgg tgg atg gct     1920
Tyr Tyr Arg Lys Arg Gly Glu Gly Leu Leu Pro Val Arg Trp Met Ala
625                 630                 635                 640

cca gaa agt ttg atg gat gga atc ttc act act caa tct gat gta tgg     1968
Pro Glu Ser Leu Met Asp Gly Ile Phe Thr Thr Gln Ser Asp Val Trp
                645                 650                 655

tct ttt gga att ctg att tgg gag att tta act ctt ggt cat cag cct     2016
Ser Phe Gly Ile Leu Ile Trp Glu Ile Leu Thr Leu Gly His Gln Pro
            660                 665                 670

tat cca gct cat tcc aac ctt gat gtg tta aac tat gtg caa aca gga     2064
Tyr Pro Ala His Ser Asn Leu Asp Val Leu Asn Tyr Val Gln Thr Gly
        675                 680                 685

ggg aga ctg gag cca cca aga aat tgt cct gat gat ctg tgg aat tta     2112
Gly Arg Leu Glu Pro Pro Arg Asn Cys Pro Asp Asp Leu Trp Asn Leu
    690                 695                 700

atg acc cag tgc tgg gct caa gaa ccc gac caa aga cct act ttt cat     2160
Met Thr Gln Cys Trp Ala Gln Glu Pro Asp Gln Arg Pro Thr Phe His
705                 710                 715                 720

aga att cag gac caa ctt cag tta ttc aga aat ttt ttc tta aat agc     2208
Arg Ile Gln Asp Gln Leu Gln Leu Phe Arg Asn Phe Phe Leu Asn Ser
                725                 730                 735

att tat aag tcc aga gat gaa gca aac aac agt gga gtc ata aat gaa     2256
Ile Tyr Lys Ser Arg Asp Glu Ala Asn Asn Ser Gly Val Ile Asn Glu
            740                 745                 750

agc ttt gaa ggt gaa gat ggc gat gtg att tgt ttg aat tca gat gac     2304
Ser Phe Glu Gly Glu Asp Gly Asp Val Ile Cys Leu Asn Ser Asp Asp
        755                 760                 765

att atg cca gtt gct tta atg gaa acg aag aac cga gaa ggg tta aac     2352
Ile Met Pro Val Ala Leu Met Glu Thr Lys Asn Arg Glu Gly Leu Asn
    770                 775                 780

tat atg gta ctt gct aca gaa tgt ggc caa ggt gaa gaa aag tct gag     2400
Tyr Met Val Leu Ala Thr Glu Cys Gly Gln Gly Glu Glu Lys Ser Glu
785                 790                 795                 800

ggt cct cta ggc tcc cag gaa tct gaa tct tgt ggt ctg agg aaa gaa     2448
Gly Pro Leu Gly Ser Gln Glu Ser Glu Ser Cys Gly Leu Arg Lys Glu
                805                 810                 815

gag aag gaa cca cat gca gac aaa gat ttc tgc caa gaa aaa caa gtg     2496
Glu Lys Glu Pro His Ala Asp Lys Asp Phe Cys Gln Glu Lys Gln Val
            820                 825                 830

gct tac tgc cct tct ggc aag cct gaa ggc ctg aac tat gcc tgt ctc     2544
Ala Tyr Cys Pro Ser Gly Lys Pro Glu Gly Leu Asn Tyr Ala Cys Leu
        835                 840                 845

act cac agt gga tat gga gat ggg tct gat taa                         2577
Thr His Ser Gly Tyr Gly Asp Gly Ser Asp
    850                 855


<210> SEQ ID NO 10
<211> LENGTH: 858
<212> TYPE: PRT
<213> ORGANISM: Homo sapiens

<400> SEQUENCE: 10

Met Pro Lys Pro Ile Asn Val Arg Val Thr Thr Met Asp Ala Glu Leu
1               5                   10                  15

Glu Phe Ala Ile Gln Pro Asn Thr Thr Gly Lys Gln Leu Phe Asp Gln
            20                  25                  30

Val Val Lys Thr Ile Gly Leu Arg Glu Val Trp Tyr Phe Gly Leu His
        35                  40                  45
```

```
Tyr Val Asp Asn Lys Gly Phe Pro Thr Trp Leu Lys Leu Asp Lys Lys
    50                  55                  60

Val Ser Ala Gln Glu Val Arg Lys Glu Asn Pro Leu Gln Phe Lys Phe
65                  70                  75                  80

Arg Ala Lys Phe Tyr Pro Glu Asp Val Ala Glu Glu Leu Ile Gln Asp
                85                  90                  95

Ile Thr Gln Lys His Phe Phe Leu Gln Val Lys Glu Gly Ile Leu Ser
            100                 105                 110

Asp Glu Ile Tyr Cys Pro Pro Glu Thr Ala Val Leu Leu Gly Ser Tyr
        115                 120                 125

Ala Val Gln Ala Lys Phe Gly Asp Tyr Asn Lys Glu Val His Lys Ser
    130                 135                 140

Gly Tyr Leu Ser Ser Glu Arg Leu Ile Pro Gln Arg Val Met Asp Gln
145                 150                 155                 160

His Lys Leu Thr Arg Asp Gln Trp Glu Asp Arg Ile Gln Val Trp His
                165                 170                 175

Ala Glu His Arg Gly Met Leu Lys Asp Asn Ala Met Leu Glu Tyr Leu
            180                 185                 190

Lys Ile Ala Gln Asp Leu Glu Met Tyr Gly Ile Asn Tyr Phe Glu Ile
        195                 200                 205

Lys Asn Lys Lys Gly Thr Asp Leu Trp Leu Gly Val Asp Ala Leu Gly
    210                 215                 220

Leu Asn Ile Tyr Glu Lys Asp Asp Lys Leu Thr Pro Lys Ile Gly Phe
225                 230                 235                 240

Pro Trp Ser Glu Ile Arg Asn Ile Ser Phe Asn Asp Lys Lys Phe Val
                245                 250                 255

Ile Lys Pro Ile Asp Lys Lys Ala Pro Asp Phe Val Phe Tyr Ala Pro
            260                 265                 270

Arg Leu Arg Ile Asn Lys Arg Ile Leu Gln Leu Cys Met Gly Asn His
        275                 280                 285

Glu Leu Tyr Met Arg Arg Arg Lys Pro Asp Thr Ile Glu Val Gln Gln
    290                 295                 300

Met Lys Ala Gln Ala Arg Glu Glu Lys His Gln Lys Gln Leu Glu Arg
305                 310                 315                 320

Gln Gln Leu Glu Thr Glu Lys Lys Arg Arg Glu Thr Val Glu Arg Glu
                325                 330                 335

Lys Glu Gln Met Met Arg Glu Lys Glu Glu Leu Met Leu Arg Leu Gln
            340                 345                 350

Asp Tyr Glu Glu Lys Thr Lys Lys Ala Glu Arg Asp Asp Phe Trp Ile
        355                 360                 365

Pro Glu Thr Ser Phe Ile Leu Thr Ile Ile Val Gly Ile Phe Leu Val
    370                 375                 380

Val Thr Ile Pro Leu Thr Phe Val Trp His Arg Arg Leu Lys Asn Gln
385                 390                 395                 400

Lys Ser Ala Lys Glu Gly Val Thr Val Leu Ile Asn Glu Asp Lys Glu
                405                 410                 415

Leu Ala Glu Leu Arg Gly Leu Ala Ala Gly Val Gly Leu Ala Asn Ala
            420                 425                 430

Cys Tyr Ala Ile His Thr Leu Pro Thr Gln Glu Glu Ile Glu Asn Leu
        435                 440                 445

Pro Ala Phe Pro Arg Glu Lys Leu Thr Leu Arg Leu Leu Leu Gly Ser
    450                 455                 460
```

```
Gly Ala Phe Gly Glu Val Tyr Glu Gly Thr Ala Val Asp Ile Leu Gly
465                 470                 475                 480

Val Gly Ser Gly Glu Ile Lys Val Ala Val Lys Thr Leu Lys Lys Gly
                485                 490                 495

Ser Thr Asp Gln Glu Lys Ile Glu Phe Leu Lys Glu Ala His Leu Met
            500                 505                 510

Ser Lys Phe Asn His Pro Asn Ile Leu Lys Gln Leu Gly Val Cys Leu
        515                 520                 525

Leu Asn Glu Pro Gln Tyr Ile Ile Leu Glu Leu Met Glu Gly Gly Asp
    530                 535                 540

Leu Leu Thr Tyr Leu Arg Lys Ala Arg Met Ala Thr Phe Tyr Gly Pro
545                 550                 555                 560

Leu Leu Thr Leu Val Asp Leu Val Asp Leu Cys Val Asp Ile Ser Lys
                565                 570                 575

Gly Cys Val Tyr Leu Glu Arg Met His Phe Ile His Arg Asp Leu Ala
            580                 585                 590

Ala Arg Asn Cys Leu Val Ser Val Lys Asp Tyr Thr Ser Pro Arg Ile
        595                 600                 605

Val Lys Ile Gly Asp Phe Gly Leu Ala Arg Asp Ile Tyr Lys Asn Asp
    610                 615                 620

Tyr Tyr Arg Lys Arg Gly Glu Gly Leu Leu Pro Val Arg Trp Met Ala
625                 630                 635                 640

Pro Glu Ser Leu Met Asp Gly Ile Phe Thr Thr Gln Ser Asp Val Trp
                645                 650                 655

Ser Phe Gly Ile Leu Ile Trp Glu Ile Leu Thr Leu Gly His Gln Pro
            660                 665                 670

Tyr Pro Ala His Ser Asn Leu Asp Val Leu Asn Tyr Val Gln Thr Gly
        675                 680                 685

Gly Arg Leu Glu Pro Pro Arg Asn Cys Pro Asp Asp Leu Trp Asn Leu
    690                 695                 700

Met Thr Gln Cys Trp Ala Gln Glu Pro Asp Gln Arg Pro Thr Phe His
705                 710                 715                 720

Arg Ile Gln Asp Gln Leu Gln Leu Phe Arg Asn Phe Phe Leu Asn Ser
                725                 730                 735

Ile Tyr Lys Ser Arg Asp Glu Ala Asn Asn Ser Gly Val Ile Asn Glu
            740                 745                 750

Ser Phe Glu Gly Glu Asp Gly Asp Val Ile Cys Leu Asn Ser Asp Asp
        755                 760                 765

Ile Met Pro Val Ala Leu Met Glu Thr Lys Asn Arg Glu Gly Leu Asn
    770                 775                 780

Tyr Met Val Leu Ala Thr Glu Cys Gly Gln Gly Glu Glu Lys Ser Glu
785                 790                 795                 800

Gly Pro Leu Gly Ser Gln Glu Ser Glu Ser Cys Gly Leu Arg Lys Glu
                805                 810                 815

Glu Lys Glu Pro His Ala Asp Lys Asp Phe Cys Gln Glu Lys Gln Val
            820                 825                 830

Ala Tyr Cys Pro Ser Gly Lys Pro Glu Gly Leu Asn Tyr Ala Cys Leu
        835                 840                 845

Thr His Ser Gly Tyr Gly Asp Gly Ser Asp
    850                 855
```

<210> SEQ ID NO 11
<211> LENGTH: 3822
<212> TYPE: DNA

```
<213> ORGANISM: Homo sapiens
<220> FEATURE:
<221> NAME/KEY: CDS
<222> LOCATION: (1)..(3822)

<400> SEQUENCE: 11

atg gct ccc tgg cct gaa ttg gga gat gcc cag ccc aac ccc gat aag      48
Met Ala Pro Trp Pro Glu Leu Gly Asp Ala Gln Pro Asn Pro Asp Lys
1               5                   10                  15

tac ctc gaa ggg gcc gca ggt cag cag ccc act gcc cct gat aaa agc      96
Tyr Leu Glu Gly Ala Ala Gly Gln Gln Pro Thr Ala Pro Asp Lys Ser
            20                  25                  30

aaa gag acc aac aaa aca gat aac act gag gca cct gta acc aag att     144
Lys Glu Thr Asn Lys Thr Asp Asn Thr Glu Ala Pro Val Thr Lys Ile
        35                  40                  45

gaa ctt ctg ccg tcc tac tcc acg gct aca ctg ata gat gag ccc act     192
Glu Leu Leu Pro Ser Tyr Ser Thr Ala Thr Leu Ile Asp Glu Pro Thr
    50                  55                  60

gag gtg gat gac ccc tgg aac cta ccc act ctt cag gac tcg ggg atc     240
Glu Val Asp Asp Pro Trp Asn Leu Pro Thr Leu Gln Asp Ser Gly Ile
65                  70                  75                  80

aag tgg tca gag aga gac acc aaa ggg aag att ctc tgt ttc ttc caa     288
Lys Trp Ser Glu Arg Asp Thr Lys Gly Lys Ile Leu Cys Phe Phe Gln
                85                  90                  95

ggg att ggg aga ttg att tta ctt ctc gga ttt ctc tac ttt ttc gtg     336
Gly Ile Gly Arg Leu Ile Leu Leu Leu Gly Phe Leu Tyr Phe Phe Val
            100                 105                 110

tgc tcc ctg gat att ctt agt agc gcc ttc cag ctg gtt gga gga aaa     384
Cys Ser Leu Asp Ile Leu Ser Ser Ala Phe Gln Leu Val Gly Gly Lys
        115                 120                 125

atg gca gga cag ttc ttc agc aac agc tct att atg tcc aac cct ttg     432
Met Ala Gly Gln Phe Phe Ser Asn Ser Ser Ile Met Ser Asn Pro Leu
    130                 135                 140

ttg ggg ctg gtg atc ggg gtg ctg gtg acc gtc ttg gtg cag agc tcc     480
Leu Gly Leu Val Ile Gly Val Leu Val Thr Val Leu Val Gln Ser Ser
145                 150                 155                 160

agc acc tca acg tcc atc gtt gtc agc atg gtg tcc tct tca ttg ctc     528
Ser Thr Ser Thr Ser Ile Val Val Ser Met Val Ser Ser Ser Leu Leu
                165                 170                 175

act gtt cgg gct gcc atc ccc att atc atg ggg gcc aac att gga acg     576
Thr Val Arg Ala Ala Ile Pro Ile Ile Met Gly Ala Asn Ile Gly Thr
            180                 185                 190

tca atc acc aac act att gtt gcg ctc atg cag gtg gga gat cgg agt     624
Ser Ile Thr Asn Thr Ile Val Ala Leu Met Gln Val Gly Asp Arg Ser
        195                 200                 205

gag ttc aga aga gct ttt gca gga gcc act gtc cat gac ttc ttc aac     672
Glu Phe Arg Arg Ala Phe Ala Gly Ala Thr Val His Asp Phe Phe Asn
    210                 215                 220

tgg ctg tcc gtg ttg gtg ctc ttg ccc gtg gag gtg gcc acc cat tac     720
Trp Leu Ser Val Leu Val Leu Leu Pro Val Glu Val Ala Thr His Tyr
225                 230                 235                 240

ctc gag atc ata acc cag ctt ata gtg gag agc ttc cac ttc aag aat     768
Leu Glu Ile Ile Thr Gln Leu Ile Val Glu Ser Phe His Phe Lys Asn
                245                 250                 255

gga gaa gat gcc cca gat ctt ctg aaa gtc atc act aag ccc ttc aca     816
Gly Glu Asp Ala Pro Asp Leu Leu Lys Val Ile Thr Lys Pro Phe Thr
            260                 265                 270

aag ctc att gtc cag ctg gat aaa aaa gtt atc agc caa att gca atg     864
Lys Leu Ile Val Gln Leu Asp Lys Lys Val Ile Ser Gln Ile Ala Met
        275                 280                 285
```

-continued

```
aac gat gaa aaa gcg aaa aac aag agt ctt gtc aag att tgg tgc aaa      912
Asn Asp Glu Lys Ala Lys Asn Lys Ser Leu Val Lys Ile Trp Cys Lys
    290                 295                 300

act ttt acc aac aag acc cag att aac gtc act gtt ccc tcg act gct      960
Thr Phe Thr Asn Lys Thr Gln Ile Asn Val Thr Val Pro Ser Thr Ala
305                 310                 315                 320

aac tgc acc tcc cct tcc ctc tgt tgg acg gat ggc atc caa aac tgg     1008
Asn Cys Thr Ser Pro Ser Leu Cys Trp Thr Asp Gly Ile Gln Asn Trp
                325                 330                 335

acc atg aag aat gtg acc tac aag gag aac atc gcc aaa tgc cag cat     1056
Thr Met Lys Asn Val Thr Tyr Lys Glu Asn Ile Ala Lys Cys Gln His
            340                 345                 350

atc ttt gtg aat ttc cac ctc ccg gat ctt gct gtg ggc acc atc ttg     1104
Ile Phe Val Asn Phe His Leu Pro Asp Leu Ala Val Gly Thr Ile Leu
        355                 360                 365

ctc ata ctc tcc ctg ctg gtc ctc tgt ggt tgc ctg atc atg att gtc     1152
Leu Ile Leu Ser Leu Leu Val Leu Cys Gly Cys Leu Ile Met Ile Val
    370                 375                 380

aag atc ctg ggc tct gtg ctc aag ggg cag gtc gcc act gtc atc aag     1200
Lys Ile Leu Gly Ser Val Leu Lys Gly Gln Val Ala Thr Val Ile Lys
385                 390                 395                 400

aag acc atc aac act gat ttc ccc ttt ccc ttt gca tgg ttg act ggc     1248
Lys Thr Ile Asn Thr Asp Phe Pro Phe Pro Phe Ala Trp Leu Thr Gly
                405                 410                 415

tac ctg gcc atc ctc gtc ggg gca ggc atg acc ttc atc gta cag agc     1296
Tyr Leu Ala Ile Leu Val Gly Ala Gly Met Thr Phe Ile Val Gln Ser
            420                 425                 430

agc tct gtg ttc acg tcg gcc ttg acc ccc ctg att gga atc ggc gtg     1344
Ser Ser Val Phe Thr Ser Ala Leu Thr Pro Leu Ile Gly Ile Gly Val
        435                 440                 445

ata acc att gag agg gct tat cca ctc acg ctg ggc tcc aac atc ggc     1392
Ile Thr Ile Glu Arg Ala Tyr Pro Leu Thr Leu Gly Ser Asn Ile Gly
    450                 455                 460

acc acc acc acc gcc atc ctg gcc gcc tta gcc agc cct ggc aat gca     1440
Thr Thr Thr Thr Ala Ile Leu Ala Ala Leu Ala Ser Pro Gly Asn Ala
465                 470                 475                 480

ttg agg agt tca ctc cag atc gcc ctg tgc cac ttt ttc ttc aac atc     1488
Leu Arg Ser Ser Leu Gln Ile Ala Leu Cys His Phe Phe Phe Asn Ile
                485                 490                 495

tcc ggc atc ttg ctg tgg tac ccg atc ccg ttc act cgc ctg ccc atc     1536
Ser Gly Ile Leu Leu Trp Tyr Pro Ile Pro Phe Thr Arg Leu Pro Ile
            500                 505                 510

cgc atg gcc aag ggg ctg ggc aac atc tct gcc aag tat cgc tgg ttc     1584
Arg Met Ala Lys Gly Leu Gly Asn Ile Ser Ala Lys Tyr Arg Trp Phe
        515                 520                 525

gcc gtc ttc tac ctg atc atc ttc ttc ttc ctg atc ccg ctg acg gtg     1632
Ala Val Phe Tyr Leu Ile Ile Phe Phe Phe Leu Ile Pro Leu Thr Val
    530                 535                 540

ttt ggc ctc tcg ctg gcc ggc tgg cgg gtg ctg gtt ggt gtc ggg gtt     1680
Phe Gly Leu Ser Leu Ala Gly Trp Arg Val Leu Val Gly Val Gly Val
545                 550                 555                 560

ccc gtc gtc ttc atc atc atc ctg gta ctg tgc ctc cga ctc ctg cag     1728
Pro Val Val Phe Ile Ile Ile Leu Val Leu Cys Leu Arg Leu Leu Gln
                565                 570                 575

tct cgc tgc cca cgc gtc ctg ccg aag aaa ctc cag aac tgg aac ttc     1776
Ser Arg Cys Pro Arg Val Leu Pro Lys Lys Leu Gln Asn Trp Asn Phe
            580                 585                 590

ctg ccg ctg tgg atg cgc tcg ctg aag ccc tgg gat gcc gtc gtc tcc     1824
Leu Pro Leu Trp Met Arg Ser Leu Lys Pro Trp Asp Ala Val Val Ser
        595                 600                 605
```

-continued

```
aag ttc acc ggc tgc ttc cag atg cgc tgc tgc tgc tgc tgc cgc gtg      1872
Lys Phe Thr Gly Cys Phe Gln Met Arg Cys Cys Cys Cys Cys Arg Val
    610                 615                 620

tgc tgc cgc gcg tgc tgc ttg ctg tgt ggc tgc ccc aag tgc tgc cgc      1920
Cys Cys Arg Ala Cys Cys Leu Leu Cys Gly Cys Pro Lys Cys Cys Arg
625                 630                 635                 640

tgc agc aag tgc tgc gag gac ttg gag gag gcg cag gag ggg cag gat      1968
Cys Ser Lys Cys Cys Glu Asp Leu Glu Glu Ala Gln Glu Gly Gln Asp
                645                 650                 655

gtc cct gtc aag gct cct gag acc ttt gat aac ata acc att agc aga      2016
Val Pro Val Lys Ala Pro Glu Thr Phe Asp Asn Ile Thr Ile Ser Arg
            660                 665                 670

gag gct cag gct gga gtc cca aat aaa cca ggc att ccc aaa tta cta      2064
Glu Ala Gln Ala Gly Val Pro Asn Lys Pro Gly Ile Pro Lys Leu Leu
        675                 680                 685

gaa ggg agt aaa aat tca ata cag tgg gag aaa gct gaa gat aat gga      2112
Glu Gly Ser Lys Asn Ser Ile Gln Trp Glu Lys Ala Glu Asp Asn Gly
    690                 695                 700

tgt aga att aca tac tat atc ctt gag ata aga aag agc act tca aat      2160
Cys Arg Ile Thr Tyr Tyr Ile Leu Glu Ile Arg Lys Ser Thr Ser Asn
705                 710                 715                 720

aat tta cag aac cag aat tta agg tgg aag atg aca ttt aat gga tcc      2208
Asn Leu Gln Asn Gln Asn Leu Arg Trp Lys Met Thr Phe Asn Gly Ser
                725                 730                 735

tgc agt agt gtt tgc aca tgg aag tcc aaa aac ctg aaa gga ata ttt      2256
Cys Ser Ser Val Cys Thr Trp Lys Ser Lys Asn Leu Lys Gly Ile Phe
            740                 745                 750

cag ttc aga gta gta gct gca aat aat cta ggg ttt ggt gaa tat agt      2304
Gln Phe Arg Val Val Ala Ala Asn Asn Leu Gly Phe Gly Glu Tyr Ser
        755                 760                 765

gga atc agt gag aat att ata tta gtt gga gat gat ttt tgg ata cca      2352
Gly Ile Ser Glu Asn Ile Ile Leu Val Gly Asp Asp Phe Trp Ile Pro
    770                 775                 780

gaa aca agt ttc ata ctt act att ata gtt gga ata ttt ctg gtt gtt      2400
Glu Thr Ser Phe Ile Leu Thr Ile Ile Val Gly Ile Phe Leu Val Val
785                 790                 795                 800

aca atc cca ctg acc ttt gtc tgg cat aga aga tta aag aat caa aaa      2448
Thr Ile Pro Leu Thr Phe Val Trp His Arg Arg Leu Lys Asn Gln Lys
                805                 810                 815

agt gcc aag gaa ggg gtg aca gtg ctt ata aac gaa gac aaa gag ttg      2496
Ser Ala Lys Glu Gly Val Thr Val Leu Ile Asn Glu Asp Lys Glu Leu
            820                 825                 830

gct gag ctg cga ggt ctg gca gcc gga gta ggc ctg gct aat gcc tgc      2544
Ala Glu Leu Arg Gly Leu Ala Ala Gly Val Gly Leu Ala Asn Ala Cys
        835                 840                 845

tat gca ata cat act ctt cca acc caa gag gag att gaa aat ctt cct      2592
Tyr Ala Ile His Thr Leu Pro Thr Gln Glu Glu Ile Glu Asn Leu Pro
    850                 855                 860

gcc ttc cct cgg gaa aaa ctg act ctg cgt ctc ttg ctg gga agt gga      2640
Ala Phe Pro Arg Glu Lys Leu Thr Leu Arg Leu Leu Leu Gly Ser Gly
865                 870                 875                 880

gcc ttt gga gaa gtg tat gaa gga aca gca gtg gac atc tta gga gtt      2688
Ala Phe Gly Glu Val Tyr Glu Gly Thr Ala Val Asp Ile Leu Gly Val
                885                 890                 895

gga agt gga gaa atc aaa gta gca gtg aag act ttg aag aag ggt tcc      2736
Gly Ser Gly Glu Ile Lys Val Ala Val Lys Thr Leu Lys Lys Gly Ser
            900                 905                 910

aca gac cag gag aag att gaa ttc ctg aag gag gca cat ctg atg agc      2784
Thr Asp Gln Glu Lys Ile Glu Phe Leu Lys Glu Ala His Leu Met Ser
```

-continued

```
        915                 920                 925

aaa ttt aat cat ccc aac att ctg aag cag ctt gga gtt tgt ctg ctg      2832
Lys Phe Asn His Pro Asn Ile Leu Lys Gln Leu Gly Val Cys Leu Leu
    930                 935                 940

aat gaa ccc caa tac att atc ctg gaa ctg atg gag gga gga gac ctt      2880
Asn Glu Pro Gln Tyr Ile Ile Leu Glu Leu Met Glu Gly Gly Asp Leu
945                 950                 955                 960

ctt act tat ttg cgt aaa gcc cgg atg gca acg ttt tat ggt cct tta      2928
Leu Thr Tyr Leu Arg Lys Ala Arg Met Ala Thr Phe Tyr Gly Pro Leu
                965                 970                 975

ctc acc ttg gtt gac ctt gta gac ctg tgt gta gat att tca aaa ggc      2976
Leu Thr Leu Val Asp Leu Val Asp Leu Cys Val Asp Ile Ser Lys Gly
            980                 985                 990

tgt gtc tac ttg gaa cgg atg cat  ttc att cac agg gat  ctg gca gct    3024
Cys Val Tyr Leu Glu Arg Met His  Phe Ile His Arg Asp  Leu Ala Ala
        995                 1000                 1005

aga aat  tgc ctt gtt tcc gtg  aaa gac tat acc agt  cca cgg ata      3069
Arg Asn  Cys Leu Val Ser Val  Lys Asp Tyr Thr Ser  Pro Arg Ile
    1010                 1015                 1020

gtg aag  att gga gac ttt gga  ctc gcc aga gac atc  tat aaa aat      3114
Val Lys  Ile Gly Asp Phe Gly  Leu Ala Arg Asp Ile  Tyr Lys Asn
    1025                 1030                 1035

gat tac  tat aga aag aga ggg  gaa ggc ctg ctc cca  gtt cgg tgg      3159
Asp Tyr  Tyr Arg Lys Arg Gly  Glu Gly Leu Leu Pro  Val Arg Trp
    1040                 1045                 1050

atg gct  cca gaa agt ttg atg  gat gga atc ttc act  act caa tct      3204
Met Ala  Pro Glu Ser Leu Met  Asp Gly Ile Phe Thr  Thr Gln Ser
    1055                 1060                 1065

gat gta  tgg tct ttt gga att  ctg att tgg gag att  tta act ctt      3249
Asp Val  Trp Ser Phe Gly Ile  Leu Ile Trp Glu Ile  Leu Thr Leu
    1070                 1075                 1080

ggt cat  cag cct tat cca gct  cat tcc aac ctt gat  gtg tta aac      3294
Gly His  Gln Pro Tyr Pro Ala  His Ser Asn Leu Asp  Val Leu Asn
    1085                 1090                 1095

tat gtg  caa aca gga ggg aga  ctg gag cca cca aga  aat tgt cct      3339
Tyr Val  Gln Thr Gly Gly Arg  Leu Glu Pro Pro Arg  Asn Cys Pro
    1100                 1105                 1110

gat gat  ctg tgg aat tta atg  acc cag tgc tgg gct  caa gaa ccc      3384
Asp Asp  Leu Trp Asn Leu Met  Thr Gln Cys Trp Ala  Gln Glu Pro
    1115                 1120                 1125

gac caa  aga cct act ttt cat  aga att cag gac caa  ctt cag tta      3429
Asp Gln  Arg Pro Thr Phe His  Arg Ile Gln Asp Gln  Leu Gln Leu
    1130                 1135                 1140

ttc aga  aat ttt ttc tta aat  agc att tat aag tcc  aga gat gaa      3474
Phe Arg  Asn Phe Phe Leu Asn  Ser Ile Tyr Lys Ser  Arg Asp Glu
    1145                 1150                 1155

gca aac  aac agt gga gtc ata  aat gaa agc ttt gaa  ggt gaa gat      3519
Ala Asn  Asn Ser Gly Val Ile  Asn Glu Ser Phe Glu  Gly Glu Asp
    1160                 1165                 1170

ggc gat  gtg att tgt ttg aat  tca gat gac att atg  cca gtt gct      3564
Gly Asp  Val Ile Cys Leu Asn  Ser Asp Asp Ile Met  Pro Val Ala
    1175                 1180                 1185

tta atg  gaa acg aag aac cga  gaa ggg tta aac tat  atg gta ctt      3609
Leu Met  Glu Thr Lys Asn Arg  Glu Gly Leu Asn Tyr  Met Val Leu
    1190                 1195                 1200

gct aca  gaa tgt ggc caa ggt  gaa gaa aag tct gag  ggt cct cta      3654
Ala Thr  Glu Cys Gly Gln Gly  Glu Glu Lys Ser Glu  Gly Pro Leu
    1205                 1210                 1215

ggc tcc  cag gaa tct gaa tct  tgt ggt ctg agg aaa  gaa gag aag      3699
```

```
Gly Ser  Gln Glu Ser Glu Ser  Cys Gly Leu Arg Lys  Glu Glu Lys
    1220                1225                1230

gaa cca  cat gca gac aaa gat  ttc tgc caa gaa aaa  caa gtg gct      3744
Glu Pro  His Ala Asp Lys Asp  Phe Cys Gln Glu Lys  Gln Val Ala
    1235                1240                1245

tac tgc  cct tct ggc aag cct  gaa ggc ctg aac tat  gcc tgt ctc      3789
Tyr Cys  Pro Ser Gly Lys Pro  Glu Gly Leu Asn Tyr  Ala Cys Leu
    1250                1255                1260

act cac  agt gga tat gga gat  ggg tct gat taa                      3822
Thr His  Ser Gly Tyr Gly Asp  Gly Ser Asp
    1265                1270


<210> SEQ ID NO 12
<211> LENGTH: 1273
<212> TYPE: PRT
<213> ORGANISM: Homo sapiens

<400> SEQUENCE: 12

Met Ala Pro Trp Pro Glu Leu Gly Asp Ala Gln Pro Asn Pro Asp Lys
1               5                   10                  15

Tyr Leu Glu Gly Ala Ala Gly Gln Gln Pro Thr Ala Pro Asp Lys Ser
            20                  25                  30

Lys Glu Thr Asn Lys Thr Asp Asn Thr Glu Ala Pro Val Thr Lys Ile
        35                  40                  45

Glu Leu Leu Pro Ser Tyr Ser Thr Ala Thr Leu Ile Asp Glu Pro Thr
    50                  55                  60

Glu Val Asp Asp Pro Trp Asn Leu Pro Thr Leu Gln Asp Ser Gly Ile
65                  70                  75                  80

Lys Trp Ser Glu Arg Asp Thr Lys Gly Lys Ile Leu Cys Phe Phe Gln
                85                  90                  95

Gly Ile Gly Arg Leu Ile Leu Leu Leu Gly Phe Leu Tyr Phe Phe Val
            100                 105                 110

Cys Ser Leu Asp Ile Leu Ser Ser Ala Phe Gln Leu Val Gly Gly Lys
        115                 120                 125

Met Ala Gly Gln Phe Phe Ser Asn Ser Ser Ile Met Ser Asn Pro Leu
    130                 135                 140

Leu Gly Leu Val Ile Gly Val Leu Val Thr Val Leu Val Gln Ser Ser
145                 150                 155                 160

Ser Thr Ser Thr Ser Ile Val Val Ser Met Val Ser Ser Ser Leu Leu
                165                 170                 175

Thr Val Arg Ala Ala Ile Pro Ile Ile Met Gly Ala Asn Ile Gly Thr
            180                 185                 190

Ser Ile Thr Asn Thr Ile Val Ala Leu Met Gln Val Gly Asp Arg Ser
        195                 200                 205

Glu Phe Arg Arg Ala Phe Ala Gly Ala Thr Val His Asp Phe Phe Asn
    210                 215                 220

Trp Leu Ser Val Leu Val Leu Leu Pro Val Glu Val Ala Thr His Tyr
225                 230                 235                 240

Leu Glu Ile Ile Thr Gln Leu Ile Val Glu Ser Phe His Phe Lys Asn
                245                 250                 255

Gly Glu Asp Ala Pro Asp Leu Leu Lys Val Ile Thr Lys Pro Phe Thr
            260                 265                 270

Lys Leu Ile Val Gln Leu Asp Lys Lys Val Ile Ser Gln Ile Ala Met
        275                 280                 285

Asn Asp Glu Lys Ala Lys Asn Lys Ser Leu Val Lys Ile Trp Cys Lys
    290                 295                 300
```

```
Thr Phe Thr Asn Lys Thr Gln Ile Asn Val Thr Val Pro Ser Thr Ala
305                 310                 315                 320

Asn Cys Thr Ser Pro Ser Leu Cys Trp Thr Asp Gly Ile Gln Asn Trp
                325                 330                 335

Thr Met Lys Asn Val Thr Tyr Lys Glu Asn Ile Ala Lys Cys Gln His
            340                 345                 350

Ile Phe Val Asn Phe His Leu Pro Asp Leu Ala Val Gly Thr Ile Leu
        355                 360                 365

Leu Ile Leu Ser Leu Leu Val Leu Cys Gly Cys Leu Ile Met Ile Val
    370                 375                 380

Lys Ile Leu Gly Ser Val Leu Lys Gly Gln Val Ala Thr Val Ile Lys
385                 390                 395                 400

Lys Thr Ile Asn Thr Asp Phe Pro Phe Pro Phe Ala Trp Leu Thr Gly
                405                 410                 415

Tyr Leu Ala Ile Leu Val Gly Ala Gly Met Thr Phe Ile Val Gln Ser
            420                 425                 430

Ser Ser Val Phe Thr Ser Ala Leu Thr Pro Leu Ile Gly Ile Gly Val
        435                 440                 445

Ile Thr Ile Glu Arg Ala Tyr Pro Leu Thr Leu Gly Ser Asn Ile Gly
    450                 455                 460

Thr Thr Thr Thr Ala Ile Leu Ala Ala Leu Ala Ser Pro Gly Asn Ala
465                 470                 475                 480

Leu Arg Ser Ser Leu Gln Ile Ala Leu Cys His Phe Phe Phe Asn Ile
                485                 490                 495

Ser Gly Ile Leu Leu Trp Tyr Pro Ile Pro Phe Thr Arg Leu Pro Ile
            500                 505                 510

Arg Met Ala Lys Gly Leu Gly Asn Ile Ser Ala Lys Tyr Arg Trp Phe
        515                 520                 525

Ala Val Phe Tyr Leu Ile Ile Phe Phe Phe Leu Ile Pro Leu Thr Val
    530                 535                 540

Phe Gly Leu Ser Leu Ala Gly Trp Arg Val Leu Val Gly Val Gly Val
545                 550                 555                 560

Pro Val Val Phe Ile Ile Ile Leu Val Leu Cys Leu Arg Leu Leu Gln
                565                 570                 575

Ser Arg Cys Pro Arg Val Leu Pro Lys Lys Leu Gln Asn Trp Asn Phe
            580                 585                 590

Leu Pro Leu Trp Met Arg Ser Leu Lys Pro Trp Asp Ala Val Val Ser
        595                 600                 605

Lys Phe Thr Gly Cys Phe Gln Met Arg Cys Cys Cys Cys Cys Arg Val
    610                 615                 620

Cys Cys Arg Ala Cys Cys Leu Leu Cys Gly Cys Pro Lys Cys Cys Arg
625                 630                 635                 640

Cys Ser Lys Cys Cys Glu Asp Leu Glu Glu Ala Gln Glu Gly Gln Asp
                645                 650                 655

Val Pro Val Lys Ala Pro Glu Thr Phe Asp Asn Ile Thr Ile Ser Arg
            660                 665                 670

Glu Ala Gln Ala Gly Val Pro Asn Lys Pro Gly Ile Pro Lys Leu Leu
        675                 680                 685

Glu Gly Ser Lys Asn Ser Ile Gln Trp Glu Lys Ala Glu Asp Asn Gly
    690                 695                 700

Cys Arg Ile Thr Tyr Tyr Ile Leu Glu Ile Arg Lys Ser Thr Ser Asn
705                 710                 715                 720
```

-continued

```
Asn Leu Gln Asn Gln Asn Leu Arg Trp Lys Met Thr Phe Asn Gly Ser
                725                 730                 735

Cys Ser Ser Val Cys Thr Trp Lys Ser Lys Asn Leu Lys Gly Ile Phe
            740                 745                 750

Gln Phe Arg Val Val Ala Ala Asn Asn Leu Gly Phe Gly Glu Tyr Ser
        755                 760                 765

Gly Ile Ser Glu Asn Ile Ile Leu Val Gly Asp Asp Phe Trp Ile Pro
    770                 775                 780

Glu Thr Ser Phe Ile Leu Thr Ile Ile Val Gly Ile Phe Leu Val Val
785                 790                 795                 800

Thr Ile Pro Leu Thr Phe Val Trp His Arg Arg Leu Lys Asn Gln Lys
                805                 810                 815

Ser Ala Lys Glu Gly Val Thr Val Leu Ile Asn Glu Asp Lys Glu Leu
            820                 825                 830

Ala Glu Leu Arg Gly Leu Ala Ala Gly Val Gly Leu Ala Asn Ala Cys
        835                 840                 845

Tyr Ala Ile His Thr Leu Pro Thr Gln Glu Glu Ile Glu Asn Leu Pro
    850                 855                 860

Ala Phe Pro Arg Glu Lys Leu Thr Leu Arg Leu Leu Leu Gly Ser Gly
865                 870                 875                 880

Ala Phe Gly Glu Val Tyr Glu Gly Thr Ala Val Asp Ile Leu Gly Val
                885                 890                 895

Gly Ser Gly Glu Ile Lys Val Ala Val Lys Thr Leu Lys Lys Gly Ser
            900                 905                 910

Thr Asp Gln Glu Lys Ile Glu Phe Leu Lys Glu Ala His Leu Met Ser
        915                 920                 925

Lys Phe Asn His Pro Asn Ile Leu Lys Gln Leu Gly Val Cys Leu Leu
    930                 935                 940

Asn Glu Pro Gln Tyr Ile Ile Leu Glu Leu Met Glu Gly Gly Asp Leu
945                 950                 955                 960

Leu Thr Tyr Leu Arg Lys Ala Arg Met Ala Thr Phe Tyr Gly Pro Leu
                965                 970                 975

Leu Thr Leu Val Asp Leu Val Asp Leu Cys Val Asp Ile Ser Lys Gly
            980                 985                 990

Cys Val Tyr Leu Glu Arg Met His  Phe Ile His Arg Asp  Leu Ala Ala
        995                 1000                 1005

Arg Asn  Cys Leu Val Ser Val  Lys Asp Tyr Thr Ser  Pro Arg Ile
    1010                 1015                 1020

Val Lys  Ile Gly Asp Phe Gly  Leu Ala Arg Asp Ile  Tyr Lys Asn
    1025                 1030                 1035

Asp Tyr  Tyr Arg Lys Arg Gly  Glu Gly Leu Leu Pro  Val Arg Trp
    1040                 1045                 1050

Met Ala  Pro Glu Ser Leu Met  Asp Gly Ile Phe Thr  Thr Gln Ser
    1055                 1060                 1065

Asp Val  Trp Ser Phe Gly Ile  Leu Ile Trp Glu Ile  Leu Thr Leu
    1070                 1075                 1080

Gly His  Gln Pro Tyr Pro Ala  His Ser Asn Leu Asp  Val Leu Asn
    1085                 1090                 1095

Tyr Val  Gln Thr Gly Gly Arg  Leu Glu Pro Pro Arg  Asn Cys Pro
    1100                 1105                 1110

Asp Asp  Leu Trp Asn Leu Met  Thr Gln Cys Trp Ala  Gln Glu Pro
    1115                 1120                 1125

Asp Gln  Arg Pro Thr Phe His  Arg Ile Gln Asp Gln  Leu Gln Leu
```

-continued

```
    1130                1135                1140

Phe Arg  Asn Phe Phe Leu Asn  Ser Ile Tyr Lys Ser  Arg Asp Glu
    1145                1150                1155

Ala Asn  Asn Ser Gly Val Ile  Asn Glu Ser Phe Glu  Gly Glu Asp
    1160                1165                1170

Gly Asp  Val Ile Cys Leu Asn  Ser Asp Asp Ile Met  Pro Val Ala
    1175                1180                1185

Leu Met  Glu Thr Lys Asn Arg  Glu Gly Leu Asn Tyr  Met Val Leu
    1190                1195                1200

Ala Thr  Glu Cys Gly Gln Gly  Glu Glu Lys Ser Glu  Gly Pro Leu
    1205                1210                1215

Gly Ser  Gln Glu Ser Glu Ser  Cys Gly Leu Arg Lys  Glu Glu Lys
    1220                1225                1230

Glu Pro  His Ala Asp Lys Asp  Phe Cys Gln Glu Lys  Gln Val Ala
    1235                1240                1245

Tyr Cys  Pro Ser Gly Lys Pro  Glu Gly Leu Asn Tyr  Ala Cys Leu
    1250                1255                1260

Thr His  Ser Gly Tyr Gly Asp  Gly Ser Asp
    1265                1270


<210> SEQ ID NO 13
<211> LENGTH: 4098
<212> TYPE: DNA
<213> ORGANISM: Homo sapiens
<220> FEATURE:
<221> NAME/KEY: CDS
<222> LOCATION: (1)..(4098)

<400> SEQUENCE: 13

atg agc gcg ccg agc ctc cgt gcg cgc gcc gcg ggg ttg ggg ctg ctg       48
Met Ser Ala Pro Ser Leu Arg Ala Arg Ala Ala Gly Leu Gly Leu Leu
1               5                   10                  15

ctg tgc gcg gtg ctg ggg cgc gct ggc cgg tca gac agc ggc ggt cgc       96
Leu Cys Ala Val Leu Gly Arg Ala Gly Arg Ser Asp Ser Gly Gly Arg
            20                  25                  30

ggg gaa ctc ggg cag ccc tct ggg gta gcc gcc gag cgc cca tgc ccc      144
Gly Glu Leu Gly Gln Pro Ser Gly Val Ala Ala Glu Arg Pro Cys Pro
        35                  40                  45

act acc tgc cgc tgc ctc ggg gac ctg ctg gac tgc agt cgt aag cgg      192
Thr Thr Cys Arg Cys Leu Gly Asp Leu Leu Asp Cys Ser Arg Lys Arg
    50                  55                  60

cta gcg cgt ctt ccc gag cca ctc ccg tcc tgg gtc gct cgg ctg gac      240
Leu Ala Arg Leu Pro Glu Pro Leu Pro Ser Trp Val Ala Arg Leu Asp
65                  70                  75                  80

tta agt cac aac aga tta tct ttc atc aag gca agt tcc atg agc cac      288
Leu Ser His Asn Arg Leu Ser Phe Ile Lys Ala Ser Ser Met Ser His
                85                  90                  95

ctt caa agc ctt cga gaa gtg aaa ctg aac aac aat gaa ttg gag acc      336
Leu Gln Ser Leu Arg Glu Val Lys Leu Asn Asn Asn Glu Leu Glu Thr
            100                 105                 110

att cca aat ctg gga cca gtc tcg gca aat att aca ctt ctc tcc ttg      384
Ile Pro Asn Leu Gly Pro Val Ser Ala Asn Ile Thr Leu Leu Ser Leu
        115                 120                 125

gct gga aac agg att gtt gaa ata ctc cct gaa cat ctg aaa gag ttt      432
Ala Gly Asn Arg Ile Val Glu Ile Leu Pro Glu His Leu Lys Glu Phe
    130                 135                 140

cag tcc ctt gaa act ttg gac ctt agc agc aac aat att tca gag ctc      480
Gln Ser Leu Glu Thr Leu Asp Leu Ser Ser Asn Asn Ile Ser Glu Leu
145                 150                 155                 160
```

-continued

```
caa act gca ttt cca gcc cta cag ctc aaa tat ctg tat ctc aac agc      528
Gln Thr Ala Phe Pro Ala Leu Gln Leu Lys Tyr Leu Tyr Leu Asn Ser
                165                 170                 175

aac cga gtc aca tca atg gaa cct ggg tat ttt gac aat ttg gcc aac      576
Asn Arg Val Thr Ser Met Glu Pro Gly Tyr Phe Asp Asn Leu Ala Asn
            180                 185                 190

aca ctc ctt gtg tta aag ctg aac agg aac cga atc tca gct atc cca      624
Thr Leu Leu Val Leu Lys Leu Asn Arg Asn Arg Ile Ser Ala Ile Pro
        195                 200                 205

ccc aag atg ttt aaa ctg ccc caa ctg caa cat ctc gaa ttg aac cga      672
Pro Lys Met Phe Lys Leu Pro Gln Leu Gln His Leu Glu Leu Asn Arg
    210                 215                 220

aac aag att aaa aat gta gat gga ctg aca ttc caa ggc ctt ggt gct      720
Asn Lys Ile Lys Asn Val Asp Gly Leu Thr Phe Gln Gly Leu Gly Ala
225                 230                 235                 240

ctg aag tct ctg aaa atg caa aga aat gga gta acg aaa ctt atg gat      768
Leu Lys Ser Leu Lys Met Gln Arg Asn Gly Val Thr Lys Leu Met Asp
                245                 250                 255

gga gct ttt tgg ggg ctg agc aac atg gaa att ttg cag ctg gac cat      816
Gly Ala Phe Trp Gly Leu Ser Asn Met Glu Ile Leu Gln Leu Asp His
            260                 265                 270

aac aac cta aca gag att acc aaa ggc tgg ctt tac ggc ttg ctg atg      864
Asn Asn Leu Thr Glu Ile Thr Lys Gly Trp Leu Tyr Gly Leu Leu Met
        275                 280                 285

ctg cag gaa ctt cat ctc agc caa aat gcc atc aac agg atc agc cct      912
Leu Gln Glu Leu His Leu Ser Gln Asn Ala Ile Asn Arg Ile Ser Pro
    290                 295                 300

gat gcc tgg gag ttc tgc cag aag ctc agt gag ctg gac cta act ttc      960
Asp Ala Trp Glu Phe Cys Gln Lys Leu Ser Glu Leu Asp Leu Thr Phe
305                 310                 315                 320

aat cac tta tca agg tta gat gat tca agc ttc ctt ggc cta agc tta     1008
Asn His Leu Ser Arg Leu Asp Asp Ser Ser Phe Leu Gly Leu Ser Leu
                325                 330                 335

cta aat aca ctg cac att ggg aac aac aga gtc agc tac att gct gat     1056
Leu Asn Thr Leu His Ile Gly Asn Asn Arg Val Ser Tyr Ile Ala Asp
            340                 345                 350

tgt gcc ttc cgg ggg ctt tcc agt tta aag act ttg gat ctg aag aac     1104
Cys Ala Phe Arg Gly Leu Ser Ser Leu Lys Thr Leu Asp Leu Lys Asn
        355                 360                 365

aat gaa att tcc tgg act att gaa gac atg aat ggt gct ttc tct ggg     1152
Asn Glu Ile Ser Trp Thr Ile Glu Asp Met Asn Gly Ala Phe Ser Gly
    370                 375                 380

ctt gac aaa ctg agg cga ctg ata ctc caa gga aat cgg atc cgt tct     1200
Leu Asp Lys Leu Arg Arg Leu Ile Leu Gln Gly Asn Arg Ile Arg Ser
385                 390                 395                 400

att act aaa aaa gcc ttc act ggt ttg gat gca ttg gag cat cta gac     1248
Ile Thr Lys Lys Ala Phe Thr Gly Leu Asp Ala Leu Glu His Leu Asp
                405                 410                 415

ctg agt gac aac gca atc atg tct tta caa ggc aat gca ttt tca caa     1296
Leu Ser Asp Asn Ala Ile Met Ser Leu Gln Gly Asn Ala Phe Ser Gln
            420                 425                 430

atg aag aaa ctg caa caa ttg cat tta aat aca tca agc ctt ttg tgc     1344
Met Lys Lys Leu Gln Gln Leu His Leu Asn Thr Ser Ser Leu Leu Cys
        435                 440                 445

gat tgc cag cta aaa tgg ctc cca cag tgg gtg gcg gaa aac aac ttt     1392
Asp Cys Gln Leu Lys Trp Leu Pro Gln Trp Val Ala Glu Asn Asn Phe
    450                 455                 460

cag agc ttt gta aat gcc agt tgt gcc cat cct cag ctg cta aaa gga     1440
Gln Ser Phe Val Asn Ala Ser Cys Ala His Pro Gln Leu Leu Lys Gly
```

```
465                 470                 475                 480

aga agc att ttt gct gtt agc cca gat ggc ttt gtg tgt gat gat ttt      1488
Arg Ser Ile Phe Ala Val Ser Pro Asp Gly Phe Val Cys Asp Asp Phe
                485                 490                 495

ccc aaa ccc cag atc acg gtt cag cca gaa aca cag tcg gca ata aaa      1536
Pro Lys Pro Gln Ile Thr Val Gln Pro Glu Thr Gln Ser Ala Ile Lys
            500                 505                 510

ggt tcc aat ttg agt ttc atc tgc tca gct gcc agc agc agt gat tcc      1584
Gly Ser Asn Leu Ser Phe Ile Cys Ser Ala Ala Ser Ser Ser Asp Ser
        515                 520                 525

cca atg act ttt gct tgg aaa aaa gac aat gaa cta ctg cat gat gct      1632
Pro Met Thr Phe Ala Trp Lys Lys Asp Asn Glu Leu Leu His Asp Ala
    530                 535                 540

gaa atg gaa aat tat gca cac ctc cgg gcc caa ggt ggc gag gtg atg      1680
Glu Met Glu Asn Tyr Ala His Leu Arg Ala Gln Gly Gly Glu Val Met
545                 550                 555                 560

gag tat acc acc atc ctt cgg ctg cgc gag gtg gaa ttt gcc agt gag      1728
Glu Tyr Thr Thr Ile Leu Arg Leu Arg Glu Val Glu Phe Ala Ser Glu
                565                 570                 575

ggg aaa tat cag tgt gtc atc tcc aat cac ttt ggt tca tcc tac tct      1776
Gly Lys Tyr Gln Cys Val Ile Ser Asn His Phe Gly Ser Ser Tyr Ser
            580                 585                 590

gtc aaa gcc aag ctt aca gta aat atg ctt ccc tca ttc acc aag acc      1824
Val Lys Ala Lys Leu Thr Val Asn Met Leu Pro Ser Phe Thr Lys Thr
        595                 600                 605

ccc atg gat ctc acc atc cga gct ggg gcc atg gca cgc ttg gag tgt      1872
Pro Met Asp Leu Thr Ile Arg Ala Gly Ala Met Ala Arg Leu Glu Cys
    610                 615                 620

gct gct gtg ggg cac cca gcc ccc cag ata gcc tgg cag aag gat ggg      1920
Ala Ala Val Gly His Pro Ala Pro Gln Ile Ala Trp Gln Lys Asp Gly
625                 630                 635                 640

ggc aca gac ttc cca gct gca cgg gag aga cgc atg cat gtg atg ccc      1968
Gly Thr Asp Phe Pro Ala Ala Arg Glu Arg Arg Met His Val Met Pro
                645                 650                 655

gag gat gac gtg ttc ttt atc gtg gat gtg aag ata gag gac att ggg      2016
Glu Asp Asp Val Phe Phe Ile Val Asp Val Lys Ile Glu Asp Ile Gly
            660                 665                 670

gta tac agc tgc aca gct cag aac agt gca gga agt att tca gca aat      2064
Val Tyr Ser Cys Thr Ala Gln Asn Ser Ala Gly Ser Ile Ser Ala Asn
        675                 680                 685

gca act ctg act gtc cta gaa aca cca tca ttt ttg cgg cca ctg ttg      2112
Ala Thr Leu Thr Val Leu Glu Thr Pro Ser Phe Leu Arg Pro Leu Leu
    690                 695                 700

gac cga act gta acc aag gga gaa aca gcc gtc cta cag tgc att gct      2160
Asp Arg Thr Val Thr Lys Gly Glu Thr Ala Val Leu Gln Cys Ile Ala
705                 710                 715                 720

gga gga agc cct ccc cct aaa ctg aac tgg acc aaa gat gat agc cca      2208
Gly Gly Ser Pro Pro Pro Lys Leu Asn Trp Thr Lys Asp Asp Ser Pro
                725                 730                 735

ttg gtg gta acc gag agg cac ttt ttt gca gca ggc aat cag ctt ctg      2256
Leu Val Val Thr Glu Arg His Phe Phe Ala Ala Gly Asn Gln Leu Leu
            740                 745                 750

att att gtg gac tca gat gtc agt gat gct ggg aaa tac aca tgt gag      2304
Ile Ile Val Asp Ser Asp Val Ser Asp Ala Gly Lys Tyr Thr Cys Glu
        755                 760                 765

atg tct aac acc ctt ggc act gag aga gga aac gtg cgc ctc agt gtg      2352
Met Ser Asn Thr Leu Gly Thr Glu Arg Gly Asn Val Arg Leu Ser Val
    770                 775                 780

atc ccc act cca acc tgc gac tcc cct cag atg aca gcc cca tcg tta      2400
```

-continued

```
Ile Pro Thr Pro Thr Cys Asp Ser Pro Gln Met Thr Ala Pro Ser Leu
785                 790                 795                 800

gac gat gac gga tgg gcc act gtg ggt gtc gtg atc ata gcc gtg gtt      2448
Asp Asp Asp Gly Trp Ala Thr Val Gly Val Val Ile Ile Ala Val Val
                805                 810                 815

tgc tgt gtg gtg ggc acg tca ctc gtg tgg gtg gtc atc ata tac cac      2496
Cys Cys Val Val Gly Thr Ser Leu Val Trp Val Val Ile Ile Tyr His
            820                 825                 830

aca agg cgg agg aat gaa gat tgc agc att acc aac aca gat gag acc      2544
Thr Arg Arg Arg Asn Glu Asp Cys Ser Ile Thr Asn Thr Asp Glu Thr
        835                 840                 845

aac ttg cca gca gat att cct agt tat ttg tca tct cag gga acg tta      2592
Asn Leu Pro Ala Asp Ile Pro Ser Tyr Leu Ser Ser Gln Gly Thr Leu
    850                 855                 860

gct gac agg cag gat ggg tac gtg tct tca gaa agt gga agc cac cac      2640
Ala Asp Arg Gln Asp Gly Tyr Val Ser Ser Glu Ser Gly Ser His His
865                 870                 875                 880

cag ttt gtc aca tct tca ggt gct gga ttt ttc tta cca caa cat gac      2688
Gln Phe Val Thr Ser Ser Gly Ala Gly Phe Phe Leu Pro Gln His Asp
                885                 890                 895

agt agt gtc tgg cat aga aga tta aag aat caa aaa agt gcc aag gaa      2736
Ser Ser Val Trp His Arg Arg Leu Lys Asn Gln Lys Ser Ala Lys Glu
            900                 905                 910

ggg gtg aca gtg ctt ata aac gaa gac aaa gag ttg gct gag ctg cga      2784
Gly Val Thr Val Leu Ile Asn Glu Asp Lys Glu Leu Ala Glu Leu Arg
        915                 920                 925

ggt ctg gca gct gga gta ggc ctg gct aat gcc tgc tat gca ata cat      2832
Gly Leu Ala Ala Gly Val Gly Leu Ala Asn Ala Cys Tyr Ala Ile His
    930                 935                 940

act ctt cca acc caa gag gag att gaa aat ctt cct gcc ttc cct cgg      2880
Thr Leu Pro Thr Gln Glu Glu Ile Glu Asn Leu Pro Ala Phe Pro Arg
945                 950                 955                 960

gaa aaa ctg act ctg cgt ctc ttg ctg gga agt gga gcc ttt gga gaa      2928
Glu Lys Leu Thr Leu Arg Leu Leu Leu Gly Ser Gly Ala Phe Gly Glu
                965                 970                 975

gtg tat gaa gga aca gca gtg gac atc tta gga gtt gga agt gga gaa      2976
Val Tyr Glu Gly Thr Ala Val Asp Ile Leu Gly Val Gly Ser Gly Glu
            980                 985                 990

atc aaa gta gca gtg aag act ttg  aag aag ggt tcc aca  gac cag gag    3024
Ile Lys Val Ala Val Lys Thr Leu  Lys Lys Gly Ser Thr  Asp Gln Glu
        995                 1000                1005

aag att  gaa ttc ctg aag gag  gca cat ctg atg agc  aaa ttt aat       3069
Lys Ile  Glu Phe Leu Lys Glu  Ala His Leu Met Ser  Lys Phe Asn
    1010                 1015                 1020

cat ccc  aac att ctg aag cag  ctt gga gtt tgt ctg  ctg aat gaa       3114
His Pro  Asn Ile Leu Lys Gln  Leu Gly Val Cys Leu  Leu Asn Glu
    1025                 1030                 1035

ccc caa  tac att atc ctg gaa  ctg atg gag gga gga  gac ctt ctt       3159
Pro Gln  Tyr Ile Ile Leu Glu  Leu Met Glu Gly Gly  Asp Leu Leu
    1040                 1045                 1050

act tat  ttg cgt aaa gcc cgg  atg gca acg ttt tat  ggt cct tta       3204
Thr Tyr  Leu Arg Lys Ala Arg  Met Ala Thr Phe Tyr  Gly Pro Leu
    1055                 1060                 1065

ctc acc  ttg gtt gac ctt gta  gac ctg tgt gta gat  att tca aaa       3249
Leu Thr  Leu Val Asp Leu Val  Asp Leu Cys Val Asp  Ile Ser Lys
    1070                 1075                 1080

ggc tgt  gtc tac ttg gaa cgg  atg cat ttc att cac  agg gat ctg       3294
Gly Cys  Val Tyr Leu Glu Arg  Met His Phe Ile His  Arg Asp Leu
    1085                 1090                 1095
```

```
gca gct  aga aat tgc ctt gtt  tcc gtg aaa gac tat  acc agt cca      3339
Ala Ala  Arg Asn Cys Leu Val  Ser Val Lys Asp Tyr  Thr Ser Pro
    1100                 1105                 1110

cgg ata  gtg aag att gga gac  ttt gga ctc gcc aga  gac atc tat      3384
Arg Ile  Val Lys Ile Gly Asp  Phe Gly Leu Ala Arg  Asp Ile Tyr
    1115                 1120                 1125

aaa aat  gat tac tat aga aag  aga ggg gaa ggc ctg  ctc cca gtt      3429
Lys Asn  Asp Tyr Tyr Arg Lys  Arg Gly Glu Gly Leu  Leu Pro Val
    1130                 1135                 1140

cgg tgg  atg gct cca gaa agt  ttg atg gat gga atc  ttc act act      3474
Arg Trp  Met Ala Pro Glu Ser  Leu Met Asp Gly Ile  Phe Thr Thr
    1145                 1150                 1155

caa tct  gat gta tgg tct ttt  gga att ctg att tgg  gag att tta      3519
Gln Ser  Asp Val Trp Ser Phe  Gly Ile Leu Ile Trp  Glu Ile Leu
    1160                 1165                 1170

act ctt  ggt cat cag cct tat  cca gct cat tcc aac  ctt gat gtg      3564
Thr Leu  Gly His Gln Pro Tyr  Pro Ala His Ser Asn  Leu Asp Val
    1175                 1180                 1185

tta aac  tat gtg caa aca gga  ggg aga ctg gag cca  cca aga aat      3609
Leu Asn  Tyr Val Gln Thr Gly  Gly Arg Leu Glu Pro  Pro Arg Asn
    1190                 1195                 1200

tgt cct  gat gat ctg tgg aat  tta atg acc cag tgc  tgg gct caa      3654
Cys Pro  Asp Asp Leu Trp Asn  Leu Met Thr Gln Cys  Trp Ala Gln
    1205                 1210                 1215

gaa ccc  gac caa aga cct act  ttt cat aga att cag  gac caa ctt      3699
Glu Pro  Asp Gln Arg Pro Thr  Phe His Arg Ile Gln  Asp Gln Leu
    1220                 1225                 1230

cag tta  ttc aga aat ttt ttc  tta aat agc att tat  aag tcc aga      3744
Gln Leu  Phe Arg Asn Phe Phe  Leu Asn Ser Ile Tyr  Lys Ser Arg
    1235                 1240                 1245

gat gaa  gca aac aac agt gga  gtc ata aat gaa agc  ttt gaa ggt      3789
Asp Glu  Ala Asn Asn Ser Gly  Val Ile Asn Glu Ser  Phe Glu Gly
    1250                 1255                 1260

gaa gat  ggc gat gtg att tgt  ttg aat tca gat gac  att atg cca      3834
Glu Asp  Gly Asp Val Ile Cys  Leu Asn Ser Asp Asp  Ile Met Pro
    1265                 1270                 1275

gtt gct  tta atg gaa acg aag  aac cga gaa ggg tta  aac tat atg      3879
Val Ala  Leu Met Glu Thr Lys  Asn Arg Glu Gly Leu  Asn Tyr Met
    1280                 1285                 1290

gta ctt  gct aca gaa tgt ggc  caa ggt gaa gaa aag  tct gag ggt      3924
Val Leu  Ala Thr Glu Cys Gly  Gln Gly Glu Glu Lys  Ser Glu Gly
    1295                 1300                 1305

cct cta  ggc tcc cag gaa tct  gaa tct tgt ggt ctg  agg aaa gaa      3969
Pro Leu  Gly Ser Gln Glu Ser  Glu Ser Cys Gly Leu  Arg Lys Glu
    1310                 1315                 1320

gag aag  gaa cca cat gca gac  aaa gat ttc tgc caa  gaa aaa caa      4014
Glu Lys  Glu Pro His Ala Asp  Lys Asp Phe Cys Gln  Glu Lys Gln
    1325                 1330                 1335

gtg gct  tac tgc cct tct ggc  aag cct gaa ggc ctg  aac tat gcc      4059
Val Ala  Tyr Cys Pro Ser Gly  Lys Pro Glu Gly Leu  Asn Tyr Ala
    1340                 1345                 1350

tgt ctc  act cac agt gga tat  gga gat ggg tct gat  taa              4098
Cys Leu  Thr His Ser Gly Tyr  Gly Asp Gly Ser Asp
    1355                 1360                 1365
```

<210> SEQ ID NO 14
<211> LENGTH: 1365
<212> TYPE: PRT
<213> ORGANISM: Homo sapiens

<400> SEQUENCE: 14

-continued

```
Met Ser Ala Pro Ser Leu Arg Ala Arg Ala Ala Gly Leu Gly Leu Leu
1               5                   10                  15

Leu Cys Ala Val Leu Gly Arg Ala Gly Arg Ser Asp Ser Gly Gly Arg
            20                  25                  30

Gly Glu Leu Gly Gln Pro Ser Gly Val Ala Ala Glu Arg Pro Cys Pro
        35                  40                  45

Thr Thr Cys Arg Cys Leu Gly Asp Leu Leu Asp Cys Ser Arg Lys Arg
    50                  55                  60

Leu Ala Arg Leu Pro Glu Pro Leu Pro Ser Trp Val Ala Arg Leu Asp
65                  70                  75                  80

Leu Ser His Asn Arg Leu Ser Phe Ile Lys Ala Ser Ser Met Ser His
                85                  90                  95

Leu Gln Ser Leu Arg Glu Val Lys Leu Asn Asn Asn Glu Leu Glu Thr
            100                 105                 110

Ile Pro Asn Leu Gly Pro Val Ser Ala Asn Ile Thr Leu Leu Ser Leu
        115                 120                 125

Ala Gly Asn Arg Ile Val Glu Ile Leu Pro Glu His Leu Lys Glu Phe
    130                 135                 140

Gln Ser Leu Glu Thr Leu Asp Leu Ser Ser Asn Asn Ile Ser Glu Leu
145                 150                 155                 160

Gln Thr Ala Phe Pro Ala Leu Gln Leu Lys Tyr Leu Tyr Leu Asn Ser
                165                 170                 175

Asn Arg Val Thr Ser Met Glu Pro Gly Tyr Phe Asp Asn Leu Ala Asn
            180                 185                 190

Thr Leu Leu Val Leu Lys Leu Asn Arg Asn Arg Ile Ser Ala Ile Pro
        195                 200                 205

Pro Lys Met Phe Lys Leu Pro Gln Leu Gln His Leu Glu Leu Asn Arg
    210                 215                 220

Asn Lys Ile Lys Asn Val Asp Gly Leu Thr Phe Gln Gly Leu Gly Ala
225                 230                 235                 240

Leu Lys Ser Leu Lys Met Gln Arg Asn Gly Val Thr Lys Leu Met Asp
                245                 250                 255

Gly Ala Phe Trp Gly Leu Ser Asn Met Glu Ile Leu Gln Leu Asp His
            260                 265                 270

Asn Asn Leu Thr Glu Ile Thr Lys Gly Trp Leu Tyr Gly Leu Leu Met
        275                 280                 285

Leu Gln Glu Leu His Leu Ser Gln Asn Ala Ile Asn Arg Ile Ser Pro
    290                 295                 300

Asp Ala Trp Glu Phe Cys Gln Lys Leu Ser Glu Leu Asp Leu Thr Phe
305                 310                 315                 320

Asn His Leu Ser Arg Leu Asp Asp Ser Ser Phe Leu Gly Leu Ser Leu
                325                 330                 335

Leu Asn Thr Leu His Ile Gly Asn Asn Arg Val Ser Tyr Ile Ala Asp
            340                 345                 350

Cys Ala Phe Arg Gly Leu Ser Ser Leu Lys Thr Leu Asp Leu Lys Asn
        355                 360                 365

Asn Glu Ile Ser Trp Thr Ile Glu Asp Met Asn Gly Ala Phe Ser Gly
    370                 375                 380

Leu Asp Lys Leu Arg Arg Leu Ile Leu Gln Gly Asn Arg Ile Arg Ser
385                 390                 395                 400

Ile Thr Lys Lys Ala Phe Thr Gly Leu Asp Ala Leu Glu His Leu Asp
                405                 410                 415
```

```
Leu Ser Asp Asn Ala Ile Met Ser Leu Gln Gly Asn Ala Phe Ser Gln
            420                 425                 430

Met Lys Lys Leu Gln Gln Leu His Leu Asn Thr Ser Ser Leu Leu Cys
        435                 440                 445

Asp Cys Gln Leu Lys Trp Leu Pro Gln Trp Val Ala Glu Asn Asn Phe
    450                 455                 460

Gln Ser Phe Val Asn Ala Ser Cys Ala His Pro Gln Leu Leu Lys Gly
465                 470                 475                 480

Arg Ser Ile Phe Ala Val Ser Pro Asp Gly Phe Val Cys Asp Asp Phe
                485                 490                 495

Pro Lys Pro Gln Ile Thr Val Gln Pro Glu Thr Gln Ser Ala Ile Lys
            500                 505                 510

Gly Ser Asn Leu Ser Phe Ile Cys Ser Ala Ala Ser Ser Ser Asp Ser
        515                 520                 525

Pro Met Thr Phe Ala Trp Lys Lys Asp Asn Glu Leu Leu His Asp Ala
    530                 535                 540

Glu Met Glu Asn Tyr Ala His Leu Arg Ala Gln Gly Gly Glu Val Met
545                 550                 555                 560

Glu Tyr Thr Thr Ile Leu Arg Leu Arg Glu Val Glu Phe Ala Ser Glu
                565                 570                 575

Gly Lys Tyr Gln Cys Val Ile Ser Asn His Phe Gly Ser Ser Tyr Ser
            580                 585                 590

Val Lys Ala Lys Leu Thr Val Asn Met Leu Pro Ser Phe Thr Lys Thr
        595                 600                 605

Pro Met Asp Leu Thr Ile Arg Ala Gly Ala Met Ala Arg Leu Glu Cys
    610                 615                 620

Ala Ala Val Gly His Pro Ala Pro Gln Ile Ala Trp Gln Lys Asp Gly
625                 630                 635                 640

Gly Thr Asp Phe Pro Ala Ala Arg Glu Arg Arg Met His Val Met Pro
                645                 650                 655

Glu Asp Asp Val Phe Phe Ile Val Asp Val Lys Ile Glu Asp Ile Gly
            660                 665                 670

Val Tyr Ser Cys Thr Ala Gln Asn Ser Ala Gly Ser Ile Ser Ala Asn
        675                 680                 685

Ala Thr Leu Thr Val Leu Glu Thr Pro Ser Phe Leu Arg Pro Leu Leu
    690                 695                 700

Asp Arg Thr Val Thr Lys Gly Glu Thr Ala Val Leu Gln Cys Ile Ala
705                 710                 715                 720

Gly Gly Ser Pro Pro Pro Lys Leu Asn Trp Thr Lys Asp Asp Ser Pro
                725                 730                 735

Leu Val Val Thr Glu Arg His Phe Phe Ala Ala Gly Asn Gln Leu Leu
            740                 745                 750

Ile Ile Val Asp Ser Asp Val Ser Asp Ala Gly Lys Tyr Thr Cys Glu
        755                 760                 765

Met Ser Asn Thr Leu Gly Thr Glu Arg Gly Asn Val Arg Leu Ser Val
    770                 775                 780

Ile Pro Thr Pro Thr Cys Asp Ser Pro Gln Met Thr Ala Pro Ser Leu
785                 790                 795                 800

Asp Asp Asp Gly Trp Ala Thr Val Gly Val Val Ile Ile Ala Val Val
                805                 810                 815

Cys Cys Val Val Gly Thr Ser Leu Val Trp Val Val Ile Ile Tyr His
            820                 825                 830

Thr Arg Arg Arg Asn Glu Asp Cys Ser Ile Thr Asn Thr Asp Glu Thr
```

-continued

```
        835                 840                 845

Asn Leu Pro Ala Asp Ile Pro Ser Tyr Leu Ser Ser Gln Gly Thr Leu
    850                 855                 860

Ala Asp Arg Gln Asp Gly Tyr Val Ser Ser Glu Ser Gly Ser His His
865                 870                 875                 880

Gln Phe Val Thr Ser Ser Gly Ala Gly Phe Phe Leu Pro Gln His Asp
                885                 890                 895

Ser Ser Val Trp His Arg Arg Leu Lys Asn Gln Lys Ser Ala Lys Glu
            900                 905                 910

Gly Val Thr Val Leu Ile Asn Glu Asp Lys Glu Leu Ala Glu Leu Arg
        915                 920                 925

Gly Leu Ala Ala Gly Val Gly Leu Ala Asn Ala Cys Tyr Ala Ile His
    930                 935                 940

Thr Leu Pro Thr Gln Glu Glu Ile Glu Asn Leu Pro Ala Phe Pro Arg
945                 950                 955                 960

Glu Lys Leu Thr Leu Arg Leu Leu Leu Gly Ser Gly Ala Phe Gly Glu
                965                 970                 975

Val Tyr Glu Gly Thr Ala Val Asp Ile Leu Gly Val Gly Ser Gly Glu
            980                 985                 990

Ile Lys Val Ala Val Lys Thr Leu  Lys Lys Gly Ser Thr  Asp Gln Glu
        995                 1000                1005

Lys Ile  Glu Phe Leu Lys Glu  Ala His Leu Met Ser  Lys Phe Asn
    1010                 1015                1020

His Pro  Asn Ile Leu Lys Gln  Leu Gly Val Cys Leu  Leu Asn Glu
    1025                 1030                1035

Pro Gln  Tyr Ile Ile Leu Glu  Leu Met Glu Gly Gly  Asp Leu Leu
    1040                 1045                1050

Thr Tyr  Leu Arg Lys Ala Arg  Met Ala Thr Phe Tyr  Gly Pro Leu
    1055                 1060                1065

Leu Thr  Leu Val Asp Leu Val  Asp Leu Cys Val Asp  Ile Ser Lys
    1070                 1075                1080

Gly Cys  Val Tyr Leu Glu Arg  Met His Phe Ile His  Arg Asp Leu
    1085                 1090                1095

Ala Ala  Arg Asn Cys Leu Val  Ser Val Lys Asp Tyr  Thr Ser Pro
    1100                 1105                1110

Arg Ile  Val Lys Ile Gly Asp  Phe Gly Leu Ala Arg  Asp Ile Tyr
    1115                 1120                1125

Lys Asn  Asp Tyr Tyr Arg Lys  Arg Gly Glu Gly Leu  Leu Pro Val
    1130                 1135                1140

Arg Trp  Met Ala Pro Glu Ser  Leu Met Asp Gly Ile  Phe Thr Thr
    1145                 1150                1155

Gln Ser  Asp Val Trp Ser Phe  Gly Ile Leu Ile Trp  Glu Ile Leu
    1160                 1165                1170

Thr Leu  Gly His Gln Pro Tyr  Pro Ala His Ser Asn  Leu Asp Val
    1175                 1180                1185

Leu Asn  Tyr Val Gln Thr Gly  Gly Arg Leu Glu Pro  Pro Arg Asn
    1190                 1195                1200

Cys Pro  Asp Asp Leu Trp Asn  Leu Met Thr Gln Cys  Trp Ala Gln
    1205                 1210                1215

Glu Pro  Asp Gln Arg Pro Thr  Phe His Arg Ile Gln  Asp Gln Leu
    1220                 1225                1230

Gln Leu  Phe Arg Asn Phe Phe  Leu Asn Ser Ile Tyr  Lys Ser Arg
    1235                 1240                1245
```

```
Asp Glu  Ala Asn Asn Ser Gly  Val Ile Asn Glu Ser  Phe Glu Gly
    1250                 1255                 1260

Glu Asp  Gly Asp Val Ile Cys  Leu Asn Ser Asp Asp  Ile Met Pro
    1265                 1270                 1275

Val Ala  Leu Met Glu Thr Lys  Asn Arg Glu Gly Leu  Asn Tyr Met
    1280                 1285                 1290

Val Leu  Ala Thr Glu Cys Gly  Gln Gly Glu Glu Lys  Ser Glu Gly
    1295                 1300                 1305

Pro Leu  Gly Ser Gln Glu Ser  Glu Ser Cys Gly Leu  Arg Lys Glu
    1310                 1315                 1320

Glu Lys  Glu Pro His Ala Asp  Lys Asp Phe Cys Gln  Glu Lys Gln
    1325                 1330                 1335

Val Ala  Tyr Cys Pro Ser Gly  Lys Pro Glu Gly Leu  Asn Tyr Ala
    1340                 1345                 1350

Cys Leu  Thr His Ser Gly Tyr  Gly Asp Gly Ser Asp
    1355                 1360                 1365


<210> SEQ ID NO 15
<211> LENGTH: 2178
<212> TYPE: DNA
<213> ORGANISM: Homo sapiens
<220> FEATURE:
<221> NAME/KEY: CDS
<222> LOCATION: (1)..(2178)

<400> SEQUENCE: 15

atg atg gag gcc atc aag aaa aag atg cag atg ctg aag tta gac aag       48
Met Met Glu Ala Ile Lys Lys Lys Met Gln Met Leu Lys Leu Asp Lys
1               5                   10                  15

gag aat gct ctg gat cgg gca gag caa gct gaa gct gag cag aag cag       96
Glu Asn Ala Leu Asp Arg Ala Glu Gln Ala Glu Ala Glu Gln Lys Gln
            20                  25                  30

gca gaa gaa aga agt aaa cag ctg gag gat gag ctg gca gcc atg cag      144
Ala Glu Glu Arg Ser Lys Gln Leu Glu Asp Glu Leu Ala Ala Met Gln
        35                  40                  45

aag aag ctg aaa ggg aca gag gat gag ctg gac aag tat tct gaa gct      192
Lys Lys Leu Lys Gly Thr Glu Asp Glu Leu Asp Lys Tyr Ser Glu Ala
    50                  55                  60

ttg aag gat gcc cag gag aag ctg gaa ctg gca gag aag aag gct gct      240
Leu Lys Asp Ala Gln Glu Lys Leu Glu Leu Ala Glu Lys Lys Ala Ala
65                  70                  75                  80

gat gct gag gct gag gtg gcc tcc ttg aac cgt agg atc cag ctg gtt      288
Asp Ala Glu Ala Glu Val Ala Ser Leu Asn Arg Arg Ile Gln Leu Val
                85                  90                  95

gaa gaa gag ctg gac cgt gct cag gag cgc ctg gcc act gcc ctg caa      336
Glu Glu Glu Leu Asp Arg Ala Gln Glu Arg Leu Ala Thr Ala Leu Gln
            100                 105                 110

aag ctg gaa gaa gct gaa aaa gct gct gat gag agt gag aga ggt atg      384
Lys Leu Glu Glu Ala Glu Lys Ala Ala Asp Glu Ser Glu Arg Gly Met
        115                 120                 125

aag gtt att gaa aac cgg gcc tta aaa gat gaa gaa aag atg gaa ctc      432
Lys Val Ile Glu Asn Arg Ala Leu Lys Asp Glu Glu Lys Met Glu Leu
    130                 135                 140

cag gaa atc caa ctc aaa gaa gct aag cac att gca gaa gag gca gat      480
Gln Glu Ile Gln Leu Lys Glu Ala Lys His Ile Ala Glu Glu Ala Asp
145                 150                 155                 160

agg aag tat gaa gag gtg gct cgt aag ttg gtg atc att gaa gga gac      528
Arg Lys Tyr Glu Glu Val Ala Arg Lys Leu Val Ile Ile Glu Gly Asp
                165                 170                 175
```

-continued

```
ttg gaa cgc aca gag gaa cga gct gag ctg gca gag tcc cgt tgc cga      576
Leu Glu Arg Thr Glu Glu Arg Ala Glu Leu Ala Glu Ser Arg Cys Arg
            180                 185                 190

gag atg gat gag cag att aga ctg atg gac cag aac ctg aag tgt ctg      624
Glu Met Asp Glu Gln Ile Arg Leu Met Asp Gln Asn Leu Lys Cys Leu
        195                 200                 205

agt gct gct gaa gaa aag tac tct caa aaa gaa gat aaa tat gag gaa      672
Ser Ala Ala Glu Glu Lys Tyr Ser Gln Lys Glu Asp Lys Tyr Glu Glu
    210                 215                 220

gaa atc aag att ctt act gat aaa ctc aag gag gca gag acc cgt gct      720
Glu Ile Lys Ile Leu Thr Asp Lys Leu Lys Glu Ala Glu Thr Arg Ala
225                 230                 235                 240

gag ttt gct gag aga tcg gta gcc aag ctg gaa aag aca att gat gac      768
Glu Phe Ala Glu Arg Ser Val Ala Lys Leu Glu Lys Thr Ile Asp Asp
                245                 250                 255

ctg gaa gtc tgg cat aga aga tta aag aat caa aaa agt gcc aag gaa      816
Leu Glu Val Trp His Arg Arg Leu Lys Asn Gln Lys Ser Ala Lys Glu
            260                 265                 270

ggg gtg aca gtg ctt ata aac gaa gac aaa gag ttg gct gag ctg cga      864
Gly Val Thr Val Leu Ile Asn Glu Asp Lys Glu Leu Ala Glu Leu Arg
        275                 280                 285

ggt ctg gca gcc gga gta ggc ctg gct aat gcc tgc tat gca ata cat      912
Gly Leu Ala Ala Gly Val Gly Leu Ala Asn Ala Cys Tyr Ala Ile His
    290                 295                 300

act ctt cca acc caa gag gag att gaa aat ctt cct gcc ttc cct cgg      960
Thr Leu Pro Thr Gln Glu Glu Ile Glu Asn Leu Pro Ala Phe Pro Arg
305                 310                 315                 320

gaa aaa ctg act ctg cgt ctc ttg ctg gga agt gga gcc ttt gga gaa     1008
Glu Lys Leu Thr Leu Arg Leu Leu Leu Gly Ser Gly Ala Phe Gly Glu
                325                 330                 335

gtg tat gaa gga aca gca gtg gac atc tta gga gtt gga agt gga gaa     1056
Val Tyr Glu Gly Thr Ala Val Asp Ile Leu Gly Val Gly Ser Gly Glu
            340                 345                 350

atc aaa gta gca gtg aag act ttg aag aag ggt tcc aca gac cag gag     1104
Ile Lys Val Ala Val Lys Thr Leu Lys Lys Gly Ser Thr Asp Gln Glu
        355                 360                 365

aag att gaa ttc ctg aag gag gca cat ctg atg agc aaa ttt aat cat     1152
Lys Ile Glu Phe Leu Lys Glu Ala His Leu Met Ser Lys Phe Asn His
    370                 375                 380

ccc aac att ctg aag cag ctt gga gtt tgt ctg ctg aat gaa ccc caa     1200
Pro Asn Ile Leu Lys Gln Leu Gly Val Cys Leu Leu Asn Glu Pro Gln
385                 390                 395                 400

tac att atc ctg gaa ctg atg gag gga gga gac ctt ctt act tat ttg     1248
Tyr Ile Ile Leu Glu Leu Met Glu Gly Gly Asp Leu Leu Thr Tyr Leu
                405                 410                 415

cgt aaa gcc cgg atg gca acg ttt tat ggt cct tta ctc acc ttg gtt     1296
Arg Lys Ala Arg Met Ala Thr Phe Tyr Gly Pro Leu Leu Thr Leu Val
            420                 425                 430

gac ctt gta gac ctg tgt gta gat att tca aaa ggc tgt gtc tac ttg     1344
Asp Leu Val Asp Leu Cys Val Asp Ile Ser Lys Gly Cys Val Tyr Leu
        435                 440                 445

gaa cgg atg cat ttc att cac agg gat ctg gca gct aga aat tgc ctt     1392
Glu Arg Met His Phe Ile His Arg Asp Leu Ala Ala Arg Asn Cys Leu
    450                 455                 460

gtt tcc gtg aaa gac tat acc agt cca cgg ata gtg aag att gga gac     1440
Val Ser Val Lys Asp Tyr Thr Ser Pro Arg Ile Val Lys Ile Gly Asp
465                 470                 475                 480

ttt gga ctc gcc aga gac atc tat aaa aat gat tac tat aga aag aga     1488
Phe Gly Leu Ala Arg Asp Ile Tyr Lys Asn Asp Tyr Tyr Arg Lys Arg
```

-continued

```
                485                 490                 495

ggg gaa ggc ctg ctc cca gtt cgg tgg atg gct cca gaa agt ttg atg     1536
Gly Glu Gly Leu Leu Pro Val Arg Trp Met Ala Pro Glu Ser Leu Met
            500                 505                 510

gat gga atc ttc act act caa tct gat gta tgg tct ttt gga att ctg     1584
Asp Gly Ile Phe Thr Thr Gln Ser Asp Val Trp Ser Phe Gly Ile Leu
        515                 520                 525

att tgg gag att tta act ctt ggt cat cag cct tat cca gct cat tcc     1632
Ile Trp Glu Ile Leu Thr Leu Gly His Gln Pro Tyr Pro Ala His Ser
    530                 535                 540

aac ctt gat gtg tta aac tat gtg caa aca gga ggg aga ctg gag cca     1680
Asn Leu Asp Val Leu Asn Tyr Val Gln Thr Gly Gly Arg Leu Glu Pro
545                 550                 555                 560

cca aga aat tgt cct gat gat ctg tgg aat tta atg acc cag tgc tgg     1728
Pro Arg Asn Cys Pro Asp Asp Leu Trp Asn Leu Met Thr Gln Cys Trp
                565                 570                 575

gct caa gaa ccc gac caa aga cct act ttt cat aga att cag gac caa     1776
Ala Gln Glu Pro Asp Gln Arg Pro Thr Phe His Arg Ile Gln Asp Gln
            580                 585                 590

ctt cag tta ttc aga aat ttt ttc tta aat agc att tat aag tcc aga     1824
Leu Gln Leu Phe Arg Asn Phe Phe Leu Asn Ser Ile Tyr Lys Ser Arg
        595                 600                 605

gat gaa gca aac aac agt gga gtc ata aat gaa agc ttt gaa ggt gaa     1872
Asp Glu Ala Asn Asn Ser Gly Val Ile Asn Glu Ser Phe Glu Gly Glu
    610                 615                 620

gat ggc gat gtg att tgt ttg aat tca gat gac att atg cca gtt gct     1920
Asp Gly Asp Val Ile Cys Leu Asn Ser Asp Asp Ile Met Pro Val Ala
625                 630                 635                 640

tta atg gaa acg aag aac cga gaa ggg tta aac tat atg gta ctt gct     1968
Leu Met Glu Thr Lys Asn Arg Glu Gly Leu Asn Tyr Met Val Leu Ala
                645                 650                 655

aca gaa tgt ggc caa ggt gaa gaa aag tct gag ggt cct cta ggc tcc     2016
Thr Glu Cys Gly Gln Gly Glu Glu Lys Ser Glu Gly Pro Leu Gly Ser
            660                 665                 670

cag gaa tct gaa tct tgt ggt ctg agg aaa gaa gag aag gaa cca cat     2064
Gln Glu Ser Glu Ser Cys Gly Leu Arg Lys Glu Glu Lys Glu Pro His
        675                 680                 685

gca gac aaa gat ttc tgc caa gaa aaa caa gtg gct tac tgc cct tct     2112
Ala Asp Lys Asp Phe Cys Gln Glu Lys Gln Val Ala Tyr Cys Pro Ser
    690                 695                 700

ggc aag cct gaa ggc ctg aac tat gcc tgt ctc act cac agt gga tat     2160
Gly Lys Pro Glu Gly Leu Asn Tyr Ala Cys Leu Thr His Ser Gly Tyr
705                 710                 715                 720

gga gat ggg tct gat taa                                             2178
Gly Asp Gly Ser Asp
                725


<210> SEQ ID NO 16
<211> LENGTH: 725
<212> TYPE: PRT
<213> ORGANISM: Homo sapiens

<400> SEQUENCE: 16

Met Met Glu Ala Ile Lys Lys Lys Met Gln Met Leu Lys Leu Asp Lys
1               5                   10                  15

Glu Asn Ala Leu Asp Arg Ala Glu Gln Ala Glu Ala Glu Gln Lys Gln
            20                  25                  30

Ala Glu Glu Arg Ser Lys Gln Leu Glu Asp Glu Leu Ala Ala Met Gln
        35                  40                  45
```

```
Lys Lys Leu Lys Gly Thr Glu Asp Glu Leu Asp Lys Tyr Ser Glu Ala
    50                  55                  60

Leu Lys Asp Ala Gln Glu Lys Leu Glu Leu Ala Glu Lys Lys Ala Ala
65                  70                  75                  80

Asp Ala Glu Ala Glu Val Ala Ser Leu Asn Arg Arg Ile Gln Leu Val
                85                  90                  95

Glu Glu Glu Leu Asp Arg Ala Gln Glu Arg Leu Ala Thr Ala Leu Gln
            100                 105                 110

Lys Leu Glu Glu Ala Glu Lys Ala Ala Asp Glu Ser Glu Arg Gly Met
        115                 120                 125

Lys Val Ile Glu Asn Arg Ala Leu Lys Asp Glu Glu Lys Met Glu Leu
    130                 135                 140

Gln Glu Ile Gln Leu Lys Glu Ala Lys His Ile Ala Glu Glu Ala Asp
145                 150                 155                 160

Arg Lys Tyr Glu Glu Val Ala Arg Lys Leu Val Ile Ile Glu Gly Asp
                165                 170                 175

Leu Glu Arg Thr Glu Glu Arg Ala Glu Leu Ala Glu Ser Arg Cys Arg
            180                 185                 190

Glu Met Asp Glu Gln Ile Arg Leu Met Asp Gln Asn Leu Lys Cys Leu
        195                 200                 205

Ser Ala Ala Glu Glu Lys Tyr Ser Gln Lys Glu Asp Lys Tyr Glu Glu
    210                 215                 220

Glu Ile Lys Ile Leu Thr Asp Lys Leu Lys Glu Ala Glu Thr Arg Ala
225                 230                 235                 240

Glu Phe Ala Glu Arg Ser Val Ala Lys Leu Glu Lys Thr Ile Asp Asp
                245                 250                 255

Leu Glu Val Trp His Arg Arg Leu Lys Asn Gln Lys Ser Ala Lys Glu
            260                 265                 270

Gly Val Thr Val Leu Ile Asn Glu Asp Lys Glu Leu Ala Glu Leu Arg
        275                 280                 285

Gly Leu Ala Ala Gly Val Gly Leu Ala Asn Ala Cys Tyr Ala Ile His
    290                 295                 300

Thr Leu Pro Thr Gln Glu Glu Ile Glu Asn Leu Pro Ala Phe Pro Arg
305                 310                 315                 320

Glu Lys Leu Thr Leu Arg Leu Leu Leu Gly Ser Gly Ala Phe Gly Glu
                325                 330                 335

Val Tyr Glu Gly Thr Ala Val Asp Ile Leu Gly Val Gly Ser Gly Glu
            340                 345                 350

Ile Lys Val Ala Val Lys Thr Leu Lys Lys Gly Ser Thr Asp Gln Glu
        355                 360                 365

Lys Ile Glu Phe Leu Lys Glu Ala His Leu Met Ser Lys Phe Asn His
    370                 375                 380

Pro Asn Ile Leu Lys Gln Leu Gly Val Cys Leu Leu Asn Glu Pro Gln
385                 390                 395                 400

Tyr Ile Ile Leu Glu Leu Met Glu Gly Gly Asp Leu Leu Thr Tyr Leu
                405                 410                 415

Arg Lys Ala Arg Met Ala Thr Phe Tyr Gly Pro Leu Leu Thr Leu Val
            420                 425                 430

Asp Leu Val Asp Leu Cys Val Asp Ile Ser Lys Gly Cys Val Tyr Leu
        435                 440                 445

Glu Arg Met His Phe Ile His Arg Asp Leu Ala Ala Arg Asn Cys Leu
    450                 455                 460

Val Ser Val Lys Asp Tyr Thr Ser Pro Arg Ile Val Lys Ile Gly Asp
```

```
465                 470                 475                 480

Phe Gly Leu Ala Arg Asp Ile Tyr Lys Asn Asp Tyr Tyr Arg Lys Arg
                485                 490                 495

Gly Glu Gly Leu Leu Pro Val Arg Trp Met Ala Pro Glu Ser Leu Met
            500                 505                 510

Asp Gly Ile Phe Thr Thr Gln Ser Asp Val Trp Ser Phe Gly Ile Leu
        515                 520                 525

Ile Trp Glu Ile Leu Thr Leu Gly His Gln Pro Tyr Pro Ala His Ser
    530                 535                 540

Asn Leu Asp Val Leu Asn Tyr Val Gln Thr Gly Gly Arg Leu Glu Pro
545                 550                 555                 560

Pro Arg Asn Cys Pro Asp Asp Leu Trp Asn Leu Met Thr Gln Cys Trp
                565                 570                 575

Ala Gln Glu Pro Asp Gln Arg Pro Thr Phe His Arg Ile Gln Asp Gln
            580                 585                 590

Leu Gln Leu Phe Arg Asn Phe Phe Leu Asn Ser Ile Tyr Lys Ser Arg
        595                 600                 605

Asp Glu Ala Asn Asn Ser Gly Val Ile Asn Glu Ser Phe Glu Gly Glu
    610                 615                 620

Asp Gly Asp Val Ile Cys Leu Asn Ser Asp Asp Ile Met Pro Val Ala
625                 630                 635                 640

Leu Met Glu Thr Lys Asn Arg Glu Gly Leu Asn Tyr Met Val Leu Ala
                645                 650                 655

Thr Glu Cys Gly Gln Gly Glu Glu Lys Ser Glu Gly Pro Leu Gly Ser
            660                 665                 670

Gln Glu Ser Glu Ser Cys Gly Leu Arg Lys Glu Glu Lys Glu Pro His
        675                 680                 685

Ala Asp Lys Asp Phe Cys Gln Glu Lys Gln Val Ala Tyr Cys Pro Ser
    690                 695                 700

Gly Lys Pro Glu Gly Leu Asn Tyr Ala Cys Leu Thr His Ser Gly Tyr
705                 710                 715                 720

Gly Asp Gly Ser Asp
                725


<210> SEQ ID NO 17
<211> LENGTH: 28
<212> TYPE: DNA
<213> ORGANISM: Homo sapiens

<400> SEQUENCE: 17

atttgctcat cagatgtgcc tccttcag                                        28


<210> SEQ ID NO 18
<211> LENGTH: 24
<212> TYPE: DNA
<213> ORGANISM: Homo sapiens

<400> SEQUENCE: 18

acgctattaa tcagacccat ctcc                                            24


<210> SEQ ID NO 19
<211> LENGTH: 22
<212> TYPE: DNA
<213> ORGANISM: Homo sapiens

<400> SEQUENCE: 19

ctctctattt cccaaacaac gc                                              22
```

<210> SEQ ID NO 20
<211> LENGTH: 21
<212> TYPE: DNA
<213> ORGANISM: Homo sapiens

<400> SEQUENCE: 20
ccttctccag tccgcggtgc c 21

<210> SEQ ID NO 21
<211> LENGTH: 22
<212> TYPE: DNA
<213> ORGANISM: Homo sapiens

<400> SEQUENCE: 21
tcccagatgc acaggaggag aa 22

<210> SEQ ID NO 22
<211> LENGTH: 24
<212> TYPE: DNA
<213> ORGANISM: Homo sapiens

<400> SEQUENCE: 22
ccagaaaccg aaaatgccga aacc 24

<210> SEQ ID NO 23
<211> LENGTH: 24
<212> TYPE: DNA
<213> ORGANISM: Homo sapiens

<400> SEQUENCE: 23
tgaccatggc tccctggcct gaat 24

<210> SEQ ID NO 24
<211> LENGTH: 24
<212> TYPE: DNA
<213> ORGANISM: Homo sapiens

<400> SEQUENCE: 24
ctgggagctt cgggtagaga ccta 24

<210> SEQ ID NO 25
<211> LENGTH: 33
<212> TYPE: DNA
<213> ORGANISM: Artificial Sequence
<220> FEATURE:
<223> OTHER INFORMATION: Description of Artificial Sequence: synthetic
primer

<400> SEQUENCE: 25
gtgtgaattc gtgagcctac caacagccac tgc 33

<210> SEQ ID NO 26
<211> LENGTH: 24
<212> TYPE: DNA
<213> ORGANISM: Homo sapiens

<400> SEQUENCE: 26
cacgggtctc tgcctccttg agtt 24

<210> SEQ ID NO 27
<211> LENGTH: 23
<212> TYPE: DNA
<213> ORGANISM: Homo sapiens

<400> SEQUENCE: 27
cctgaagtgt ctgagtgctg ctg 23

<210> SEQ ID NO 28
<211> LENGTH: 23
<212> TYPE: DNA
<213> ORGANISM: Homo sapiens

<400> SEQUENCE: 28
ctttctggag ccatccaccg aac 23

<210> SEQ ID NO 29
<211> LENGTH: 22
<212> TYPE: DNA
<213> ORGANISM: Homo sapiens

<400> SEQUENCE: 29
ccagtctcca gttctccagt gt 22

<210> SEQ ID NO 30
<211> LENGTH: 24
<212> TYPE: DNA
<213> ORGANISM: Homo sapiens

<400> SEQUENCE: 30
cccaaacaac gctattaatc agac 24

<210> SEQ ID NO 31
<211> LENGTH: 22
<212> TYPE: DNA
<213> ORGANISM: Homo sapiens

<400> SEQUENCE: 31
ctgtcacccc ttccttggca ct 22

<210> SEQ ID NO 32
<211> LENGTH: 19
<212> TYPE: DNA
<213> ORGANISM: Homo sapiens

<400> SEQUENCE: 32
cactgtcacc ccttccttg 19

<210> SEQ ID NO 33
<211> LENGTH: 28
<212> TYPE: DNA
<213> ORGANISM: Homo sapiens

<400> SEQUENCE: 33
atttgctcat cagatgtgcc tccttcag 28

<210> SEQ ID NO 34
<211> LENGTH: 20
<212> TYPE: DNA
<213> ORGANISM: Homo sapiens

<400> SEQUENCE: 34
agtcgccgag tcgatccgag 20

<210> SEQ ID NO 35
<211> LENGTH: 24
<212> TYPE: DNA

-continued

```
<213> ORGANISM: Homo sapiens

<400> SEQUENCE: 35

ctggaaggtc tttgagagct ggat                                    24


<210> SEQ ID NO 36
<211> LENGTH: 21
<212> TYPE: DNA
<213> ORGANISM: Homo sapiens

<400> SEQUENCE: 36

gatgatgcgc gagaaggagg a                                       21


<210> SEQ ID NO 37
<211> LENGTH: 25
<212> TYPE: DNA
<213> ORGANISM: Homo sapiens

<400> SEQUENCE: 37

gcccaacccc gataagtacc tcgaa                                   25


<210> SEQ ID NO 38
<211> LENGTH: 21
<212> TYPE: DNA
<213> ORGANISM: Homo sapiens

<400> SEQUENCE: 38

acacagatga gaccaacttg c                                       21


<210> SEQ ID NO 39
<211> LENGTH: 23
<212> TYPE: DNA
<213> ORGANISM: Homo sapiens

<400> SEQUENCE: 39

agagacccgt gctgagtttg ctg                                     23
```